US012404342B2

(12) United States Patent
Woods et al.

(10) Patent No.: US 12,404,342 B2
(45) Date of Patent: *Sep. 2, 2025

(54) CONJUGATES FOR TARGETED CELL SURFACE EDITING

(71) Applicant: The Board of Trustees of the Leland Stanford Junior University, Stanford, CA (US)

(72) Inventors: Elliot C. Woods, Burlingame, CA (US); Han Xiao, East Palo Alto, CA (US); Carolyn R. Bertozzi, Menlo Park, CA (US); Melissa Gray, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 22 days.

This patent is subject to a terminal disclaimer.

(21) Appl. No.: 17/822,638

(22) Filed: Aug. 26, 2022

(65) Prior Publication Data
US 2023/0287140 A1    Sep. 14, 2023

Related U.S. Application Data

(63) Continuation of application No. 16/308,732, filed as application No. PCT/US2017/040411 on Jun. 30, 2017, now Pat. No. 11,459,398.

(Continued)

(51) Int. Cl.
*C07K 16/32* (2006.01)
*A61P 35/00* (2006.01)
(Continued)

(52) U.S. Cl.
CPC .............. *C07K 16/32* (2013.01); *A61P 35/00* (2018.01); *C07K 19/00* (2013.01); *C12N 9/2402* (2013.01);
(Continued)

(58) Field of Classification Search
None
See application file for complete search history.

(56) References Cited

U.S. PATENT DOCUMENTS

| 4,510,129 A | 4/1985 | Knop et al. |
| 4,975,278 A | 12/1990 | Senter et al. |

(Continued)

FOREIGN PATENT DOCUMENTS

| WO | WO 2014037785 | 3/2014 | |
| WO | WO-2014037785 A2 * | 3/2014 | ........... C12N 9/0002 |

(Continued)

OTHER PUBLICATIONS

Bhat et al., 2014, BioProcess International, downloaded from https://bioprocessintl.com/manufacturing/monoclonal-antibodies/next-step-homogenous-bioconjugate-development-optimizing-payload-plac (Year: 2014).*

(Continued)

*Primary Examiner* — Karl J Puttlitz
(74) *Attorney, Agent, or Firm* — Brian E. Davy; Bozicevic, Field & Francis LLP

(57) ABSTRACT

Provided are conjugates including a targeting moiety that binds to a cell surface molecule of a target cell and a target cell surface-editing enzyme. Also provided are compositions and kits that include the conjugates, as well as methods of using the conjugates. Methods of making conjugates are also provided.

25 Claims, 33 Drawing Sheets
Specification includes a Sequence Listing.

Related U.S. Application Data

(60) Provisional application No. 62/357,645, filed on Jul. 1, 2016.

(51) Int. Cl.
    *C07K 19/00*     (2006.01)
    *C12N 9/24*     (2006.01)

(52) U.S. Cl.
    CPC ................ *C12Y 302/01018* (2013.01); *C07K 2317/732* (2013.01); *C07K 2319/035* (2013.01); *C07K 2319/33* (2013.01); *C07K 2319/74* (2013.01)

(56) References Cited

U.S. PATENT DOCUMENTS

| | | |
|---|---|---|
| 6,877,169 B2 | 4/2005 | Acquaviva |
| 7,645,448 B2 | 1/2010 | Fang et al. |
| 7,807,174 B2 | 10/2010 | Fang et al. |
| 8,084,036 B2 | 12/2011 | Yu et al. |
| 8,398,971 B2 | 3/2013 | Fang et al. |
| 8,512,710 B2 | 8/2013 | Fang et al. |
| 8,623,419 B2 | 1/2014 | Malakhov et al. |
| 8,722,869 B2 | 5/2014 | Fang et al. |
| 9,212,353 B2 | 12/2015 | Fang et al. |
| 9,764,007 B2 | 9/2017 | Fang et al. |
| 10,280,191 B2 | 5/2019 | Deamer |
| 10,300,116 B2 | 5/2019 | Moss |
| 10,328,128 B2 | 6/2019 | Moss |
| 10,351,828 B2 | 7/2019 | Hawley |
| 10,525,109 B2 | 1/2020 | Fang et al. |
| 10,918,736 B2 | 2/2021 | Kim et al. |
| 10,940,185 B2 | 3/2021 | Yasukawa et al. |
| 2011/0135570 A1 | 6/2011 | Janatpour |
| 2011/0142912 A1 | 6/2011 | Moser et al. |
| 2015/0152187 A1* | 6/2015 | Sun ................... C07K 16/3076 530/391.1 |
| 2017/0119859 A1 | 5/2017 | Moss |
| 2018/0271997 A1* | 9/2018 | Wang ................... C07K 14/58 |
| 2019/0247460 A1 | 8/2019 | Connaris et al. |
| 2020/0164049 A1 | 5/2020 | Moss |
| 2020/0222511 A1 | 7/2020 | Moss |

FOREIGN PATENT DOCUMENTS

| | | |
|---|---|---|
| WO | WO 2016038064 | 3/2016 |
| WO | WO 2017100725 | 6/2017 |
| WO | WO 2018231661 | 12/2018 |
| WO | WO 2020018996 | 1/2020 |

OTHER PUBLICATIONS

Miyagi et al., Glycobiology vol. 22 No. 7 pp. 880-896, 2012 (Year: 2012).*

Gray et al. (2020) "Targeted Glycan Degradation Potentiates the Anticancer Immune Response in Vivo" Nature Chemical Biology, vol. 16, No. 2, pp. 1376-1384.

Alley and Snodgrass (1977) "Effectiveness of Neuraminidase in Experimental Immunotherapy of Two Murine Pulmonary Carcinomas" Cancer Research, 37:95-101.

Bhat et al. (2021) "The Next Step in Homogenous Bioconjugate Development: Optimizing Payload Placement and Conjugate Composition" BioProcess International, downloaded from https://bioprocessintl.com/manufacturing/monoclonal-antibodies/next-step-homogenous-bioconjugate-development-optimizing-payload-placement-conjugate-composition.

Bosch et al. (2013) "Drugs Targeting B-Cells in Autoimmune Diseases" Springer Science & Business Media, pp. 1-4.

Chu et al. (2006) "Lineage Determination of CD20-B-Cell Neoplasms: An Immunohistochemical Study" Am J Clin Pathol 126:534-544.

Hudak et al. (2014) "Glycocalyx engineering reveals a Siglec-based mechanism for NK cell immunoevasion" Nat. Chem.Biol. 10:69-75.

Jandus et al. (2014) "Interactions between Siglec-7/9 receptors and ligands influence NK cell-dependent tumor immunosurveillance" J. Clin. Invest. 124:1810-1820.

Kim et al. (2011) "Features and applications of bacterial sialidases" Appl Microbiol Biotechnol., 91:1-15.

Malakhov et al. (2006) "Sialidase Fusion Protein as a Novel Broad-Spectrum Inhibitor of Influenza Virus Infection" Antimicrobial Agents and Chemotherapy, 50(4):1470-1479.

McCombs et al. (2016) "Enhanced Cross-Linking of Diazirine-Modified Sialylated Glycoproteins Enabled through Profiling of Sialidase Specificities" ACS Chem. Biol., 11:185-192.

Mitri et al. (2012) "The HER2 Receptor in Breast Cancer: Pathophysiology, Clinical Use, and New Advances in Therapy" Chemotherapy Research and Practice vol. 2012, Article ID 743193, 7 pages.

Rabuka et al (2012) "Site-specific chemical protein conjugation using genetically encoded aldehyde tags" Nature Protocols, 7(6):1052-1067.

"Trastuzumab Product Approval Information—Licensing Action Sep. 25, 1998". U.S. Food and Drug Administration (FDA). Retrieved Jun. 7, 2021.

Tseng et al. (2007) "Desialylation of human cancer cells leading apoptosis by treatment with purified and overexpressed nanI cloned from Clostridium perfringens ATCC 10543" Enzyme and Microbial Tech., 41(1-2):5-12.

Van Rooijen et al. (1992) "Monoclonal antibody mediated targeting of enzymes—A comparative study using the mouse spleen as a model system" Journal Of Immunological Methods, 151(1-2):149-155.

Xiao et al. (2016) "Precision glycocalyx editing as a strategy for cancer immunotherapy" Proceedings Of The National Academy Of Sciences, 113(37):10304-10309.

\* cited by examiner

A

| | Size (kDa) | Activity (U/mg)* |
|---|---|---|
| *Homo sapiens* Neu2 | 44 | 0.3 ± 0.1 |
| *Homo sapiens* Neu3 | 50 | 0.1 ± 0.1 |
| *Vibrio cholerae* Sia | 83 | 10.5 ± 0.8 |
| *Salmonella typhimurium* Sia | 46 | 114.0 ± 4.8 |
| *Clostridium perfringens* Sia | 44 | 41.4 ± 3.4 |
| *Arthrobacter ureafaciens* Sia | 52 | 3.1 ± 0.4 |

C

Siglec 9 ligand expression

CONJUGATES FOR TARGETED CELL SURFACE EDITING

CROSS-REFERENCE TO RELATED APPLICATIONS

This application claims the benefit of U.S. Provisional Patent Application No. 62/357,645 filed Jul. 1, 2016, which application is incorporated herein by reference in its entirety.

STATEMENT REGARDING FEDERALLY SPONSORED RESEARCH

This invention was made with Government support under contracts GM059907 and CA108781 awarded by the National Institutes of Health. The Government has certain rights in the invention.

INCORPORATION BY REFERENCE OF SEQUENCE LISTING PROVIDED AS A SEQUENCE LISTING XML FILE

A Sequence Listing is provided herewith as a Sequence Listing XML, STAN-1302CON_SEQ_LIST, created on Aug. 26, 2022 and having a size of 7,164 bytes. The contents of the Sequence Listing XML are incorporated herein by reference in their entirety.

INTRODUCTION

Therapies that enhance the immune response to cancer are proving revolutionary in the fight against intractable tumors. Immune cells integrate signals from activating and inhibitory receptors to determine their response to a challenging target—activating signals alert them to the presence of pathology while inhibitory signals tell the cell that it has confronted a healthy "self". Successful tumors evolve mechanisms to thwart immune cell recognition, often by overexpressing ligands for inhibitory receptors. This discovery has led to new therapeutic strategies aimed at blocking inhibitory immune cell signaling, as embodied in clinically approved T cell checkpoint inhibitors targeting PD-1 and CTLA-4. Ongoing pre-clinical studies have focused on combining therapies targeting multiple immunologic pathways. For example, antibodies against PD-1/PD-L1 in combination with those targeting other T cell checkpoint inhibitors demonstrate improved anti-tumor activity in syngeneic tumor models. A complement to these interventions are therapies targeting innate immune cells, particularly natural killer (NK) cells, macrophages and dendritic cells.

SUMMARY

Provided are conjugates including a targeting moiety that binds to a cell surface molecule of a target cell and a target cell surface-editing enzyme. Also provided are compositions and kits that include the conjugates, as well as methods of using the conjugates. Methods of making conjugates are also provided.

DETAILED DESCRIPTION

Figure 1:
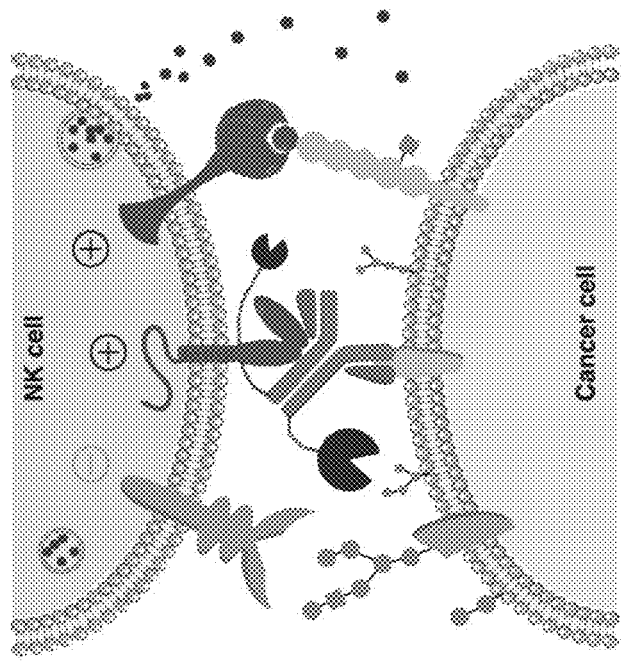
FIG. 1 schematically illustrates an immune evasion strategy and a method of reducing such immune evasion according to one embodiment of the present disclosure.
Figure 1:
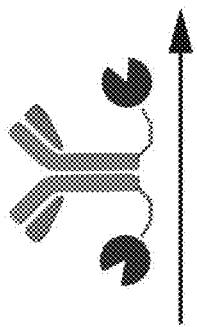
Figure 1:
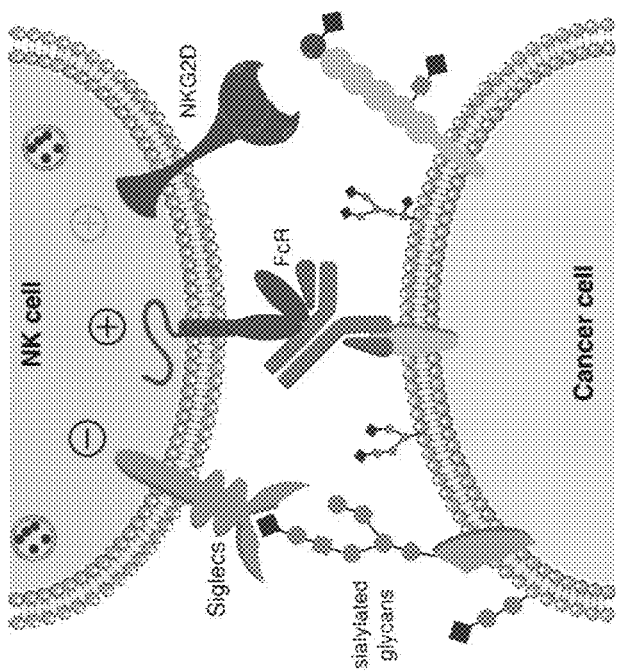

Provided are conjugates including a targeting moiety that binds to a cell surface molecule of a target cell and a target cell surface-editing enzyme. Also provided are compositions and kits that include the conjugates, as well as methods of using the conjugates. Methods of making conjugates are also provided.

Before the conjugates, compositions and methods of the present disclosure are described in greater detail, it is to be understood that the conjugates, compositions and methods are not limited to particular embodiments described, as such may, of course, vary. It is also to be understood that the terminology used herein is for the purpose of describing particular embodiments only, and is not intended to be limiting, since the scope of the conjugates, compositions and methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the conjugates, compositions and methods. The upper and lower limits of these smaller ranges may independently be included in the smaller ranges and are also encompassed within the conjugates, compositions and methods, subject to any specifically excluded limit in the stated range. Where the stated range includes one or both of the limits, ranges excluding either or both of those included limits are also included in the conjugates, compositions and methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the conjugates, compositions and methods belong. Although any conjugates, compositions and methods similar or equivalent to those described herein can also be used in the practice or testing of the conjugates, compositions and methods, representative illustrative conjugates, compositions and methods are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present conjugates, compositions and methods are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the conjugates, compositions and methods, which are, for clarity, described in the context of separate embodiments, may also be provided in combination in a single embodiment. Conversely, various features of the conjugates, compositions and methods, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions. In addition, all sub-combinations listed in the embodiments describing such variables are also specifically embraced by the present conjugates, compositions and methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order that is logically possible.

Conjugates

As summarized above, aspects of the present disclosure include conjugates. In certain aspects, the conjugates include a targeting moiety that binds to a cell surface molecule of a target cell, and a target cell surface-editing enzyme.

Targeting Moieties

According to certain embodiments, a conjugate of the present disclosure includes a targeting moiety. The targeting moiety may vary and may be selected based, e.g., on the nature of the cell surface molecule on the target cell. Non-limiting examples of a targeting moiety that may be employed include an antibody, a ligand, an aptamer, a nanoparticle, and a small molecule.

In certain aspects, the targeting moiety specifically binds to the cell surface molecule. As used herein, a targeting moiety that "specifically binds to the cell surface molecule" or is "specific for the cell surface molecule" refers to a targeting moiety that binds the cell surface molecule with greater affinity than with other cell surface molecules. According to certain embodiments, the targeting moiety exhibits a binding affinity to the cell surface molecule of a $K_d$ of less than or equal to about $10^{-5}$ M, less than or equal to about $10^{-6}$ M, or less than or equal to about $10^{-7}$ M, or less than or equal to about $10^{-8}$ M, or less than or equal to about $10^{-9}$ M, $10^{-10}$ M, $10^{-11}$ M, or $10^{-12}$ M or less. Such affinities may be readily determined using conventional techniques, such as by equilibrium dialysis, surface plasmon resonance (SPR) technology (e.g., the BIAcore 2000 instrument, using general procedures outlined by the manufacturer), radioimmunoassay, or by another method.

According to certain embodiments, the targeting moiety is an antibody. The terms "antibody" and "immunoglobulin" include antibodies or immunoglobulins of any isotype (e.g., IgG (e.g., IgG1, IgG2, IgG3, or IgG4), IgE, IgD, IgA, IgM, etc.), whole antibodies (e.g., antibodies composed of a tetramer which in turn is composed of two dimers of a heavy and light chain polypeptide); single chain antibodies; fragments of antibodies (e.g., fragments of whole or single chain antibodies) which retain specific binding to the cell surface molecule of the target cell, including, but not limited to single chain Fv (scFv), Fab, (Fab')$_2$, (scFv')$_2$, and diabodies; chimeric antibodies; monoclonal antibodies, human antibodies, humanized antibodies (e.g., humanized whole antibodies, humanized half antibodies, or humanized antibody fragments); and fusion proteins comprising an antigen-binding portion of an antibody and a non-antibody protein. The antibodies may be detectably labeled, e.g., with an in vivo imaging agent, a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like.

In certain aspects, when the targeting moiety is an antibody, the antibody may be a therapeutic antibody even in the absence of the target cell surface-editing enzyme, e.g., an antibody having efficacy on its own in the treatment of cancer (e.g., via antibody-dependent cellular cytotoxicity and/or another mechanism), an immune-related disorder, an endothelial cell-related disorder, or the like. For example, the antibody may be a therapeutic antibody that specifically binds to a tumor-associated cell surface molecule or a tumor-specific cell surface molecule.

Non-limiting examples of antibodies that specifically bind to a tumor-associated cell surface molecule or a tumor-specific cell surface molecule which may be employed in a conjugate of the present disclosure include Adecatumumab, Ascrinvacumab, Cixutumumab, Conatumumab, Daratumumab, Drozitumab, Duligotumab, Durvalumab, Dusigitumab, Enfortumab, Enoticumab, Figitumumab, Ganitumab, Glembatumumab, Intetumumab, Ipilimumab, Iratumumab, Icrucumab, Lexatumumab, Lucatumumab, Mapatumumab, Narnatumab, Necitumumab, Nesvacumab, Ofatumumab, Olaratumab, Panitumumab, Patritumab, Pritumumab, Radretumab, Ramucirumab, Rilotumumab, Robatumumab, Seribantumab, Tarextumab, Teprotumumab, Tovetumab, Vantictumab, Vesencumab, Votumumab, Zalutumumab, Flanvotumab, Altumomab, Anatumomab, Arcitumomab, Bectumomab, Blinatumomab, Detumomab, Ibritumomab, Minretumomab, Mitumomab, Moxetumomab, Naptumomab, Nofetumomab, Pemtumomab, Pintumomab, Racotumomab, Satumomab, Solitomab, Taplitumomab, Tenatumomab, Tositumomab, Tremelimumab, Abagovomab, Igovomab, Oregovomab, Capromab, Edrecolomab, Nacolomab, Amatuximab, Bavituximab, Brentuximab, Cetuximab, Derlotuximab, Dinutuximab, Ensituximab, Futuximab, Girentuximab, Indatuximab, Isatuximab, Margetuximab, Rituximab, Siltuximab, Ublituximab, Ecromeximab, Abituzumab, Alemtuzumab, Bevacizumab, Bivatuzumab, Brontictuzumab, Cantuzumab, Cantuzumab, Citatuzumab, Clivatuzumab, Dacetuzumab, Demcizumab, Dalotuzumab, Denintuzumab, Elotuzumab, Emactuzumab, Emibetuzumab, Enoblituzumab, Etaracizumab, Farletuzumab, Ficlatuzumab, Gemtuzumab, Imgatuzumab, Inotuzumab, Labetuzumab, Lifastuzumab, Lintuzumab, Lorvotuzumab, Lumretuzumab, Matuzumab, Milatuzumab, Nimotuzumab, Obinutuzumab, Ocaratuzumab, Otlertuzumab, Onartuzumab, Oportuzumab, Parsatuzumab, Pertuzumab, Pinatuzumab, Polatuzumab, Sibrotuzumab, Simtuzumab, Tacatuzumab, Tigatuzumab, Trastuzumab, Tucotuzumab, Vandortuzumab, Vanucizumab, Veltuzumab, Vorsetuzumab, Sofituzumab, Catumaxomab, Ertumaxomab, Depatuxizumab, Ontuxizumab, Blontuvetmab, Tamtuvetmab, or an antigen-binding variant thereof. As used herein, "variant" is meant the antibody binds to the particular antigen (e.g., HER2 for trastuzumab) but has fewer or more amino acids than the parental antibody, has one or more amino acid substitutions relative to the parental antibody, or a combination thereof.

In certain aspects, the targeting moiety is a therapeutic antibody set forth in Table 1 below approved for treating cancer, or an antigen-binding variant thereof. Also provided in Table 1 is the corresponding tumor-associated cell surface molecule or tumor-specific cell surface molecule to which the therapeutic antibody specifically binds, as well as the type of cancer for which the antibody is approved for treatment.

TABLE 1

Antibodies approved for treating cancer

| Cell surface molecule | Cancer Types | Antibody |
|---|---|---|
| BCR-ABL | CML | Imatinib, Dasatinib |
|  | ALL | Nilotinib, Bosutinib |
|  |  | Ponatinib |
| CD19 | ALL | Blinatumomab |
| CD20 | NHL, CLL | Rituximab |
|  | B-cell NHL | Ofatumumab |
|  | pre-B ALL | $^{90}$Y-Ibritumomab |
|  |  | $^{131}$I-Tositumomab |
| CD30 | Hodgkin's lymphoma | Brentuximab vedotin |
| CD33 | AML | Gemtuzumab ozogamicin |
| CD52 | CLL | Alemtuzumab |
| CTLA-4 | Unresectable or metastatic melanoma | Ipilimumab |
| EGFR | CRC | Cetuximab |
|  | Head and Neck | Panitumumab |
| EpCAM | Malignant ascites | Catumaxomab |
| HER2 | Breast | Trastuzumab |
|  |  | Pertuzumab |
| PAP | Prostate | Sipuleucel-T |
| PD-1 | Metastatic melanoma NSCLC | Nivolumab |
|  |  | Pembrolizumab |
| VEGF | Breast, Cervical | Bevacizumab |
|  | CRC, NSCLC |  |
|  | RCC, Ovarian |  |
|  | Glioblastoma |  |
| VEGF-R2 | Gastric | Ramucirumab |
|  | NSCLC |  |

Abbreviations for Table 1 are as follows: ALL, acute lymphoblastic leukemia; AML, acute myelogenous leukemia; BCR-ABL, breakpoint cluster region Abelson tyrosine kinase; CLL, chronic lymphocytic leukemia; CTLA-4, cytotoxic T-lymphocyte-associated antigen 4; CRC, colorectal cancer; EGFR, epidermal growth factor receptor; EpCAM, epithelial cell adhesion molecule; HER2, human epidermal growth factor receptor 2; NHL, non-Hodgkin's lymphoma; NSCLC, non-small cell lung cancer; PAP, prostatic acid phosphatase; PD-1, programmed cell death receptor 1; RCC, renal cell carcinoma; VEGF, vascular endothelial growth factor; VEGF-R2, vascular endothelial growth factor receptor 2.

In some embodiments, the targeting moiety is a therapeutic antibody set forth in Table 2 below or an antigen-binding variant thereof. Also provided in Table 2 is the corresponding tumor-associated cell surface molecule or tumor-specific cell surface molecule to which the therapeutic antibody specifically binds, as well as an example cancer type which may be treated using a conjugate that includes the antibody.

TABLE 2

Additional antibodies, cell surface molecules, and cancer types

| Cell surface molecule | Cancer types | Antibody |
|---|---|---|
| A2aR | NSCLC | PBF-509 |
| AKAP4 | NSCLC Ovarian | Preclinical |
| BAGE | Glioblastoma Ovarian | Preclinical |
| BORIS | Prostate, Lung Esophageal | Preclinical |
| CD22 | ALL | Epratuzumab Moxetumomab Inotuzumab ozogamicin |
| CD73 | Advanced solid tumors | MEDI9447 |
| CD137 | Advanced solid tumors | Urelumab PF-05082566 |
| CEA | CRC | PANVAC ™ Ad5-[E1-, E2b-]-CEA(6D) |
| CS1 | Multiple myeloma | Elotuzumab |
| CTLA-4 | Malignant mesothelioma | Tremelimumab |
| EBAG9 | Bladder | Preclinical |
| EGF | NSCLC | CIMAvax |
| EGFR | NSCLC | Necitumumab |
| GAGE | Cervical | Preclinical |
| GD2 | Neuroblastoma Retinoblastoma Melanoma other solid tumors | Dinutuximab, hu3F8 hu14.18-IL-2, 3F8/OKT3BsAb anti-GD2 CAR GD2-KLH |
| gp100 | Melanoma | gp100: 209-217(210M) |
| HPV-16 | Cervical SCCHN | HPV-16 (E6, E7) TG4001, Lm-LLO-E7 pNGVL4a-CRT/E7, INO-3112 |
| HSP105 | CRC Bladder | Preclinical |
| IDH1 | Glioma | IDH1(R132H) p123-142 |
| Idiotype (NeuGcGM3) | NSCLC, Breast Melanoma | Racotumomab |
| IDO1 | Breast, Melanoma NSCLC | Indoximod INCB024360 IDO1 peptide vaccine |
| KIR | Lymphoma | Lirilumab |
| LAG-3 | Breast, Hematological, Advanced solid tumors | BMS-986016 IMP321 |
| LY6K | Gastric SCCHN | LY6K-177 peptide LY6K, CDCA1, IMP3 |
| MAGE-A3 | Melanoma NSCLC | recMAGE-A3 Zastumotide |
| MAGE-C2 | Gastric, Melanoma Multiple myeloma | Preclinical |
| MAGE-D4 | CRC | Preclinical |
| Melan-A | Melanoma | MART-1 (26-35, 27L) |
| MET | NSCLC | Onartuzumab Tivantinib |
| MUC1 | NSCLC, Breast Prostate | Tecemotide, TG4010 PANVAC ™ |
| MUC4 | Pancreatic | Preclinical |
| MUC16 | Ovarian | Abagovomab Oregovomab |
| NY-ESO-1 | Ovarian Melanoma | NY-ESO-1/ISCOMATRIX ™ rV-NY-ESO-1; rF-NY-ESO-1 |
| PD-1 | B-cell lymphoma Melanoma, CRC | Pidilizumab AMP-224, AMP-514 |
| PD-L1 | NSCLC, RCC Bladder, Breast Melanoma, SCCHN | BMS-936559, Atezolizumab Durvalumab, Avelumab |
| PRAME | NSCLC | Preclinical |
| PSA | Prostate | PROSTVAC ®-VF |
| ROR1 | CLL, Pancreatic Lung, Breast | Preclinical |
| Sialyl-Tn | Breast | Theratope |
| SPAG-9 | Prostate, CRC NSCLC, Ovarian | Preclinical |
| SSX1 | Prostate Multiple myeloma | Preclinical |
| Survivin | Melanoma Glioma, Solid tumors | EMD640744 Trivalent peptide vaccine Tripeptide vaccine |

TABLE 2-continued

Additional antibodies, cell surface molecules, and cancer types

| Cell surface molecule | Cancer types | Antibody |
|---|---|---|
| Telomerase | Pancreatic | Tertomotide |
| TIM-3 | Melanoma, NHL NSCLC | Preclinical |
| VISTA | Melanoma, Bladder | Preclinical |
| WT1 | Ovarian, Uterine, AML Multiple myeloma | WT1 peptide vaccine |
| XAGE-1b | Prostate | DC-based tumor vaccine |
| 5T4 | RCC, CRC | TroVax ® |
|  | Prostate | Naptumomab estafenatox |

Abbreviations for Table 2 are as follows: A2aR, adenosine A2a receptor; AKAP4, A kinase anchor protein 4; AML, acute myelogenous leukemia; ALL, acute lymphoblastic leukemia; BAGE, B melanoma antigen; BORIS, brother of the regulator of imprinted sites; CEA, carcinoembryonic antigen; CLL, chronic lymphocytic leukemia; CRC, colorectal cancer; CS1, CD2 subset 1; CTLA-4, cytotoxic T-lymphocyte-associated antigen 4; EBAG9, estrogen receptor binding site associated antigen 9; EGF, epidermal growth factor; EGFR, epidermal growth factor receptor; NSCLC, non-small cell lung cancer; GAGE, G antigen; GD2, disialoganglioside GD2; gp100, glycoprotein 100; HPV-16, human papillomavirus 16; HSP105, heat-shock protein 105; IDH1, isocitrate dehydrogenase type 1; IDO1, indoleamine-2,3-dioxygenase 1; KIR, killer cell immunoglobulin-like receptor; LAG-3, lymphocyte activation gene 3; LY6K, lymphocyte antigen 6 complex K; MAGE-A3, melanoma antigen 3; MAGE-C2, melanoma antigen C2; MAGE-D4, melanoma antigen D4; Melan-A/MART-1, melanoma antigen recognized by T-cells 1; MET, N-methyl-N'-nitroso-guanidine human osteosarcoma transforming gene; MUC1, mucin 1; MUC4, mucin 4; MUC16, mucin 16; NHL, non-Hodgkin lymphoma; NY-ESO-1, New York esophageal squamous cell carcinoma 1; PD-1, programmed cell death receptor 1; PD-L1, programmed cell death receptor ligand 1; PRAME, preferentially expressed antigen of melanoma; PSA, prostate specific antigen; RCC, renal cell carcinoma; ROR1, receptor tyrosine kinase orphan receptor 1; SCCHN, squamous cell carcinoma of the head and neck; SPAG-9, sperm-associated antigen 9; SSX1, synovial sarcoma X-chromosome breakpoint 1; TIM-3, T-cell immunoglobulin domain and mucin domain-3; VISTA, V-domain immunoglobulin-containing suppressor of T-cell activation; WT1, Wilms' Tumor-1; XAGE-1b, X chromosome antigen 1b.

In some embodiments, the targeting moiety is a therapeutic antibody set forth in Table 3 below or an antigen-binding variant thereof. Also provided in Table 3 is the corresponding tumor-associated cell surface molecule or tumor-specific cell surface molecule to which the therapeutic antibody specifically binds.

TABLE 3

Additional antibodies and corresponding cell surface molecules

| Antibody | Cell Surface Molecule |
|---|---|
| oregovomab | CA125 |
| girentuximab | CAIX |
| obinutuzumab | CD20 |
| ofatumumab | CD20 |
| rituximab | CD20 |
| alemtuzumab | CD52 |
| ipilimumab | CTLA-4 |
| tremelimumab | CTLA-4 |
| cetuximab | EGFR |
| necitumumab | EGFR |
| panitumumab | EGFR |
| zalutumumab | EGFR |
| edrecolomab | EpCAM (17-1A) |
| farletuzumab | FR-alpha |
| pertuzumab | Her2 |
| trastuzumab | Her2 |
| rilotumumab | HGF |
| figitumumab | IGF-1 |
| ganitumab | IGF1R |
| durvalumab | IGG1K |
| bavituximab | Phosphatidylserine |
| onartuzumab | scatter factor receptor kinase |
| bevacizumab | VEGF-A |
| ramucirumab | VEGFR2 |

In some embodiments, a conjugate of the present disclosure includes a therapeutic antibody as the targeting moiety selected from trastuzumab, cetuximab, daratumumab, girentuximab, panitumumab, ofatumumab, rituximab, and antigen-binding variants thereof.

In certain aspects, a conjugate of the present disclosure includes a therapeutic antibody as the targeting moiety, and the therapeutic antibody is trastuzumab or a HER2-binding variant thereof. The heavy and light chain amino acid sequences of trastuzumab are known and provided in Table 4 below.

TABLE 4

Trastuzumab heavy and light chain amino acid sequences

Trastuzumab Light Chain (SEQ ID NO: 1)
DIQMTQSPSSLSASVGDRVTITCRASQDVNTAVAW
YQQKPGKAPKLLIYSASFLYSGVPSRFSGSRSGTD
FTLTISSLQPEDFATYYCQQHYTTPPTFGQGTKVEI
KRTVAAPSVFIFPPSDEQLKSGTASVVCLLNNFYPR
EAKVQWKVDNALQSGNSQESVTEQDSKDSTYSLS
STLTLSKADYEKHKVYACEVTHQGLSSPVTKSFNR
GEC Trastuzumab Heavy Chain (SEQ ID NO: 2)
EVQLVESGGGLVQPGGSLRLSCAASGFNIKDTYIH
WVRQAPGKGLEWVARIYPTNGYTRYADSVKGRFTI
SADTSKNTAYLQMNSLRAEDTAVYYCSRWGGDGF
YAMDYWGQGTLVTVSSASTKGPSVFPLAPSSKSTS
GGTAALGCLVKDYFPEPVTVSWNSGALTSGVHTFP
AVLQSSGLYSLSSVVTVPSSSLGTQTYICNVNHKPS
NTKVDKKVEPPKSCDKTHTCPPCPAPELLGGPSVF
LFPPKPKDTLMISRTPEVTCVVVDVSHEDPEVKFN
WYVDGVEVHNAKTKPREEQYNSTYRVVSVLTVLH
QDWLNGKEYKCKVSNKALPAPIEKTISKAKGQPRE
PQVYTLPPSRDELTKNQVSLTCLVKGFYPSDIAVE
WESNGQPENNYKTTPPVLDSDGSFFLYSKLTVDKS
RWQQGNVFSCSVMHEALHNHYTQKSLSLSPGK When the targeting moiety is an antibody, the target cell surface-editing enzyme may be conjugated to any suitable region of the antibody. In certain aspects, the targeting moiety is an antibody having a light chain polypeptide, and the target cell surface-editing enzyme is conjugated to the light chain, e.g., at the C-terminus or an internal region of the light chain. According to certain embodiments, the targeting moiety is an antibody having a heavy chain polypeptide, and the target cell surface-editing enzyme is conjugated to the heavy chain, e.g., at the C-terminus or an internal region of the heavy chain. If the antibody having a heavy chain includes a fragment crystallizable (Fc) region, the target cell surface-editing enzyme may be conjugated to the Fc region, e.g., at the C-terminus or an internal region of the Fc region.

According to certain embodiments, the targeting moiety is a ligand. As used herein, a "ligand" is a substance that forms a complex with a biomolecule to serve a biological purpose. The ligand may be a substance selected from a circulating factor, a secreted factor, a cytokine, a growth factor, a hormone, a peptide, a polypeptide, a small molecule, and a nucleic acid, that forms a complex with the cell surface molecule on the surface of the target cell. In certain aspects, when the targeting moiety is a ligand, the ligand is modified in such a way that complex formation with the cell surface molecule occurs, but the normal biological result of such complex formation does not occur. In certain aspects, the ligand is the ligand of a cell surface receptor present on the target cell. Cell surface receptors of interest include, but are not limited to, receptor tyrosine kinases (RTKs), non-receptor tyrosine kinases (non-RTKs), growth factor receptors, etc. When the conjugates of the present disclosure include a ligand as the targeting moiety, the target cell surface-editing enzyme may be conjugated to any suitable region of the ligand, e.g., a region of attachment that does not interfere or substantially interfere with the ability of the ligand to bind (e.g., specifically bind) the target cell surface molecule.

In certain aspects, the targeting moiety is an aptamer. By "aptamer" is meant a nucleic acid (e.g., an oligonucleotide) that has a specific binding affinity for the target cell surface molecule. Aptamers exhibit certain desirable properties for targeted delivery of the target cell surface-editing enzyme, such as ease of selection and synthesis, high binding affinity and specificity, low immunogenicity, and versatile synthetic accessibility. Aptamers that bind to cell surface molecules are known and include, e.g., TTA1 (a tumor targeting aptamer to the extracellular matrix protein tenascin-C). Aptamers that find use in the conjugates of the present disclosure include those described in Zhu et al. (2015) ChemMedChem 10(1):39-45; Sun et al. (2014) Mol. Ther. Nucleic Acids 3:e182; and Zhang et al. (2011) Curr. Med. Chem. 18(27):4185-4194.

According to certain embodiments, the targeting moiety is a nanoparticle. As used herein, a "nanoparticle" is a particle having at least one dimension in the range of from 1 nm to 1000 nm, from 20 nm to 750 nm, from 50 nm to 500 nm, including 100 nm to 300 nm, e.g., 120-200 nm. The nanoparticle may have any suitable shape, including but not limited to spherical, spheroid, rod-shaped, disk-shaped, pyramid-shaped, cube-shaped, cylinder-shaped, nanohelical-shaped, nanospring-shaped, nanoring-shaped, arrow-shaped, teardrop-shaped, tetrapod-shaped, prism-shaped, or any other suitable geometric or non-geometric shape. In certain aspects, the nanoparticle includes on its surface one or more of the other targeting moieties described herein, e.g., antibodies, ligands, aptamers, small molecules, etc. Nanoparticles that find use in the conjugates of the present disclosure include those described in Wang et al. (2010) Pharmacol. Res. 62(2):90-99; Rao et al. (2015) ACS Nano 9(6):5725-5740; and Byrne et al. (2008) Adv. Drug Deliv. Rev. 60(15):1615-1626.

In certain aspects, the targeting moiety is a small molecule. By "small molecule" is meant a compound having a molecular weight of 1000 atomic mass units (amu) or less. In some embodiments, the small molecule is 750 amu or less, 500 amu or less, 400 amu or less, 300 amu or less, or 200 amu or less. In certain aspects, the small molecule is not made of repeating molecular units such as are present in a polymer. In certain aspects, the target cell surface molecule is a receptor for which the ligand is a small molecule, and the small molecule of the conjugate is the small molecule ligand (or a derivative thereof) of the receptor. Small molecules that find use in targeting a conjugate to a target cell of interest are known. As just one example, folic acid (FA) derivatives have been shown to effectively target certain types of cancer cells by binding to the folate receptor, which is overexpressed, e.g., in many epithelial tumors. See, e.g., Vergote et al. (2015) Ther. Adv. Med. Oncol. 7(4):206-218.

In another example, the small molecule sigma-2 has proven to be effective in targeting cancer cells. See, e.g., Hashim et al. (2014) *Molecular Oncology* 8(5):956-967. Sigma-2 is the small molecule ligand for sigma-2 receptors, which are overexpressed in many proliferating tumor cells including pancreatic cancer cells. In certain aspects, a conjugate of the present disclosure includes a small molecule as the targeting moiety, in which it has been demonstrated in the context of a small molecule drug conjugate (SMDC) that the small molecule is effective at targeting a conjugate to a target cell of interest by binding to a cell surface molecule on the target cell.

Target Cell Surface Editing Enzymes

As summarized above, the conjugates of the present disclosure include a target cell surface-editing enzyme. As used herein, a "target cell surface-editing enzyme" is an enzyme which, upon binding of the targeting moiety to the corresponding cell surface molecule of the target cell, effects a structural change in one or more molecules on the surface of the target cell. In certain aspects, the structural change is to the cell surface molecule to which the targeting moiety binds. In other aspects, the structural change is to a molecule on the surface of the target cell other than the cell surface molecule to which the targeting moiety binds.

In certain aspects, the target cell surface-editing enzyme is a wild-type enzyme (that is, an enzyme found in nature). In other aspects, the enzyme is not a wild-type enzyme. For example, the target cell surface-editing enzyme may be a non-natural derivative of a wild-type enzyme. Such derivatives at least partially retain the enzymatic activity of the corresponding wild-type enzyme. Enzyme derivatives that may be employed include those that have fewer amino acids or more amino acids than the corresponding wild-type enzyme. Alternatively, or additionally, the enzyme derivatives may include one or more amino acid substitutions or amino acid modifications relative to the corresponding wild-type enzyme.

An example of a structural change effected by a target cell surface-editing enzyme in a molecule on the surface of the target cell is the cleavage of the molecule. In certain aspects, the molecule cleaved by the target cell surface-editing enzyme is a polymer. Cell surface polymers which may be cleaved (e.g., degraded) by the target cell surface-editing enzyme include, but are not limited to, polypeptides, polysaccharides, glycoproteins, and the like. For example, the target cell surface-editing enzyme may be a protease that cleaves polypeptides (or a subgroup of interest thereof) on the surface of the target cell. In certain aspects, the polymer cleaved by the target cell surface-editing enzyme is a polysaccharide (or "glycan"), that is, a molecule containing monosaccharides linked glycosidically. In such embodiments, the target cell surface-editing enzyme may be, e.g., a glycoside hydrolase (e.g., a sialidase).

According to certain embodiments, the cell surface-editing enzyme cleaves (e.g., hydrolyzes) a terminal residue of a molecule (e.g., a polymer) on the surface of the target cell. In certain aspects, the terminal residue is present in a molecule selected from a oligosaccharide, a polysaccharide, a glycoprotein, a glycolipid, and a ganglioside. In some embodiments the terminal residue is a terminal sialic acid residue. When the terminal residue is a terminal sialic acid residue, the cell surface-editing enzyme may be a sialidase (or a derivative thereof as described above), which cleaves the glycosidic linkages of sialic (neuraminic) acids, releasing terminal sialic acid residues from oligosaccharides, polysaccharides, glycoproteins, glycolipids, and other substrates.

Sialidases which may be employed in the conjugates of the present disclosure include, but are not limited to, prokaryotic sialidases and eukaryotic sialidases. Prokaryotic sialidases that may be employed include bacterial sialidases. One example of a bacterial sialidase that finds use in the conjugates of the present disclosure is *Salmonella typhimurium* sialidase (e.g., UniProtKB—P29768). Another example of a bacterial sialidase that finds use in the conjugates of the present disclosure is *Vibrio cholera* sialidase (e.g., UniProtKB—P0C6E9). Eukaryotic sialidases that may be employed include, e.g., mammalian sialidases and non-mammalian eukaryotic sialidases. Mammalian sialidases (or mammalian neuraminidases) of interest include those from primates, e.g., human or non-human neuraminidases. In certain aspects, the sialidase is a human sialidase. According to certain embodiments, the human sialidase is selected from human neuraminidase 1 (e.g., UniProtKB—Q99519), human neuraminidase 2 (e.g., UniProtKB—Q9Y3R4), human neuraminidase 3 (e.g., UniProtKB—Q9UQ49), and human neuraminidase 4 (e.g., UniProtKB—Q8WWR8). It will be understood that the sialidase may be a derivative of any of the wild-type sialidases above, such as truncated derivatives, derivatives that include more amino acids than the corresponding wild-type sialidase, derivatives that include one or more amino acid substitutions (e.g., one or more conservative substitutions, one or more non-conservative substitutions, a substitution of a natural amino acid with a non-natural amino acid, and/or the like), etc. The derivatives retain at least a portion of the glycoside hydrolase activity of the parental wild-type sialidase.

TABLE 5

Amino acid sequences of example sialidases

| | |
|---|---|
| *Salmonella typhimurium* sialidase (SEQ ID NO: 3) | TVEKSVVFKAEGEHFTDQKGNTIVGSGSGGTTKYFRIPAMCTTS KGTIVVFADARHNTASDQSFIDTAAARSTDGGKTWNKKIAIYND RVNSKLSRVMDPTCIVANIQGRETILVMVGKWNNNDKTWGAYR DKAPDTDWDLVLYKSTDDGVTFSKVETNIHDIVTKNGTISAMLG GVGSGLQLNDGKLVFPVQMVRTKNITTVLNTSFIYSTDGITWSL PSGYCEGFGSENNIIEFNASLVNNIRNSGLRRSFETKDFGKTWT EFPPMDKKVDNRNHGVQGSTITIPSGNKLVAAHSSAQNKNNDY TRSDISLYAHNLYSGEVKLIDDFYPKVGNASGAGYSCLSYRKNV DKETLYVVYEANGSIEFQDLSRHLPVIKSYN |
| *Vibrio cholerae* sialidase (SEQ ID NO: 4) | ALFDYNATGDTEFDSPAKQGWMQDNTNNGSGVLTNADGMPA WLVQGIGGRAQWTYSLSTNQHAQASSFGWRMTTEMKVLSGG MITNYYANGTQRVLPIISLDSSGNLVVEFEGQTGRTVLATGTAAT EYHKFELVFLPGSNPSASFYFDGKLIRDNIQPTASKQNMIVWGN GSSNTDGVAAYRDIKFEIQGDVIFRGPDRIPSIVASSVTPGVVTA FAEKRVGGGDPGALSNTNDIITRTSRDGGITWDTELNLTEQINV |

TABLE 5-continued

Amino acid sequences of example sialidases

```
SDEFDFSDPRPIYDPSSNTVLVSYARWPTDAAQNGDRIKPWMP
NGIFYSVYDVASGNWQAPIDVTDQVKERSFQIAGWGGSELYRR
NTSLNSQQDWQSNAKIRIVDGAANQIQVADGSRKYVVTLSIDES
GGLVANLNGVSAPIILQSEHAKVHSFHDYELQYSALNHTTTLFV
DGQQITTWAGEVSQENNIQFGNADAQIDGRLHVQKIVLTQQGH
NLVEFDAFYLAQQTPEVEKDLEKLGWTKIKTGNTMSLYGNASV
NPGPGHGITLTRQQNISGSQNGRLIYPAIVLDRFFLNVMSIYSDD
GGSNWQTGSTLPIPFRWKSSSILETLEPSEADMVELQNGDLLLT
ARLDFNQIVNGVNYSPRQQFLSKDGGITWSLLEANNANVFSNIS
TGTVDASITRFEQSDGSHFLLFTNPQGNPAGTNGRQNLGLWFS
FDEGVTWKGPIQLVNGASAYSDIYQLDSENAIVIVETDNSNMRIL
RMPITLLKQKLTLSQN
```

According to certain embodiments, the target cell surface-editing enzyme edits (e.g., cleaves all or a portion of) a ligand on the surface of the target cell. In some embodiments, the ligand is a ligand of an immune receptor. Immune receptor ligands of interest include, but are not limited to, ligands of inhibitory immune receptors. In certain aspects, the target cell surface-editing enzyme cleaves a ligand of an inhibitory immune receptor, where the inhibitory immune receptor is present on a cell selected from a natural killer (NK) cell, a macrophage, a monocyte, a neutrophil, a dendritic cell, a T cell, a B cell, a mast cell, a basophil, and an eosinophil. By way of example, the ligand on the surface of the target cell edited by the target cell surface-editing enzyme may be a ligand for a sialic acid-binding Ig-like lectin (Siglec) receptor, e.g., Siglec 7, Siglec 9, and/or the like. According to certain embodiments, such a ligand is a sialoglycan.

In certain aspects, a structural change in a molecule on the surface of the target cell effected by the target cell surface-editing enzyme is the oxidation of the molecule.

In some embodiments, the structural change in a molecule on the surface of the target cell effected by the target cell surface-editing enzyme is the reduction of the molecule.

In certain aspects, the target cell surface-editing enzyme effects a structural change in a molecule on the surface of the target cell by adding a moiety to the molecule. For example, the target cell surface-editing enzyme may be a transferase that transfers a functional group to the molecule from a donor molecule. In some embodiments, the target cell surface-editing enzyme is a kinase that adds a phosphate group to the molecule on the surface of the target cell.

According to some embodiments, the target cell surface-editing enzyme effects a structural change in a molecule on the surface of the target cell by removing a moiety from the molecule. For example, the target cell surface-editing enzyme may be a transferase that transfers a functional group from the molecule to an acceptor molecule. In some embodiments, the target cell surface-editing enzyme is a phosphatase that removes a phosphate group from the molecule on the surface of the target cell.

Target Cells

The targeting moiety and target cell surface-editing enzyme may be selected based on the cell to be targeted. According to certain embodiments, the target cell is selected from a cancer cell, an immune cell, an endothelial cell, and an epithelial cell. Target cells of interest include, but are not limited to, cells that are relevant to a particular disease or condition. For example, the target cell may be a normal functioning cell (e.g., a normal functioning immune cell, etc.), and the cell surface editing enzyme modulates the function of the cell in a manner that is therapeutic to an individual in need thereof, e.g., boosts a function of the cell that is beneficial in treating a disease in an individual.

In other aspects, the target cell is not a normal cell. Non-normal target cells of interest include, but are not limited to, cancer cells. By "cancer cell" is meant a cell exhibiting a neoplastic cellular phenotype, which may be characterized by one or more of, for example, abnormal cell growth, abnormal cellular proliferation, loss of density dependent growth inhibition, anchorage-independent growth potential, ability to promote tumor growth and/or development in an immunocompromised non-human animal model, and/or any appropriate indicator of cellular transformation. "Cancer cell" may be used interchangeably herein with "tumor cell", "malignant cell" or "cancerous cell", and encompasses cancer cells of a solid tumor, a semi-solid tumor, a primary tumor, a metastatic tumor, and the like. In certain aspects, the cancer cell is a carcinoma cell. According to certain embodiments, the cancer cell is selected from a breast cancer cell, an ovarian cancer cell, a gastric cancer cell, a colon cancer cell, and a cancer cell of any of the cancer types set forth in Tables 1 and 2 above.

In certain aspects, when the target cell is a cancer cell, the molecule on the surface of the cancer cell to which the targeting moiety binds is a tumor-associated cell surface molecule or a tumor-specific cell surface molecule. By "tumor-associated cell surface molecule" is meant a cell surface molecule expressed on malignant cells with limited expression on cells of normal tissues, a cell surface molecule expressed at much higher density on malignant versus normal cells, or a cell surface molecule that is developmentally expressed.

When the target cell is a cancer cell, the cancer cell may express a tumor-associated cell surface molecule or tumor-specific cell surface molecule to which the targeting moiety binds. In certain aspects, such a cell surface molecule is selected from HER2, CD19, CD22, CD30, CD33, CD56, CD66/CEACAM5, CD70, CD74, CD79b, CD138, Nectin-4, Mesothelin, Transmembrane glycoprotein NMB (GPNMB), Prostate-Specific Membrane Antigen (PSMA), SLC44A4, CA6, CA-IX, an integrin, C-X-C chemokine receptor type 4 (CXCR4), cytotoxic T-lymphocyte-associated protein 4 (CTLA-4), neuropilin-1 (NRP1), matriptase, any cell surface molecule set forth in Tables 1, 2, and 3 above, and any other tumor-associated or tumor-specific cell surface molecules of interest.

Methods of Making Conjugates

Methods of making the conjugates of the present disclosure are also provided.

In cases where one wishes to produce the targeting moiety and/or the target cell surface-editing enzyme (e.g., because a particular targeting moiety and/or target cell surface-editing enzyme is not commercially available), the methods may include producing one or both of the targeting moiety and target cell surface-editing enzyme.

When a component of the desired conjugate (that is, the targeting moiety or target cell surface-editing enzyme) is a peptide or polypeptide, recombinant methods can be used to produce the component. For example, a DNA encoding a component of the desired conjugate can be inserted into an expression vector. The DNA encoding the component may be operably linked to one or more control sequences in the expression vector that ensure the expression of the component. Expression control sequences include, but are not limited to, promoters (e.g., naturally-associated or heterologous promoters), signal sequences, enhancer elements, and transcription termination sequences. The expression control sequences can be promoter systems in vectors capable of transforming or transfecting prokaryotic or eukaryotic host cells. Once the vector has been incorporated into the appropriate host, the host is maintained under conditions suitable for high level expression of the nucleotide sequences, and the collection and purification of the component.

When a component of the desired conjugate (that is, the targeting moiety or target cell surface-editing enzyme) is a peptide or polypeptide, the component may be produced using a chemical peptide synthesis technique. Where a polypeptide is chemically synthesized, the synthesis may proceed via liquid-phase or solid-phase. Solid phase polypeptide synthesis (SPPS), in which the C-terminal amino acid of the sequence is attached to an insoluble support followed by sequential addition of the remaining amino acids in the sequence, is an example of a suitable method for the chemical synthesis of a component of the desired conjugate. Various forms of SPPS, such as Fmoc and Boc, are available for synthesizing the component. Briefly, small insoluble, porous beads may be treated with functional units on which peptide chains are built. After repeated cycling of coupling/deprotection, the free N-terminal amine of a solid-phase attached is coupled to a single N-protected amino acid unit. This unit is then deprotected, revealing a new N-terminal amine to which a further amino acid may be attached. The peptide remains immobilized on the solid-phase and undergoes a filtration process before being cleaved off.

Once synthesized (either chemically or recombinantly), the component can be purified according to standard procedures of the art, including ammonium sulfate precipitation, affinity columns, column chromatography, high performance liquid chromatography (HPLC) purification, gel electrophoresis, and the like.

Once the targeting moiety and target cell surface-editing enzyme are obtained, a variety of conjugation strategies are available, and a particular method may be selected based on the nature/type of targeting moiety and target cell surface-editing enzyme in the desired conjugate (e.g., based on available, or provided, reactive functional groups in the targeting moiety and target cell surface-editing enzyme). Bioconjugation strategies that find use in stably associating a targeting moiety and a target cell surface-editing enzyme to produce a conjugate of the present disclosure include those described in Hermanson, "Bioconjugate Techniques," Academic Press, 2nd edition, Apr. 1, 2008, Haugland, 1995, Methods Mol. Biol. 45:205-21; Brinkley, 1992, Bioconjugate Chemistry 3:2, and elsewhere.

According to certain embodiments, the targeting moiety and target cell surface-editing enzyme are directly conjugated to each other—that is, the components of the conjugate are conjugated to each other without the use of a linker. In other aspects, the targeting moiety and target cell surface-editing enzyme are conjugated to each other via a linker. Any suitable linker(s) may be employed. Linkers that find use in the conjugates of the present disclosure include ester linkers, amide linkers, maleimide or maleimide-based linkers; valine-citrulline linkers; hydrazone linkers; N-succinimidyl-4-(2-pyridyldithio)butyrate (SPDB) linkers; Succinimidyl-4-(N-maleimidomethyl)cyclohexane-1-carboxylate (SMCC) linkers; vinylsulfone-based linkers; linkers that include polyethylene glycol (PEG), such as, but not limited to tetraethylene glycol; linkers that include propanoic acid; linkers that include caproleic acid, and linkers including any combination thereof. In certain aspects, the linker includes polyethylene glycol (PEG). In some embodiments, the linker is a peptide linker. The peptide linker may be flexible or rigid. Peptide linkers of interest include, but are not limited to, those described in Chen et al. (2013) *Adv. Drug Deliv. Rev.* 65(10):1357-1369. In certain aspects, when the linker is a peptide linker, the conjugate is a fusion protein. When the conjugate is a fusion protein, the present disclosure further provides nucleic acids that encode such fusion proteins, expression vectors that include such nucleic acids operably linked to a promoter, and host cells (e.g., mammalian host cells) that include such fusion proteins, nucleic acids, and/or expression vectors. In certain aspects, the linker is serum-stable. Serum-stable linkers are known and include, e.g., linkers that include PEG, sulfone linkers (e.g., phenyloxadiazole sulfone linkers (see Patterson et al. (2014) *Bioconj. Chem.* 25(8):1402-7)), and the like.

Numerous strategies are available for linking the targeting moiety and target cell surface-editing enzyme via a linker. For example, one component of the conjugate may be derivatized by covalently attaching a linker to the component, where the linker has a functional group capable of reacting with a "chemical handle" on that component, and where the linker has a second functional group capable of reacting with a "chemical handle" on the other component. The functional groups on the linker may vary and may be selected based on compatibility with the chemical handles on the components of the desired conjugate. The conjugate components may already include a functional group useful for reacting with a functional group of the linker, or such a functional group may be provided to one or both components of the desired conjugate. Functional groups that may be used to bind components of the conjugates to a linker include, but are not limited to, active esters, isocyanates, imidoesters, hydrazides, amino groups, aldehydes, ketones, photoreactive groups, maleimide groups, alpha-halo-acetyl groups, epoxides, azirdines, and the like. Reagents such as iodoacetamides, maleimides, benzylic halides and bromomethylketones react by S-alkylation of thiols to generate stable thioether products. For example, at pH 6.5-7.5, maleimide groups react with sulfhydryl groups to form stable thioether bonds. Arylating reagents such as NBD halides react with thiols or amines by a similar substitution of the aromatic halide by the nucleophile. Because the thiolate anion is a better nucleophile than the neutral thiol, cysteine is more reactive above its $pK_a$ (~8.3, depending on protein structural context). Thiols also react with certain amine-reactive reagents, including isothiocyanates and succinimidyl esters. The TS-Link series of reagents are available for reversible thiol modification.

With respect to amine reactive groups, primary amines exist at the N-terminus of polypeptide chains and in the side-chain of lysine (Lys, K) amino acid residues. Among the available functional groups in typical biological or protein samples, primary amines are especially nucleophilic, making them ready targets for conjugation with several reactive groups. For example, NHS esters are reactive groups formed by carbodiimide-activation of carboxylate molecules. NHS ester-activated crosslinkers and labeling compounds react with primary amines in physiologic to slightly alkaline conditions (pH 7.2 to 9) to yield stable amide bonds. The reaction releases N-hydroxysuccinimide (NHS). Also by way of example, imidoester crosslinkers react with primary amines to form amidine bonds. Imidoester crosslinkers react rapidly with amines at alkaline pH but have short half-lives. As the pH becomes more alkaline, the half-life and reactivity with amines increases. As such, crosslinking is more efficient when performed at pH 10 than at pH 8. Reaction conditions below pH 10 may result in side reactions, although amidine formation is favored between pH 8-10.

Numerous other synthetic chemical groups will form chemical bonds with primary amines, including but not limited to, isothiocyanates, isocyanates, acyl azides, sulfonyl chlorides, aldehydes, glyoxals, epoxides, oxiranes, carbonates, aryl halides, carbodiimides, anhydrides, and fluorophenyl esters. Such groups conjugate to amines by either acylation or alkylation.

According to one embodiment, the chemical handle on the targeting moiety, target cell surface-editing enzyme, or both, is provided by incorporation of an unnatural amino acid having the chemical handle into the component. The unnatural amino acid may be incorporated via chemical synthesis or recombinant approaches, e.g., using a suitable orthogonal amino acyl tRNA synthetase-tRNA pair for incorporation of the unnatural amino acid during translation in a host cell. The functional group of an unnatural amino acid present in the component may be an azide, alkyne, alkene, amino-oxy, hydrazine, aldehyde, nitrone, nitrile oxide, cyclopropene, norbornene, iso-cyanide, aryl halide, boronic acid, or other suitable functional group, and the functional group on the linker is selected to react with the functional group of the unnatural amino acid (or vice versa).

In other aspects, the chemical handle on the targeting moiety, target cell surface-editing enzyme, or both, is provided using an approach that does not involve an unnatural amino acid. For example, a component containing no unnatural amino acid(s) could be conjugated to a linker by utilizing, e.g., nucleophilic functional groups of the component (such as the N-terminal amine or the primary amine of lysine, or any other nucleophilic amino acid residue) as a nucleophile in a substitution reaction with a linker construct bearing a reactive leaving group or other electrophilic group.

In certain aspects, the target cell surface-editing enzyme is site-specifically conjugated to the targeting moiety, the targeting moiety is site-specifically conjugated to the target cell surface-editing enzyme, or both. In some embodiments, site-specific conjugation is achieved by incorporating an unnatural amino acid having the reactive functional group at a predetermined location in the targeting moiety and/or target cell surface-editing enzyme. Details for site-specific incorporation of unnatural amino acids into proteins can be found, e.g., in Young & Schultz (2010) *J. Biol. Chem.* 285:11039-11044.

In certain aspects, the targeting moiety has a C-terminal aldehyde tag, and site-specific conjugation is achieved by reacting the C-terminal aldehyde with aminooxy-tetraethyleneglycol-azide (aminooxy-TEG-N$_3$), followed by reacting with a bicyclononyne-N-hydroxysuccinimde ester (BCN-NHS)-labeled target cell surface-editing enzyme. This example embodiment is described in more detail in the Experimental section below.

In certain aspects, the targeting moiety has a C-terminal aldehyde tag, and site specific conjugation is achieved by reacting the C-terminal aldehyde with aminooxy-tetraethyleneglycol-azide (aminooxy-TEG-N$_3$). A target cell surface editing enzyme has an aldehyde tag sequence (SLCTPSRGS), and site-specific conjugation is achieved by reacting aldehyde tag cysteine with Dibenzocyclooctyne-tetrapolyethyleneglycol-maleimide (DBCO-PEG4-maleimide) followed by reaction with the TEG-N$_3$-labeled targeting moiety. This example embodiment is described in more detail in the Experimental section below.

Accordingly, aspects of the present disclosure include methods that include conjugating a target cell surface-editing enzyme to a targeting moiety that binds to a cell surface molecule on the surface of a target cell. One or more (e.g., two or more, three or more, four or more, etc.) target cell surface-editing enzymes may be conjugated to the targeting moiety. The targeting moiety and target cell surface-editing enzyme may be any of the targeting moieties and target cell surface-editing enzymes described herein. As just one example, in some embodiments, the target cell surface-editing enzyme is a sialidase (e.g., any of the sialidases described herein) and the targeting moiety is an antibody (e.g., any of the antibodies described herein, including, by way of example, an anti-HER2 antibody (e.g., trastuzamab), cetuximab, daratumumab, girentuximab, panitumumab, ofatumumab, rituximab, etc.). As noted above, the conjugation may be site-specific (e.g., via a functional group of a non-natural amino acid at a predetermined position) with respect to the targeting moiety, the target cell surface-editing enzyme, or both.

Compositions

Also provided are compositions that include a conjugate of the present disclosure. The compositions may include any of the conjugates described herein (e.g., a conjugate having any of the targeting moieties and target cell surface-editing enzymes described herein). In certain aspects, the compositions include a conjugate of the present disclosure present in a liquid medium. The liquid medium may be an aqueous liquid medium, such as water, a buffered solution, or the like. One or more additives such as a salt (e.g., NaCl, MgCl$_2$, KCl, MgSO$_4$), a buffering agent (a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.), a solubilizing agent, a detergent (e.g., a non-ionic detergent such as Tween-20, etc.), a ribonuclease inhibitor, glycerol, a chelating agent, and the like may be present in such compositions.

Pharmaceutical compositions are also provided. The pharmaceutical compositions include any of the conjugates of the present disclosure, and a pharmaceutically acceptable carrier. The pharmaceutical compositions generally include a therapeutically effective amount of the conjugate. By "therapeutically effective amount" is meant a dosage sufficient to produce a desired result, e.g., an amount sufficient to effect beneficial or desired therapeutic (including preventative) results, such as a reduction in a symptom of a disease or disorder associated with the target cell or a population thereof, as compared to a control. An effective amount can be administered in one or more administrations.

A conjugate of the present disclosure can be incorporated into a variety of formulations for therapeutic administration. More particularly, the conjugate can be formulated into pharmaceutical compositions by combination with appropriate, pharmaceutically acceptable excipients or diluents, and may be formulated into preparations in solid, semi-solid, liquid or gaseous forms, such as tablets, capsules, powders, granules, ointments, solutions, injections, inhalants and aerosols.

Formulations of the conjugates of the present disclosure suitable for administration to a patient (e.g., suitable for human administration) are generally sterile and may further be free of detectable pyrogens or other contaminants contraindicated for administration to a patient according to a selected route of administration.

In pharmaceutical dosage forms, the conjugates can be administered in the form of their pharmaceutically acceptable salts, or they may also be used alone or in appropriate association, as well as in combination, with other pharmaceutically active compounds, e.g., an anti-cancer agent (including but not limited to small molecule anti-cancer agents), an immune checkpoint inhibitor, and any combination thereof. The following methods and carriers/excipients are merely examples and are in no way limiting.

For oral preparations, the conjugate can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The conjugate can be formulated for parenteral (e.g., intravenous, intra-arterial, intraosseous, intramuscular, intracerebral, intracerebroventricular, intrathecal, subcutaneous, etc.) administration. In certain aspects, the conjugate is formulated for injection by dissolving, suspending or emulsifying the conjugate in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Pharmaceutical compositions that include the conjugate may be prepared by mixing the conjugate having the desired degree of purity with optional physiologically acceptable carriers, excipients, stabilizers, surfactants, buffers and/or tonicity agents. Acceptable carriers, excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

The pharmaceutical composition may be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration.

An aqueous formulation of the conjugate may be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

A tonicity agent may be included in the formulation to modulate the tonicity of the formulation. Example tonicity agents include sodium chloride, potassium chloride, glycerin and any component from the group of amino acids, sugars as well as combinations thereof. In some embodiments, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 100 mM to 350 mM.

A surfactant may also be added to the formulation to reduce aggregation and/or minimize the formation of particulates in the formulation and/or reduce adsorption. Example surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, (sold under the trademark Tween 20™) and polysorbate 80 (sold under the trademark Tween 80™). Examples of suitable polyethylene-polypropylene copolymers are those sold under the names Pluronic® F68 or Poloxamer 188™. Examples of suitable Polyoxyethylene alkyl ethers are those sold under the trademark Brij™. Example concentrations of surfactant may range from about 0.001% to about 1% w/v.

A lyoprotectant may also be added in order to protect the conjugate against destabilizing conditions during a lyophilization process. For example, known lyoprotectants include sugars (including glucose and sucrose); polyols (including mannitol, sorbitol and glycerol); and amino acids (including alanine, glycine and glutamic acid). Lyoprotectants can be included in an amount of about 10 mM to 500 nM.

In some embodiments, the pharmaceutical composition includes a conjugate of the present disclosure, and one or more of the above-identified agents (e.g., a surfactant, a buffer, a stabilizer, a tonicity agent) and is essentially free of one or more preservatives, such as ethanol, benzyl alcohol, phenol, m-cresol, p-chlor-m-cresol, methyl or propyl parabens, benzalkonium chloride, and combinations thereof. In other embodiments, a preservative is included in the formulation, e.g., at concentrations ranging from about 0.001 to about 2% (w/v).

Methods

As summarized above, methods of using the conjugates of the present disclosure are also provided. In certain aspects, the methods of the present disclosure include administering to an individual in need thereof a therapeutically effective amount of any of the conjugates of the present disclosure, or any of the pharmaceutical compositions of the present disclosure.

In certain aspects, the administering modulates an immune pathway in the individual. For example, the administering may modulate an immune pathway selected from an inhibitory immune receptor pathway, a complement pathway, a paired immunoglobulin-like type 2 receptor (PILR) pathway, and a natural-killer group 2, member D protein (NKG2D) pathway. In certain aspects, the target cell includes a ligand on its surface, and the administering results in editing of the ligand by the target cell surface-editing enzyme. The ligand may be edited in any manner described elsewhere herein. According to certain embodiments, the editing of the ligand comprises cleavage of all or a portion of the ligand. As just one example, the ligand may be a sialoglycan, the target cell surface-editing enzyme may be a sialidase, and the editing may include cleavage of a terminal sialic acid residue of the sialoglycan. The sialidase of the conjugate may be a bacterial sialidase, a mammalian neuraminidase, or the like. When the sialidase is a mammalian neuraminidase, the mammalian neuraminidase may be a human neuraminidase, e.g., a human neuraminidase selected from human neuraminidase 1, human neuraminidase 2, human neuraminidase 3, and human neuraminidase 4.

When the administering results in editing of a ligand on the target cell by the target cell surface-editing enzyme, the ligand may be a ligand of an inhibitory immune receptor. In certain aspects, the ligand is a ligand of an inhibitory immune receptor present on an immune cell selected from the group consisting of: a natural killer (NK) cell, a macrophage, a monocyte, a neutrophil, a dendritic cell, a T cell, a B cell, a mast cell, a basophil, and an eosinophil. In some embodiments, the inhibitory immune receptor is a sialic acid-binding Ig-like lectin (Siglec) receptor.

In certain aspects, the methods of the present disclosure include administering the conjugate or pharmaceutical composition to an individual having cancer, e.g., to treat the cancer. Cancers which may be treated according to the methods of the present disclosure include, but are not limited to, any of the cancers set forth in Tables 1 and 2 above. The conjugate may include a targeting moiety (e.g., a therapeutic antibody, such as any of the antibodies set forth in Tables 1, 2, and 3 above) that binds to a tumor-associated cell surface molecule or tumor-specific cell surface molecule on the surface of a cancer cell of the individual. In some embodiments, the cancer cell is a carcinoma cell. According to certain embodiments, the cancer cell is selected from a breast cancer cell, an ovarian cancer cell, a gastric cancer cell, a colon cancer cell, and a cancer cell of any of the cancer types set forth in Tables 1 and 2 above. In certain aspects, the cell surface molecule is human epidermal growth factor receptor 2 (HER2). When the cell surface molecule is HER2, the targeting may be, e.g., an anti-HER2 antibody (e.g., trastuzamab or another suitable anti-HER2 antibody).

In some embodiments, the administering includes administering a conjugate or pharmaceutical composition of the present disclosure, and the conjugate includes a targeting moiety that is an antibody. In certain aspects, the individual in need thereof has cancer, the targeting moiety of the conjugate is an antibody set forth in Table 1, and the methods are for treating (e.g., by enhanced antibody-dependent cellular cytotoxicity (ADCC)) the same or different type of cancer corresponding to the antibody as set forth in Table 1.

In certain aspects, the administering includes administering a conjugate or pharmaceutical composition of the present disclosure, and the conjugate includes a targeting moiety that is an antibody. In some embodiments, the individual in need thereof has cancer, the targeting moiety of the conjugate is an antibody set forth in Table 2, and the methods are for treating (e.g., by enhanced antibody-dependent cellular cytotoxicity (ADCC)) the same or different type of cancer corresponding to the antibody as set forth in Table 2.

In some embodiments, the administering includes administering a conjugate or pharmaceutical composition of the present disclosure, and the conjugate includes a targeting moiety that is an antibody. In certain aspects, the individual in need thereof has cancer, the targeting moiety of the conjugate is an antibody set forth in Table 3, and the methods are for treating the cancer (e.g., by enhanced antibody-dependent cellular cytotoxicity (ADCC)).

In certain aspects, the administering includes administering a conjugate or pharmaceutical composition of the present disclosure, and the conjugate includes a targeting moiety that is an antibody selected from trastuzamab, cetuximab, daratumumab, girentuximab, panitumumab, ofatumumab, and rituximab.

The conjugates of the present disclosure are administered to the individual using any available method and route suitable for drug delivery, including in vivo and ex vivo methods, as well as systemic and localized routes of administration. Conventional and pharmaceutically acceptable routes of administration include intranasal, intramuscular, intra-tracheal, subcutaneous, intradermal, topical application, ocular, intravenous, intra-arterial, nasal, oral, and other enteral and parenteral routes of administration. Routes of administration may be combined, if desired, or adjusted depending upon the conjugate and/or the desired effect. The conjugate may be administered in a single dose or in multiple doses. In some embodiments, the conjugate is administered orally. In some embodiments, the conjugate is administered via an inhalational route. In some embodiments, the conjugate is administered intranasally. In some embodiments, the conjugate is administered locally. In some embodiments, the conjugate is administered ocularly. In some embodiments, the conjugate is administered intracranially. In some embodiments, the conjugate is administered intravenously. In some embodiments, the conjugate is administered by injection, e.g., for systemic delivery (e.g., intravenous infusion) or to a local site.

A variety of individuals are treatable according to the subject methods. Generally such individuals are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the individual is a human.

By "treat" or "treatment" is meant at least an amelioration of the symptoms associated with the pathological condition afflicting the individual, where amelioration is used in a broad sense to refer to at least a reduction in the magnitude of a parameter, e.g., symptom, associated with the pathological condition being treated, such as disease or disorder associated with (e.g., caused by) the target cell or population thereof, where the editing of the surface of the target cell is beneficial. As such, treatment also includes situations where the pathological condition, or at least symptoms associated therewith, are completely inhibited, e.g., prevented from happening, or stopped, e.g. terminated, such that the individual no longer suffers from the pathological condition, or at least the symptoms that characterize the pathological condition.

Dosing is dependent on severity and responsiveness of the disease state to be treated. Optimal dosing schedules can be calculated from measurements of conjugate accumulation in the body of the individual. The administering physician can determine optimum dosages, dosing methodologies and repetition rates. Optimum dosages may vary depending on the relative potency of conjugate, and can generally be estimated based on $EC_{50}$s found to be effective in in vitro and in vivo animal models, etc. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, where the conjugate is administered in maintenance doses, once or more daily, to once every several months, once every six months, once every year, or at any other suitable frequency.

The therapeutic methods of the present disclosure may include administering a single type of conjugate to an individual, or may include administering two or more types of conjugates to an individual (e.g., a cocktail of different conjugates), where the two or more types of conjugates may be designed to edit the surface of the same type or different types of target cells.

In certain aspects, a conjugate of the present disclosure is administered to the individual in combination with a second therapeutic agent as part of a combination therapy. Such administration may include administering the conjugate and the second agent concurrently, or administering the conjugate and the second agent sequentially. In some embodiments, the individual has cancer, and the second therapeutic agent is an anti-cancer agent. Anti-cancer agents of interest include, but are not limited to, anti-cancer antibodies (e.g., any of the antibodies set forth in Tables 1, 2, and 3 above), small molecule anti-cancer agents, or the like.

In some embodiments, the second therapeutic agent is a small molecule anti-cancer agent selected from abiraterone, bendamustine, bexarotene, bortezomib, clofarabine, decitabine, exemestane, temozolomide, afatinib, axitinib, bosutinib, cabozantinib, crizotinib, dabrafenib, dasatinib, erlotinib, gefitinib, ibrutinib, imatinib, lapatinib, nilotinib, pazopanib, ponatinib, regorafenib, ruxolitinib, sorafenib, sunitinib, vandetanib, vemurafenib, enzalutamide, fulvestrant, epirubicin, ixabepilone, nelarabine, vismodegib, cabazitaxel, pemetrexed, azacitidine, carfilzomib, everolimus, temsirolimus, eribulin, omacetaxine, trametinib, lenalidomide, pomalidomide, romidepsin, vorinostat, brigatinib, ribociclib, midostaurin, telotristat ethyl, niraparib, cabozantinib, lenvatinib, rucaparib, granisetron, dronabinol, venetoclax, alectinib, cobimetinib, panobinostat, palbociclib, talimogene laherparepvec, lenvatinib, trifluridine and tipiracil, ixazomib, sonidegib, osimertinib, rolapitant, uridine triacetate, trabectedin, netupitant and palonosetron, belinostat, ibrutinib, olaparib, idelalisib, and ceritinib.

In certain aspects, the second therapeutic agent is an immune checkpoint inhibitor. Immune checkpoint inhibitors of interest include, but are not limited to, inhibitors (e.g., antibodies) that target PD-1, PD-L1, CTLA-4, TIM3, LAG3, or a member of the B7 family.

According to certain embodiments, the conjugate and the second therapeutic agent are administered according to a dosing regimen approved for individual use. In some embodiments, the administration of the second therapeutic agent permits the conjugate administered to the individual to be administered according to a dosing regimen that involves one or more lower and/or less frequent doses, and/or a reduced number of cycles as compared with that utilized when the conjugate is administered without administration of the second therapeutic agent. In certain aspects, the administration of the conjugate permits the second therapeutic agent administered to the individual to be administered according to a dosing regimen that involves one or more lower and/or less frequent doses, and/or a reduced number of cycles as compared with that utilized when the second therapeutic agent is administered without administration of the conjugate.

In certain aspects, desired relative dosing regimens for agents administered in combination may be assessed or determined empirically, for example using ex vivo, in vivo and/or in vitro models; in some embodiments, such assessment or empirical determination is made in vivo, in a patient population (e.g., so that a correlation is established), or alternatively in a particular individual of interest.

In certain aspects, one or more doses of the conjugate and the second therapeutic agent are administered to the individual at the same time; in some such embodiments, such agents may be administered present in the same pharmaceutical composition. In some embodiments, however, the conjugate and the second therapeutic agent are administered to the individual in different compositions and/or at different times. For example, the conjugate may be administered prior to administration of the second therapeutic agent (e.g., in a particular cycle). Alternatively, the second therapeutic agent may be administered prior to administration of the conjugate (e.g., in a particular cycle). The second agent to be administered may be administered a period of time that starts at least 1 hour, 3 hours, 6 hours, 12 hours, 24 hours, 48 hours, 72 hours, or up to 5 days or more after the administration of the first agent to be administered.

Kits

As summarize above, the present disclosure provides kits. According to certain embodiments, the kits include any of the conjugates or compositions of the present disclosure. The kits find use, e.g., in practicing the methods of the present disclosure. For example, kits for practicing the subject methods may include a quantity of the compositions of the present disclosure, present in unit dosages, e.g., ampoules, or a multi-dosage format. As such, in certain embodiments, the kits may include one or more (e.g., two or more) unit dosages (e.g., ampoules) of a composition that includes a conjugate of the present disclosure. The term "unit dosage", as used herein, refers to physically discrete units suitable as unitary dosages for human and animal subjects, each unit containing a predetermined quantity of the composition calculated in an amount sufficient to produce the desired effect. The amount of the unit dosage depends on various factors, such as the particular conjugate employed, the effect to be achieved, and the pharmacodynamics associated with the conjugate in the subject. In yet other embodiments, the kits may include a single multi dosage amount of the composition.

Components of the kits may be present in separate containers, or multiple components may be present in a single container. A suitable container includes a single tube (e.g., vial), one or more wells of a plate (e.g., a 96-well plate, a 384-well plate, etc.), or the like.

According to certain embodiments, a kit of the present disclosure includes instructions for using the composition to treat an individual in need thereof. The instructions may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., portable flash drive, DVD, CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the means for obtaining the instructions is recorded on a suitable substrate.

The following examples are offered by way of illustration and not by way of limitation.

EXPERIMENTAL

Materials and Methods

PBS buffer, DPBS buffer, DMEM, RPMI-1640 media and heat-inactivated fetal bovine serum were obtained from Corning-Mediatech. X-VIVO 15 serum-free medium was purchased from Lonza. LB agar, 2×YT and Antibiotic-Antimycotic were purchased from Fisher Scientific and 4-12% Bis-Tris gels for SDS-PAGE were purchased from Bio-Rad. Heat-inactivated human male AB serum was purchased from Sigma-Aldrich. Human recombinant IL-2, human recombinant IL-4, and human recombinant IL-13 were purchased from Biolegend. Humanized anti-Her2-IgG with an aldehyde tag was a gift from Catalent Pharma Solutions (Emeryville, CA). Absorbance spectra were measured with a SpectraMax i3x (Molecular Devices). Pierce High-Capacity Endotoxin Removal Spin Columns, Pierce LAL Chromogenic Endotoxin Quantitation Kit and LDH cytotoxicity assay kit were obtained from Thermo Fisher Scientific. Bicyclononyne-N-hydroxysuccinimide ester (BCN-NHS) and aminooxy-tetraethyleneglycol-azide (aminooxy-TEG-N3) were purchased from Berry & Associates, Inc. Dibenzocyclooctyne-tetrapolyethyleneglycol-maleimide (DBCO-PEG4-Maleimide) was purchased from Click Chemistry Tools. 2'-(4-Methylumbelliferyl)-α-D-N-acetylneuraminic acid (MuNeuNAc) was obtained from Biosynth International Inc. All other chemicals were purchased from Sigma-Aldrich and used without further purification.

The following antibodies and recombinant proteins were used: Human recombinant Siglec-7-Fc chimera, Siglec-9-Fc chimera, NKG2D-Fc chimera proteins, AF488-labeled anti-Siglec-7 mAb (clone 194211) and blocking anti-NKG2D mAb (clone 149810) were purchased from R&D Systems. Fluorescein isothiocyanate (FITC)-labeled *Sambucus nigra* (SNA) lectin was obtained from EY Laboratories. AF647-labeled anti-Her2 mAb (clone 24D2), AF647-labeled anti-CD16 mAb (clone 3G8), AF647-labeled anti-CD56 mAb (clone HCD56), blocking anti-Siglec-7 mAb (clone S7.7), blocking anti-Siglec-9 mAb (clone K8) were obtained from Biolegend. TRITC-labeled anti-Fc mAb was purchased from Jackson Immunoresearch. FITC-labeled anti-CD3 mAb (clone BW264/56) was purchased from Miltenyi Biotec. Humanized anti-Her2-IgG with C-terminal aldehyde-tag was a gift from Catalent Pharma Solutions (Emeryville, CA).

Cell Lines and Cell Culture:

Breast cancer cells SKBR3, HCC-1954, MDA-MB-453, ZR-75-1, BT-20, MDA-MB-231, and MDA-MB-468 were obtained from American Type Culture Collection (ATCC). SKBR3, HCC-1954, ZR-75-1, and MDA-MB-468 were maintained in RPMI-1640 medium supplemented with 10% heat-inactivated fetal bovine serum, plus 0.4% Antibiotic-Antimycotic and L-glutamine (300 mg/L). MDA-MB-453, BT-20, and MDA-MB-231 were maintained in DMEM medium supplemented with 10% heat-inactivated fetal bovine serum, plus 0.4% Antibiotic-Antimycotic, L-glucose (4.5 g/L), L-glutamine (584 mg/L) and sodium pyruvate (110 mg/L).

Figure 16:
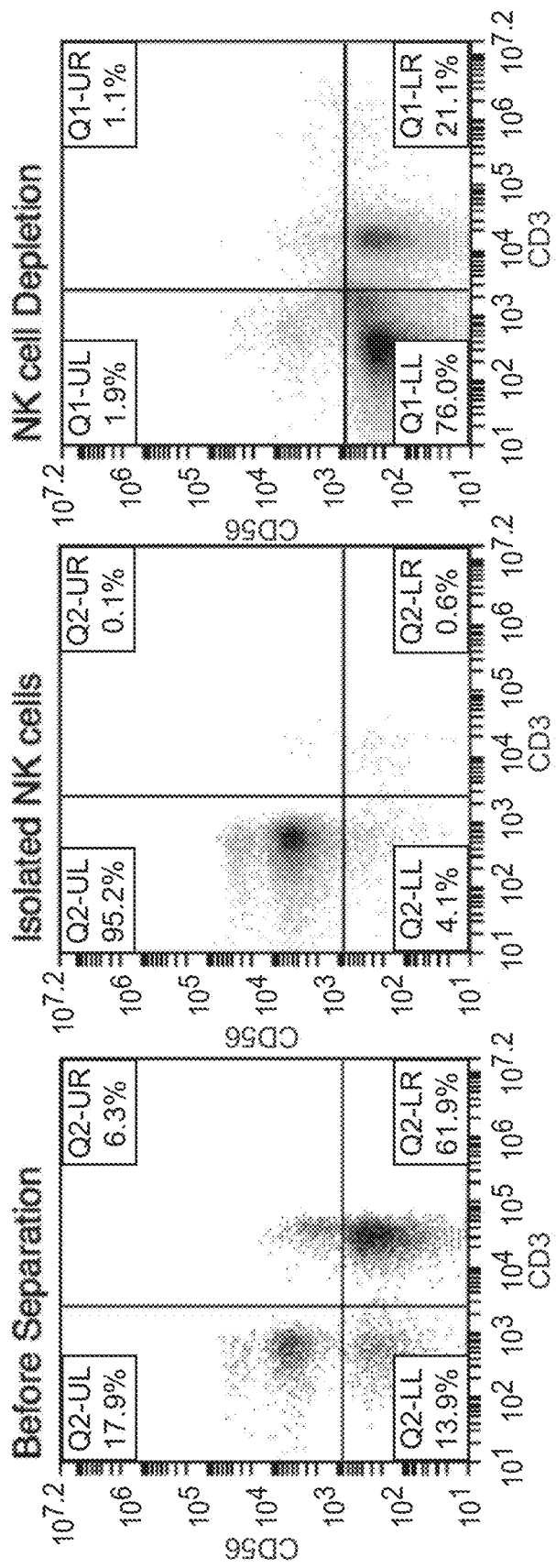
FIG. 16 depicts flow cytometry data analyzing CD56 and CD3 markers on leukocytes.

Peripheral blood mononuclear cells (PBMCs) were obtained from healthy blood bank donors and were isolated using Ficoll-Paque (GE Healthcare Life Sciences, GE-17-1440-02) density gradient separation. NK cells were isolated from PBMCs by negative selection using the MACS NK cell isolation kit (Miltenyi Biotec, 130-092-657) and LS columns (Miltenyi Biotec, 130-042-401) according to the manufacturer's protocol and cultured in X-sVIVO 15 supplemented with 5% heat-inactivated human male AB serum (Sigma-Aldrich), and 100 ng/mL recombinant human interleukin-2 (IL-2) (Biolegend) overnight before using. NK cell enrichment was verified by flow cytometry to result in >95% CD56+/CD3− cells (see, FIG. 16). Monocytes were isolated from PBMCs using the Pan Monocyte isolation kit (Miltenyi Biotec 130-096-537). CD16+ monocytes were isolated from PBMCs using the CD16+ Monocyte isolation kit (Miltenyi Biotec 130-091-765). After isolating fresh PBMCs, M1 and M2-polarized macrophages were acquired by first plating freshly isolated PBMCs in serum-free RPMI a T75 flask (Fisher Scientific 1368065) at 37° C. in 5% $CO_2$ for 2 hours, then removing media and washing cells three times with phosphate buffered saline (PBS +Ca +Mg) to isolate monocytes. M1-polarized cells were generated by incubating remaining monocytes with 50 ng/mL recombinant human GM-CSF (PeproTech 300-03) for 6 days in RPMI+20% heat inactivated fetal bovine serum, followed by 4 days incubation with 100 ng/mL bacterial Lipopolysaccharide (Invivogen tlrl-3pelps) and 20 ng/mL recombinant human IFNγ (PeproTech 300-02BC) in RPMI with 10% heat-inactivated fetal bovine serum. M2-polarized macrophages were generated by incubating monocytes with 50 ng/mL recombinant human M-CSF (PeproTech 300-25) for 6 days in RPMI+20% heat inactivated fetal bovine serum followed by 4 days incubation with 20 ng/mL recombinant human IL-13 (carrier-free) (Biolegend 571102) and 100 ng/mL recombinant human IL-4 (carrier-free) (Biolegend 574004). Human γδ T cells were isolated from PBMCs by negative selection with the EasySep™ Human Gamma/Delta T Cell Isolation Kit (Stemcell Tech 19255).

FACS Analysis:

Cells were incubated with sialidase, anti-Her2-IgG, anti-Her2-IgG-Sia, or PBS control for 1 hour at 37° C. After three washes with PBS, cells were resuspended in cold PBS with 0.5% bovine serum albumin (BSA) containing the probe of choice: antibody, receptor-Fc fusion protein with secondary anti-Fc antibody pre-complexed in solution, or FITC-labeled SNA lectin. Cells and antibodies/fusion proteins were incubated for 30 mins at 4° C. in the dark. After three washes with PBS with 0.5% BSA, the cells were brought up in PBS with 0.5% BSA then analyzed by flow cytometry. All flow cytometry data was analyzed using FlowJo v. 10.0 (Tree Star).

Expression and Purification of Sialidases:

Escherichia coli C600 transformed with plasmid pCVD364 containing the Vibrio cholerae sialidase gene was a gift from Prof. Eric R. Vimr, University of Illinois, Urbana-Champaign. Cells were grown in 2×YT media, supplemented with ampicillin (100 µg/mL) at 37° C. for 12 hours. After incubation, the cells were harvested by centrifugation at 4, 700×g for 10 min. And the pellet was resuspended in osmotic shock buffer (20% sucrose, 1 mM EDTA, 30 mM Tris-HCl, pH 8.0) and shaken gently for 10 min at room temperature. The cells were collected by centrifugation (9,000×g for 10 min) and the pellets were resuspended in ice-cold pure water. After a 10 min incubation at 4° C., the supernatant was obtained by centrifugation at 9,000×g for 10 min. To purify the protein, the sample was further concentrated using an Amicon ultrafiltration device (membrane molecular mass cutoff, 30,000 Da), reconstituted in 0.02 M Tris-HCl buffer (pH 7.6), and loaded onto a HitrapQ-HP anion-exchange column (GE Healthcare Life Sciences, 17-1154-01). The protein was eluted with a gradient of NaCl in 0.02 M Tris-HCl buffer (pH 7.6) at a flow rate of 5 mL/min. The protein fractions with expected molecular mass as determined by SDS-PAGE stained with Coomassie brilliant blue were collected and pooled. Endotoxins were removed using high-capacity endotoxin removal spin kit (Thermo Fisher Scientific, 88275) and the endotoxin concentration of the sample was determined by LAL chromogenic endotoxin quantitation kit (Thermo Fisher Scientific, 88282).

The Salmonella typhimurium sialidase gene was cloned into a pET151 vector with an N-terminal Hexahisitidine tag and C-terminal aldehyde tag (SLCTPSRGS) and transformed into BL21(DE3) competent E. coli (NEB C2527H). Cells were grown in 2×YT media, supplemented with ampicillin (100 µg/mL) at 37° C. for until they reached an optical density of 0.6, then 0.3 mM IPTG was added and the cells were grown at 37° C. shaking for 16 hours. After incubation, the cells were harvested by centrifugation at 4, 700×g for 10 min. And the pellet was resuspended in 50 mL lysis buffer (phosphate buffered saline (Fisher Scientific MT1040cv)+ 150 mM NaCl+10 mM imidazole. A protease inhibitor tablet (Sigma 5892970001) and 1 µL of nuclease (Thermo Scientific-Pierce 88702) was added and the cells in lysis buffer were incubated at 4° C. shaking for 2 hours. Cells were lysed via homogenizer and purified using nickel-NTA resin (Thermo Fisher 88221) with 250 mM imidazole elution. The protein fractions with expected molecular mass as determined by SDS-PAGE stained with Coomassie brilliant blue were collected and pooled. Endotoxins were removed using high-capacity endotoxin removal spin kit (Thermo Fisher Scientific, 88275) and the endotoxin concentration of the sample was determined by LAL chromogenic endotoxin quantitation kit (Thermo Fisher Scientific, 88282).

Activity Assay of Sialidases Using MuNeuNAc:

5 µL of sialidase (30-60 nM in DPBS buffer with $Ca^{2+}$ and $Mg^{2+}$, pH 7.0) was added to 50 µL solution containing 0.1 mM 2'-(4-methylumbelliferyl)-α-D-N-acetylneuraminic acid (MuNeuNAc, Biosynth International Inc.) in DPBS buffer with $Ca^{2+}$ and $Mg^{2+}$ (pH 7.0). After incubation for 10 min at 37° C., the mixture was diluted with 150 µL of 0.1 M glycine-NaOH buffer, pH 10.4. Fluorescence was read with a fluorescence spectrophotometer (excitation 360 nm; emission 440 nm). Activity is reported as U/mg, where a unit is defined as the amount of enzyme required to release 1 µmol of methylumbelliferone per minute in DPBS buffer, pH 7.

Preparation of Anti-Her2-IgG-Sia:

Purified Vibrio cholerae sialidase (2 mg/mL in DPBS buffer with $Ca^{2+}$ and $Mg^{2+}$, pH 7.0) was reacted with 12 equivalent of bicyclononyne-N-hydroxysuccinimide ester (BCN-NHS) at 4° C. overnight. Excess linker was removed using a PD-10 Desalting Column (GE Healthcare Life Sciences, 17-0851-01). The degree of labeling was determined by ESI-MS (see, FIG. 6B). Humanized anti-Her2-IgG with C-terminal aldehyde-tag was produced as described previously. Anti-Her2-IgG-Sia was prepared by first coupling anti-Her2-IgG with C-terminal aldehyde-tag (120 µM) to aminooxy-tetraethyleneglycol-azide (aminooxy-TEG-$N_3$) (10 mM) in 100 mM ammonium acetate buffer, pH 4.5, at 37° C. for 10 days, followed by buffer-exchange into DPBS buffer with $Ca^{2+}$ and $Mg^{2+}$ (pH 7.0) using a PD-10 Desalting Column (GE Healthcare Life Sciences, 17-0851-01). The resulting conjugate was then coupled to labeled sialidase at 1:28 molar ratio at 120 mg/mL total protein concentration in DPBS buffer with $Ca^{2+}$ and $Mg^{2+}$ (pH 7.0). After a 3 day incubation at room temperature, anti-Her2-IgG-Sia was purified by size exclusion chromatography Superdex 200. The purified product was analyzed by SDS-PAGE gel and ESI-MS.

Purified Salmonella typhimurium sialidase (3 mg/mL in DPBS buffer with $Ca^{2+}$ and $Mg^{2+}$, pH 7.0) was reacted with 20 equivalent of DBCO-PEG4-Maleimide at 4° C. overnight. Excess linker was removed using a PD-10 desalting column (GE Healthcare Life Sciences, 17-0851-01). The degree of labeling was determined by ESI-MS (see FIG. 6B). Humanized anti-Her2-IgG with C-terminal aldehyde-tag was produced as described previously. Anti-Her2-IgG-Sia was prepared by first coupling anti-Her2-IgG with C-terminal aldehyde-tag (120 µM) to aminooxy-tetraethyleneglycol-azide (aminooxy-TEG-$N_3$) (10 mM) in 100 mM ammonium acetate buffer, pH 4.5, at 37° C. for 10 days, followed by buffer-exchange into DPBS buffer with $Ca^{2+}$ and $Mg^{2+}$ (pH 7.0) using a PD-10 Desalting Column (GE Healthcare Life Sciences, 17-0851-01). The resulting conjugate was then coupled to labeled sialidase at 1:14 molar ratio at 25 mg/mL total protein concentration in DPBS buffer with $Ca^{2+}$ and $Mg^{2+}$ (pH 7.0). After a 3 day incubation at room temperature, anti-Her2-IgG-Sia was purified by size exclusion chromatography Superdex 200. The purified product was analyzed by SDS-PAGE gel and ESI-MS.

Cell Cytotoxicity Assay:

Antibody-dependent cellular cytotoxicity (ADCC) was analyzed by measuring lactate dehydrogenase (LDH) release from breast cancer cells as a result of ADCC activity of peripheral blood mononuclear cells (PBMCs), NK cells, monocytes, CD16+ monocytes, M1 macrophages, or M2 macrophages. Tumor cells (target cells) were co-incubated with PBMCs, NK cells, monocytes, or macrophages (effector cells) at various effector/target (E/T) ratios in the presence or absence of sialidase or mAbs in triplicate. In a typical experiment, 100 µL of effector cells were added to a V-bottom 96-well plate containing 100 µL of target cells at $2\times10^5$ cells/mL. After 4 hours, supernatants were collected, and LDH release was measured using a LDH cytotoxicity assay kit (Thermo Fisher Scientific, 88954) according to the manufacturer's protocol. The absorbance at 490 nm was measured with a SpectraMax i3x (Molecular Devices). Specific lysis was calculated as 100×(experimental−effector cells spontaneous release−target cells spontaneous release)/(target cells maximum release−target cells spontaneous release).

Fluorescence Microscopy:

For visualization of HER2-specific enzymatic activity of the conjugate: cells were incubated with various concentrations of anti-Her2-IgG-Sia in PBS buffer for 1 hour at 37° C. After washes with PBS, cells were then fixed with 4% formaldehyde at room temperature for 20 min. The fixed cells were washed with 0.5% BSA in PBS three times, followed by blocking in PBS with 0.5% BSA for 1 hour. Cells were incubated with FITC-labeled SNA (1:100) and AF647-labeled anti-Her2 antibody (1:100) in 0.5% BSA in PBS for 30 min at room temperature in the dark with gentle shaking. After washing thrice with 0.5% BSA in PBS, DAPI (1:1250 dilution from a 10 mM stock) was added right before imaging with a Nikon A1R+ Resonant Scanning Confocal Microscope.

For visualization of NK-tumor cell synapses: tumor cells were incubated with 6 nM anti-Her2-IgG or 6 nM anti-Her2-IgG-Sia in PBS buffer for 1 hour at 37° C. Freshly isolated NK cells were added to tumor cells at an E/T ratio of 2:1 and incubated together for 15 min at 37° C. After washing with PBS, cells were fixed with 4% formaldehyde in PBS for 20 min at room temperature. The fixed cells were washed with 0.5% BSA in PBS three times, followed by blocking in PBS with 0.5% BSA for 1 hour. Cells were incubated with a mixture of AF488-labeled anti-Siglec 7 (1:100), TRITC-labeled anti-Fc (1:400), and AF647-labeled anti-CD16 (1:100) in PBS buffer for 30 min at room temperature in the dark with gentle shaking. After washing thrice with 0.5% BSA in PBS, DAPI (1:1250 dilution from a 10 mM stock) was added right before imaging with a Nikon A1R+ Resonant Scanning Confocal Microscope.

Statistical Analysis:

Statistical analyses were conducted with Prism 6. Data are shown as mean±SD of triplicate experiments, and significance was determined using a t-test, unless otherwise noted. **=p<0.005, *=p<0.05, and a p value >0.05 was considered significant.

Introduction

When sufficiently abundant, glycans terminating in sialic acid residues create a signature of "healthy self" that suppresses immune activation via several pathways—through recruitment of complement factor H and subsequent down-regulation of the alternative complement cascade, for example, and by recruitment of immunosuppressive sialic acid-binding Ig-like lectins (Siglecs) found on most types of leukocytes to the immunological synapse. Sialylation status plays an important role in a cell's ability to trigger or evade immunological recognition.

Upregulation of sialylated glycans has been correlated with poor prognosis and decreased immunogenicity of tumors. Hypersialylation of cancer cells may contribute to evasion of immune surveillance by NK cells, the major mediators of antibody-dependent cell-mediated cytotoxicity (ADCC). Dense populations of sialylated glycans can recruit NK cell-associated Siglec-7 and/or Siglec-9 to the immune synapse (FIG. 1). Like PD-1, these Siglecs possess a cytosolic immunoreceptor tyrosine-based inhibitory (ITIM) motif that mediates suppression of signals from activating NK cell receptors (FIG. 1). Engineered hypersialylation of tumor targets is protective from innate NK cell killing as well as ADCC in a Siglec-7-dependent manner. Likewise, enzymatic removal of sialic acids by treatment of tumor cells with sialidase potentiates NK cell-mediated killing, as does inhibition of Siglec-7 or -9 with blocking antibodies. Sialylation of cancer cell glycans also disrupts the interaction of the NK-activating receptor, natural killer group 2D (NKG2D), with its cognate ligands, thus reducing NK-activating signals from tumor cells (FIG. 1). Conversely, removal of cell-surface sialic acids enhances NK cell activation by increasing NKG2D-ligand binding. Thus, during the microevolutionary process of tumor progression, hypersialylation provides a selective advantage by reducing NK activating signals while enhancing NK inhibitory signals emanating from the immune synapse.

An immune evasion strategy targeting NK-activating receptors and NK-inhibitory receptors using sialic acids is schematically illustrated in FIG. 1. In sialic acid-overexpressing cancer cells, hypersialylated glycans interact with NK inhibitory receptors, leading to inhibition of NK cells activation. Removal of cell-surface sialic acids by antibody-sialidase conjugate abolishes the interaction of sialylated glycans and NK-inhibitory receptors, and increases the binding between NK-activating receptor and its ligands, thereby enhancing the tumor cell susceptibility to NK cell-mediated ADCC.

It was reasoned that tumor-specific desialylation could be a powerful intervention that potentiates tumor cytolysis by NK cells. It is reported here that an antibody-enzyme conjugate (AEC) can selectively edit the tumor cell glycocalyx and potentiate NK cell killing by ADCC, a therapeutically important mechanism harnessed by many antibody cancer drugs. A recombinant sialidase was chemically fused to the HER2-targeting therapeutic monoclonal antibody trastuzumab. The antibody-sialidase conjugate desialylated tumor cells in a HER2-dependent manner, destroyed ligands for inhibitory Siglecs while enhancing NKG2D binding, and amplified NK cell killing compared to trastuzumab alone (FIG. 1).

Example 1—Suitability of *V. cholera* and *S. typhimurium* Sialidases

To identify suitable sialidases for the trastuzumab AEC, a panel of enzymes were expressed and purified as described previously (FIGS. 3A and B) and the *Vibrio cholera* and *Salmonella typhimurium* sialidases were identified as well suited for this purpose. *V. cholerae* and *S. typhimurium* sialidases were expressed and purified as described previously. The purity of protein was determined by SDS-PAGE gel and ESI-MS (FIG. 2B, 2E, and FIG. 3B, and FIG. 7A, 7F). Approximately 15 mg of enzymes were purified from 1 liter of cultured cells, with an in vitro hydrolytic activity of more than 10 U/mg for *V. cholerae* and 114 for *S. typhimurium* as measured with the fluorogenic substrate 2'-(4-methylumbelliferyl)-α-D-N-acetylneuraminic acid (Mu-NeuNAc) as previously reported, where a unit is defined as the amount of enzyme required to release 1 μmol of methylumbelliferone per minute in DPBS buffer, pH 7. To determine if *V. cholerae* sialidase could efficiently remove sialic acids from cell-surface glycans, its effects on cell surface labeling was tested with FITC-labeled *Sambucus nigra* agglutinin (SNA). As well, the effects of *V. cholerae* treatment on cell labeling were evaluated with receptor-Fc chimeras comprising the ectodomains of Siglec-7, Siglec-9 or NKG2D. Desialylation of various tumor cell lines by sialidase at 37° C. for 1 hour significantly reduced binding of SNA as well as Siglec-7-Fc and Siglec-9-Fc chimeras (FIG. 4). With a decrease in SNA binding, an increase in binding capacity of NKG2D-Fc chimera was observed for most breast cancer cell lines after sialidase treatment (FIG. 4D).

Figure 2:
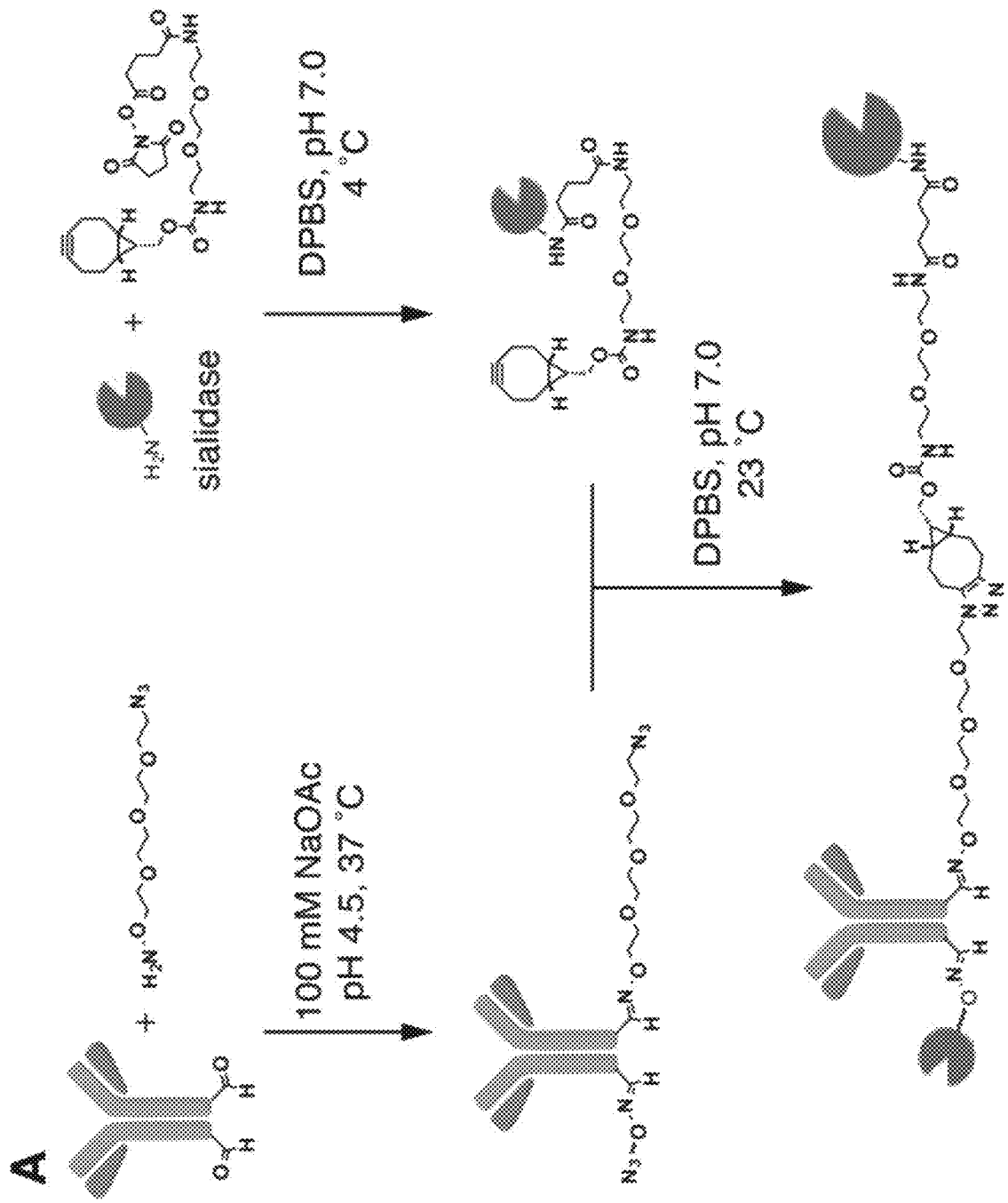
FIG. 2 depicts the preparation of antibody-sialidase conjugates and their electrophoretic and ESI-MS analysis.
Figure 2:
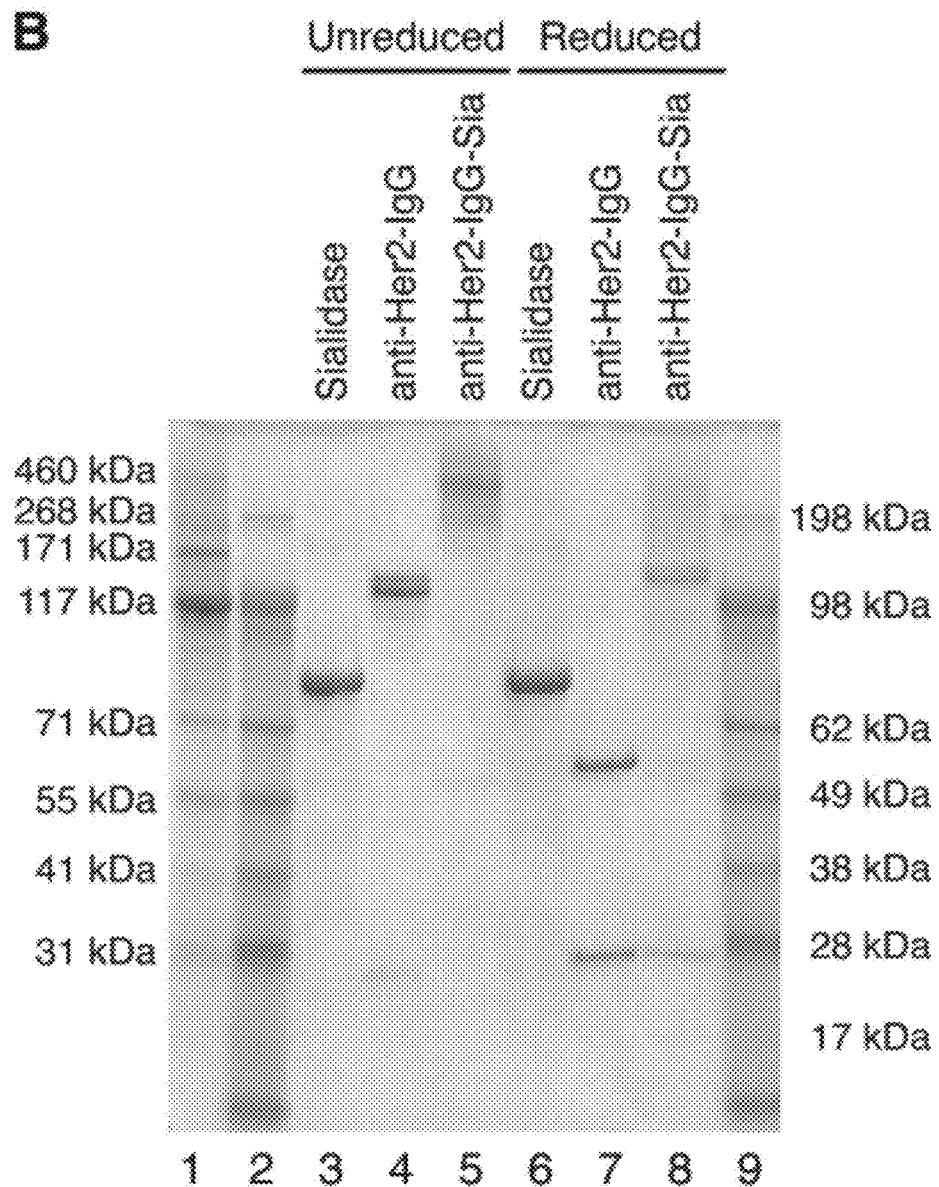
Figure 2:
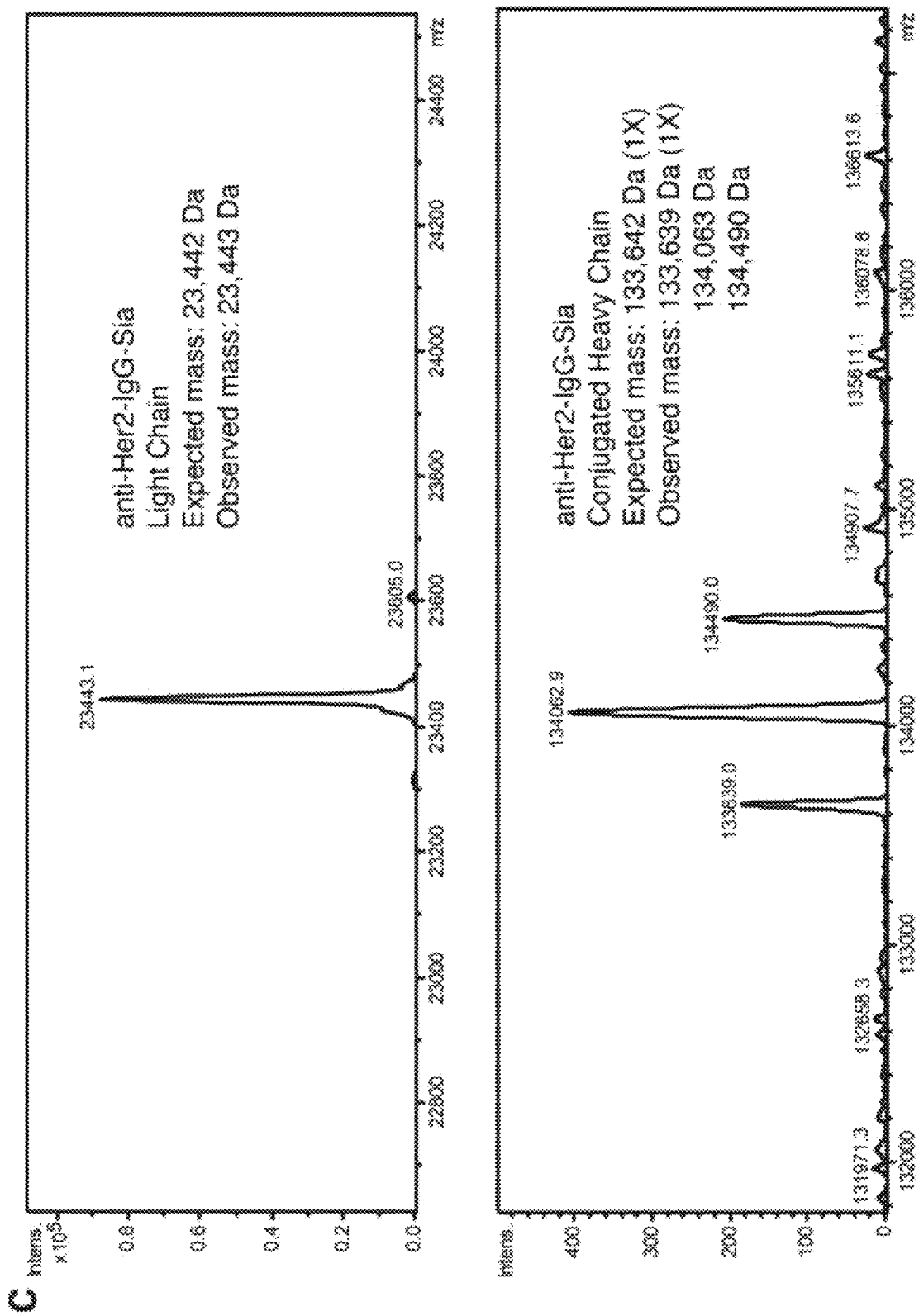
Figure 2:
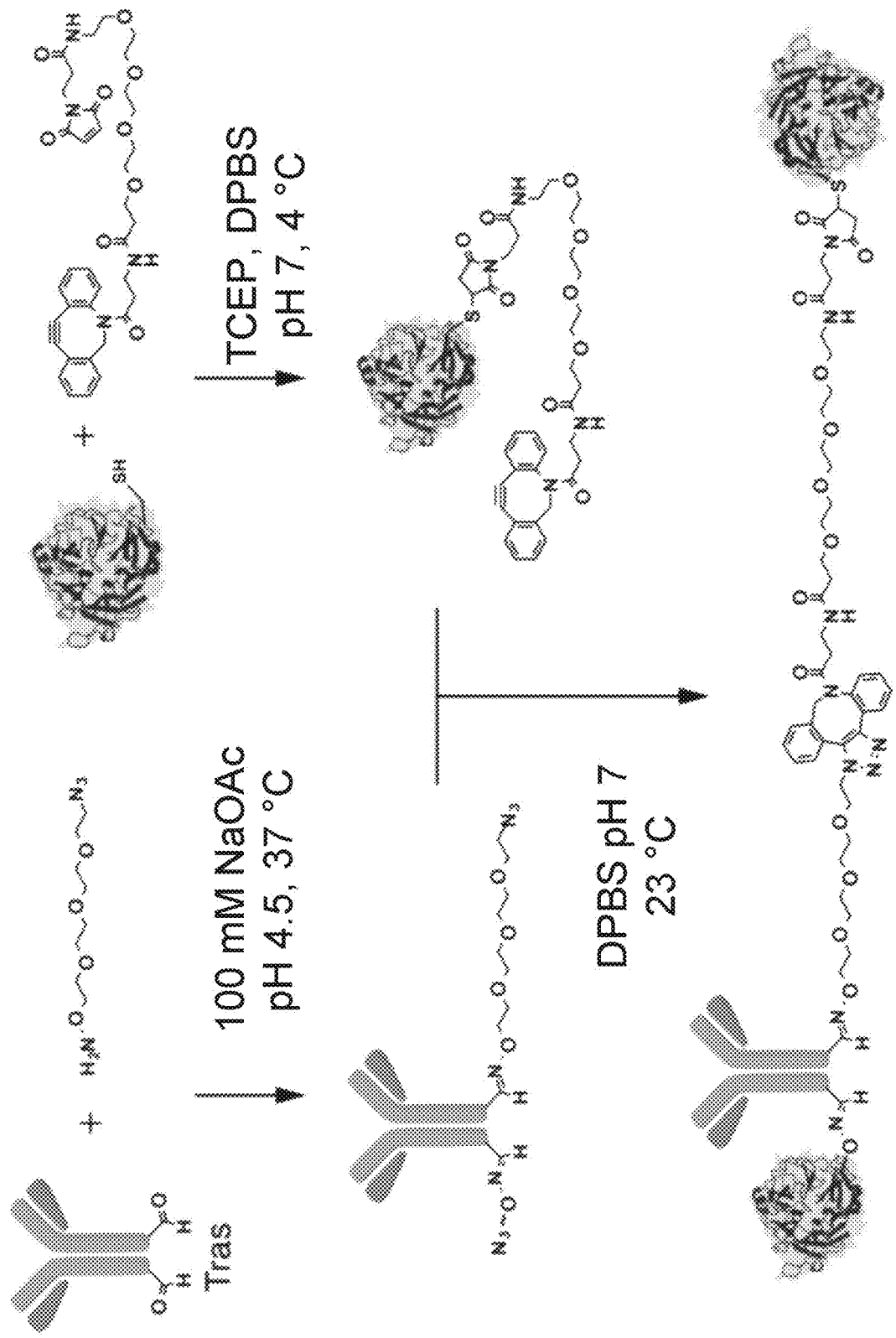
Figure 2:
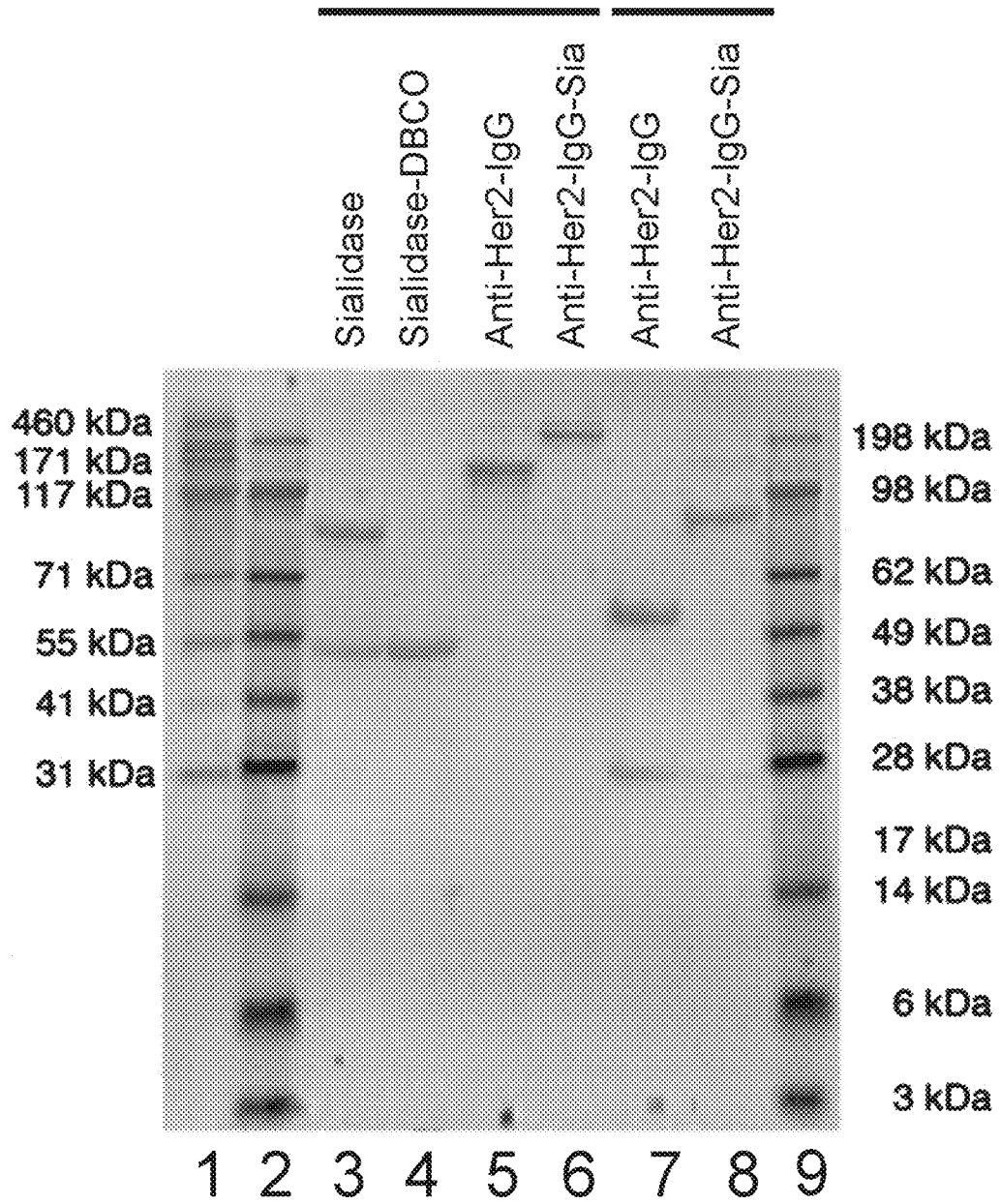
Figure 2:
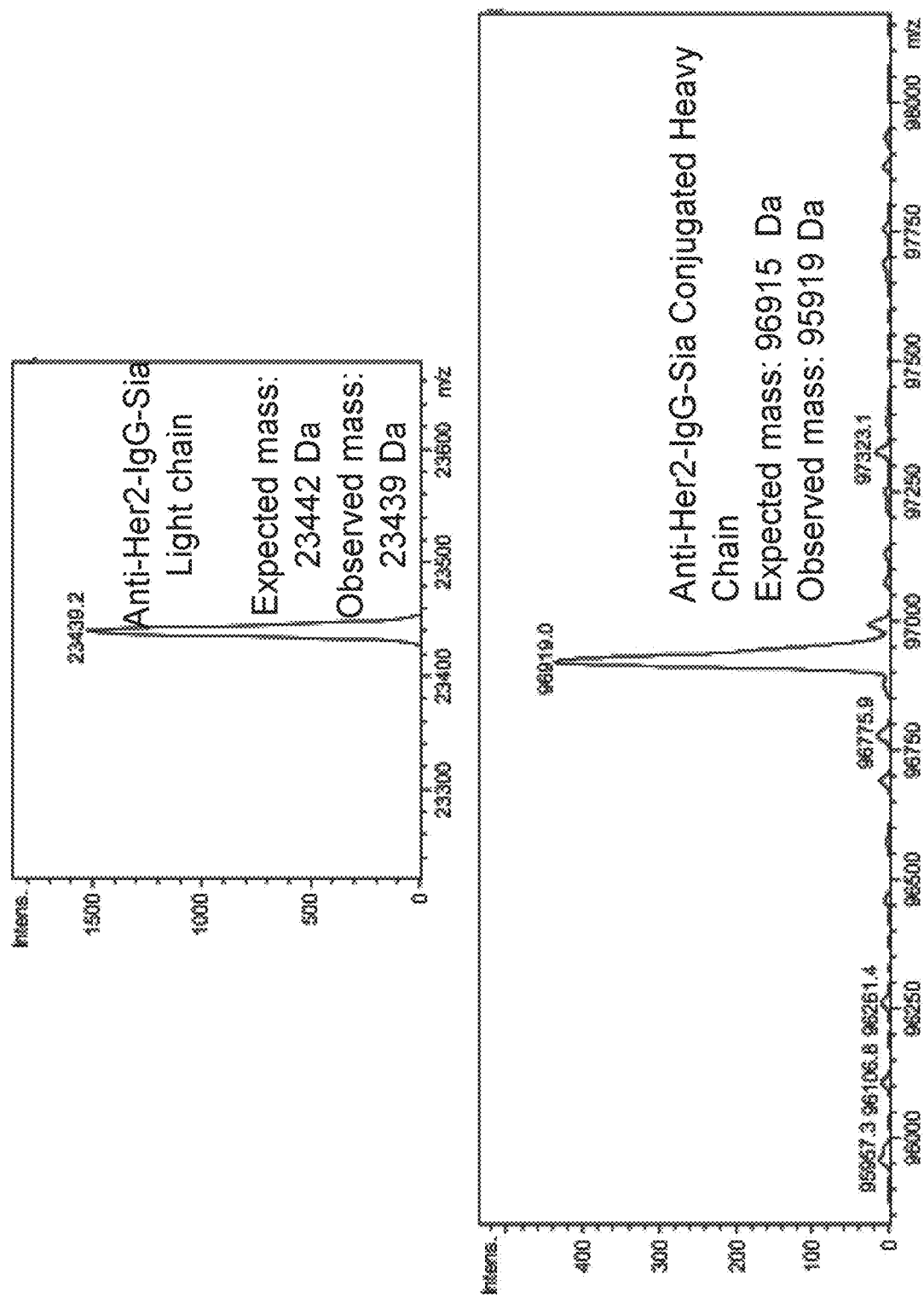

Preparation and characterization of antibody-sialidase conjugates is shown in FIG. 2. FIG. 2A schematically illustrates the preparation of antibody-*Vibrio cholerae* sialidase conjugates. FIG. 2B shows SDS-PAGE analysis of sialidase, trastuzumab, and sialidase-trastuzumab conjugate under non-reducing (lanes 3, 4, and 5) and reducing conditions (lanes 6, 7, and 8), visualized by coomassie staining. Pre-stained protein ladder: lanes 1, 2, and 9. FIG. 2C shows ESI-MS of antibody sialidase conjugate with *Vibrio cholerae* sialidase. FIG. 2D schematically illustrates the preparation of antibody-*Salmonella typhimurium* sialidase conjugates. FIG. 2E shows SDS-PAGE analysis of sialidase, DBCO-modified sialidase, trastuzumab, and trastuzumab-sialidase conjugate under non-reducing conditions (lanes 3, 4, 5, and 6) and trastuzumab and trastuzumab-sialidase conjugate under reducing conditions (lanes 7 and 8), visualized by coomassie staining. Pre-stained protein ladder: lanes 1, 2, and 9. FIG. 2F shows ESI-MS of antibody-sialidase conjugate with *Salmonella typhimurium* sialidase.

Figure 3:
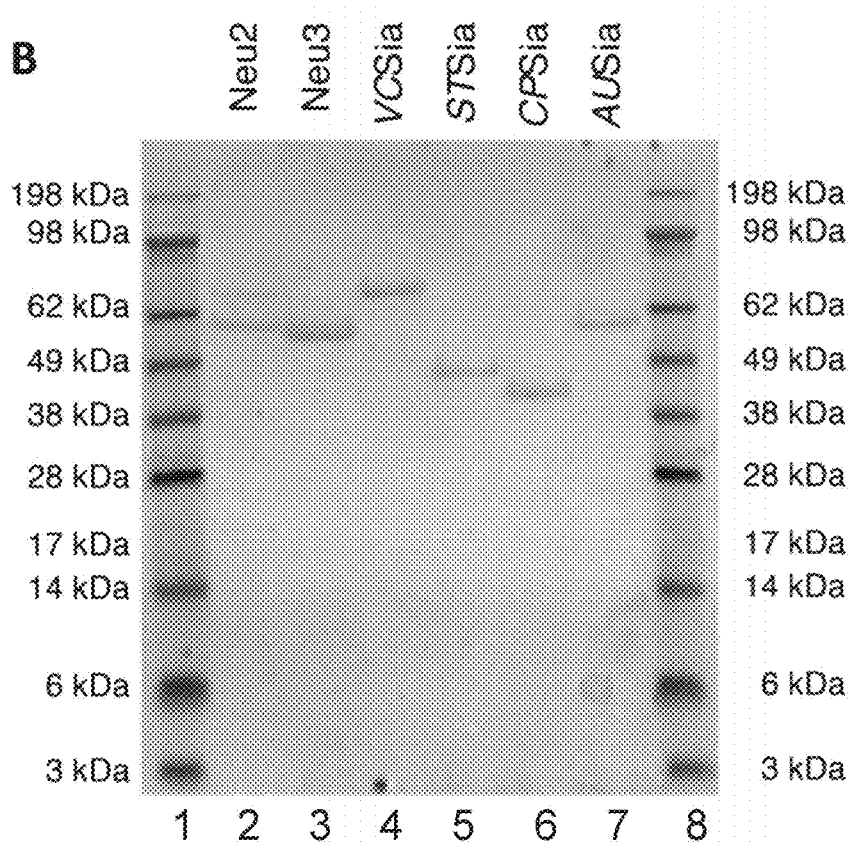
FIG. 3 depicts electrophoretic analysis of sialidases, hydrolysis activities, and flow cytometry and imaging analysis of their activities
Figure 3:
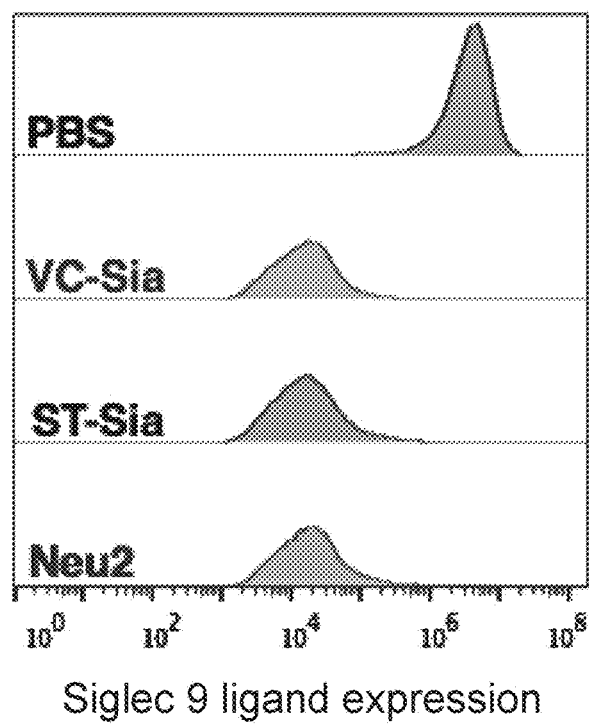
Figure 3:
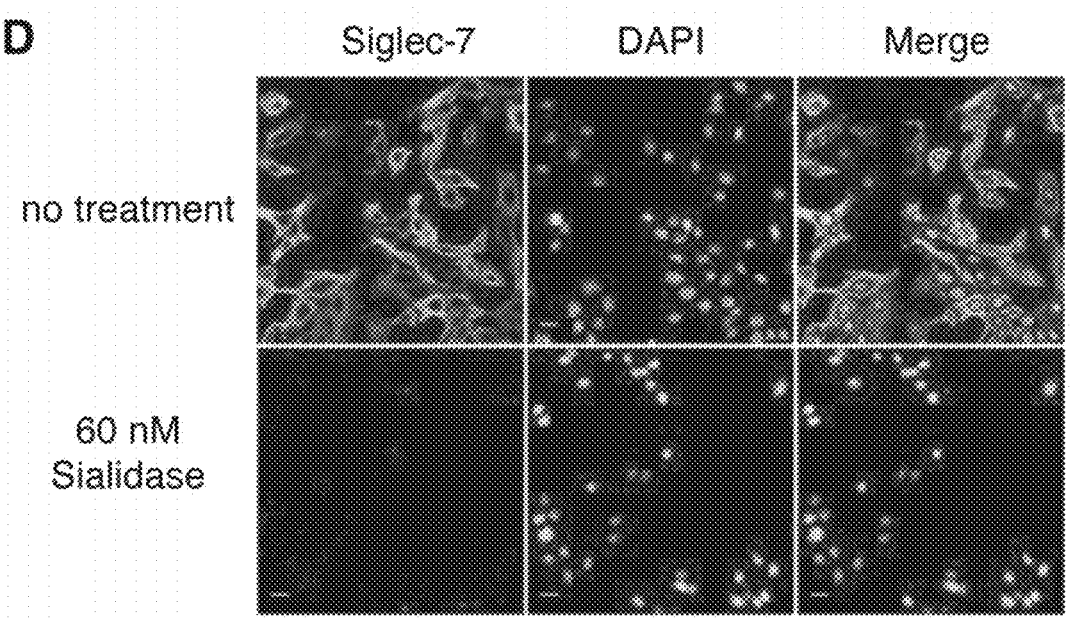
Figure 4:
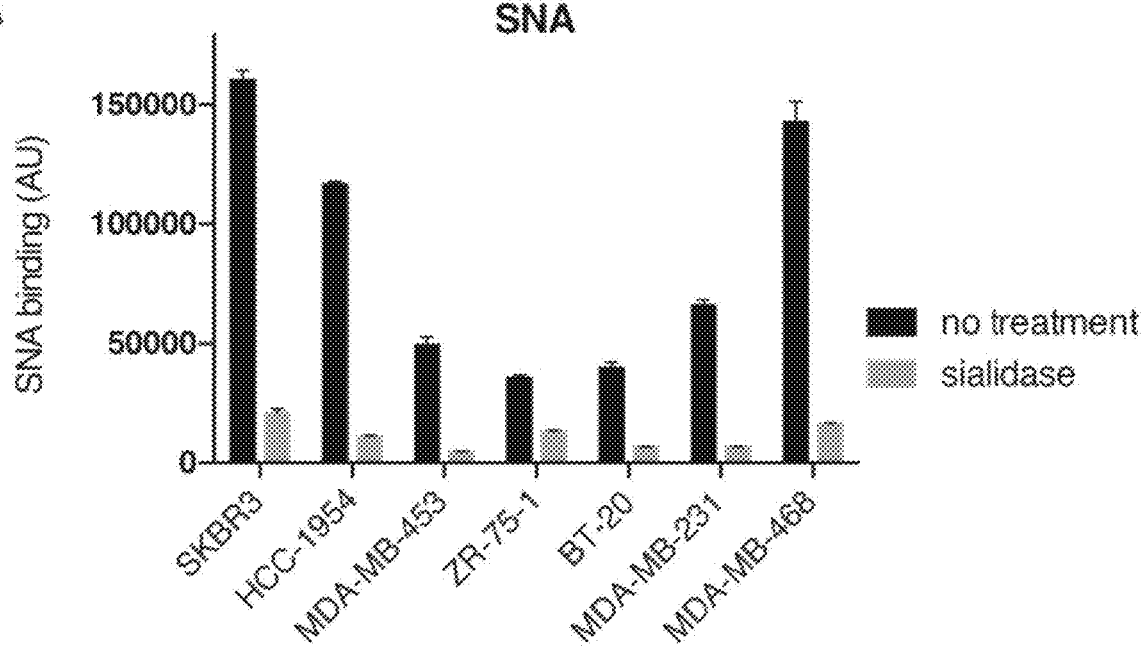
FIG. 4 depicts cell-surface sialylation levels and ligand levels of various receptors with or without sialidase treatment in different breast cancer cell lines.
Figure 4:
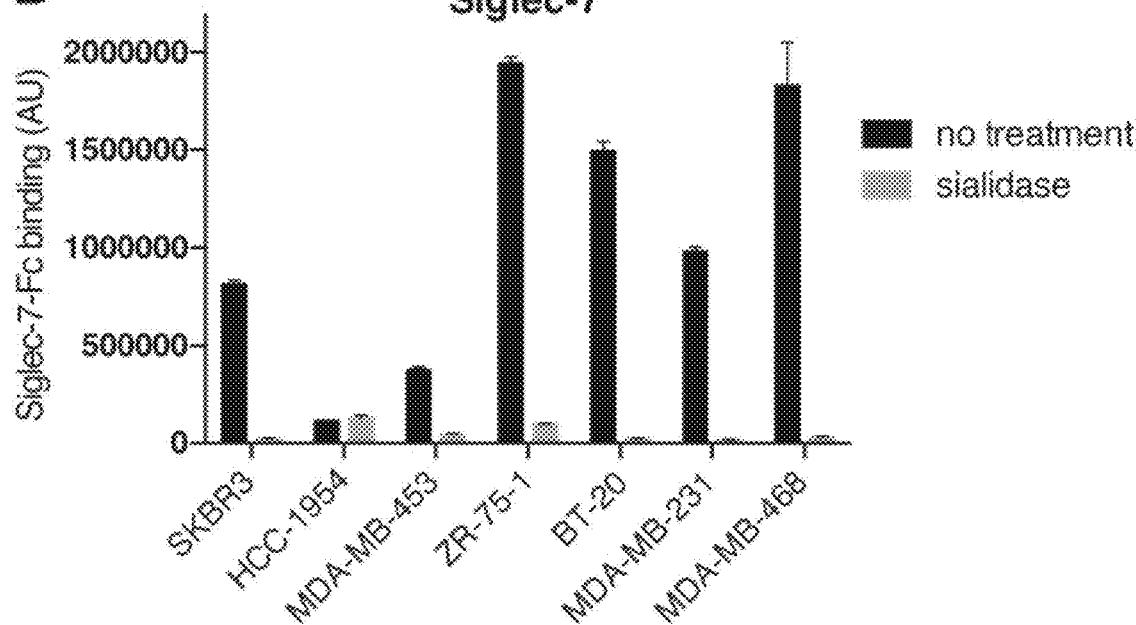
Figure 4:
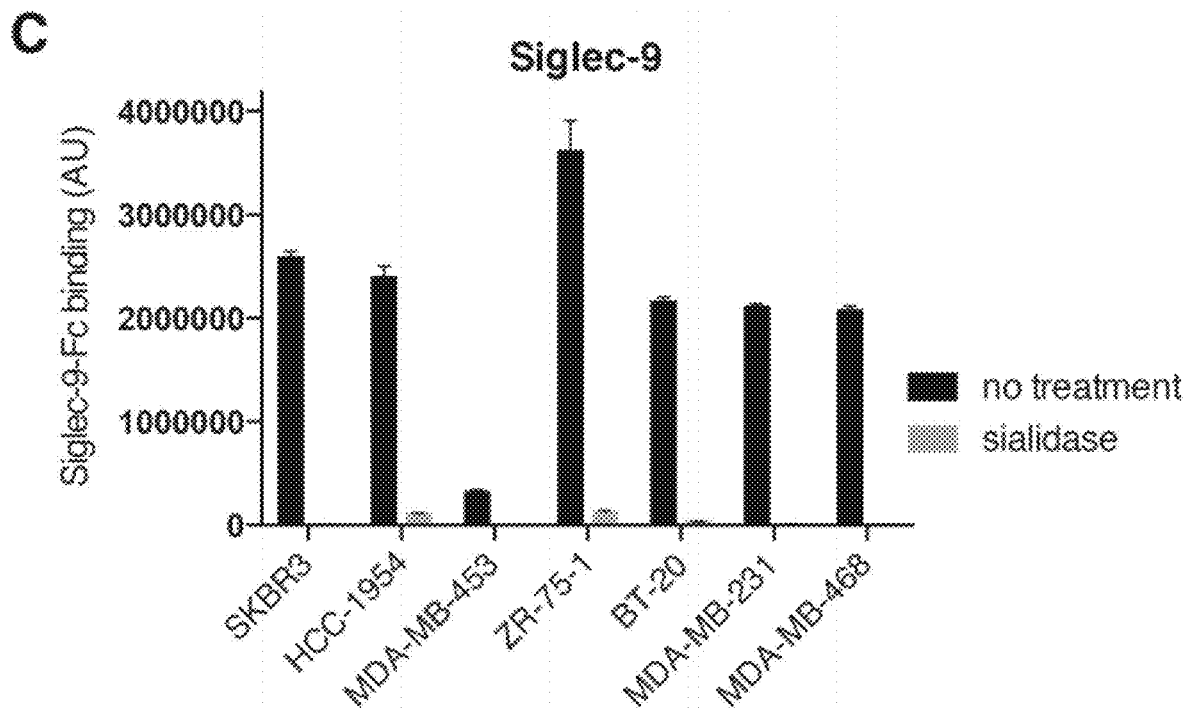
Figure 4:
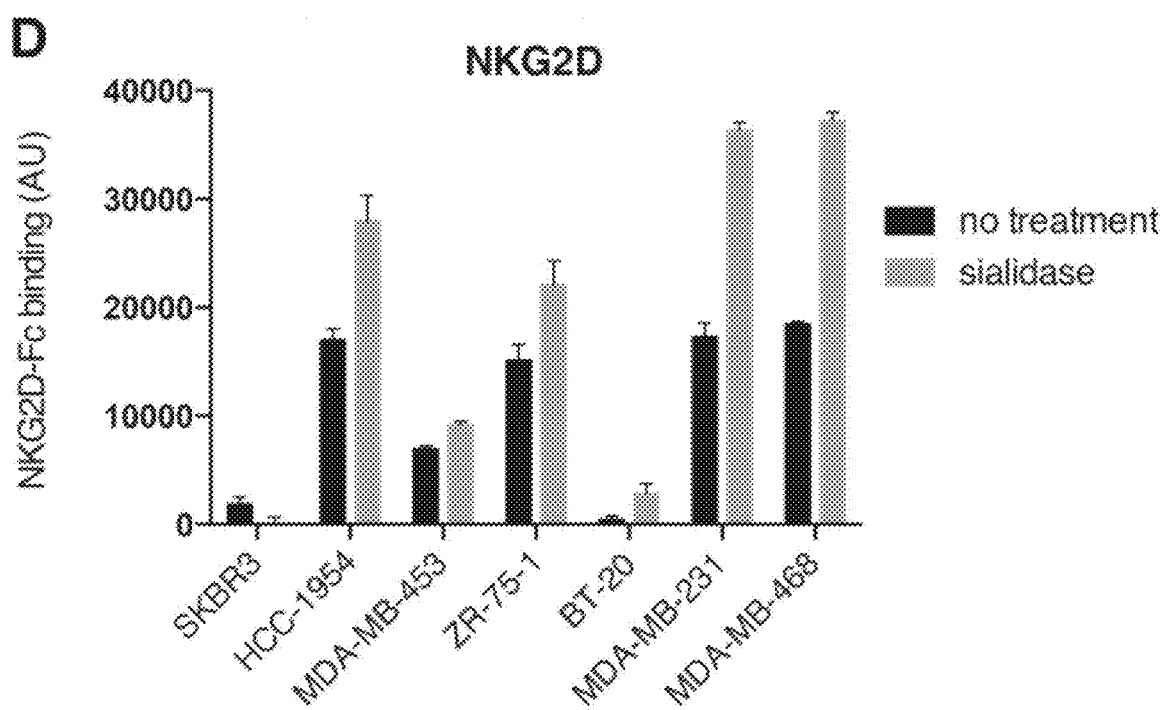

FIG. 3 shows the characterization of a panel of sialidases. FIG. 3A depicts activity of sialidases on the substrate 2'-(4-methylumbelliferyl)-α-D-N-acetylneuraminic acid (MuNeuNAc). SDS-PAGE analysis of wild-type human neuraminidase 2, human neuraminidase 3, *V. cholerae* sialidase, *S. typhimurium* sialidase, *C. perfringens* sialidase, and *A. ureafaciens* sialidase is shown in FIG. 3B, visualized by coomassie staining. FIG. 3C shows flow cytometry of Siglec 9 ligand cleavage by *V. cholerae*, *S. typhimurium*, and human Neuraminidase 2 from ZR-75-1 breast cancer cells. Siglec-7 ligands on BT-20 cells are efficiently removed after treatment with *V. cholerae* sialidase, as shown in FIG. 3D.

Analysis of cell-surface sialylation levels of different breast cancer cell lines with or without sialidase treatment is shown in FIG. 4A. Ligand levels of Siglec-7 on different breast cancer cell lines with or without sialidase treatment is shown in FIG. 4B. Ligand levels of Siglec-9 on different breast cancer cell lines with or without sialidase treatment is shown in FIG. 4C. Ligand levels of NKG2D on different breast cancer cell lines with or without sialidase treatment is shown in FIG. 4D.

Example 2—Removal of Cell-Surface Sialic Acids Enhance Susceptibility to ADCC

Figure 5:
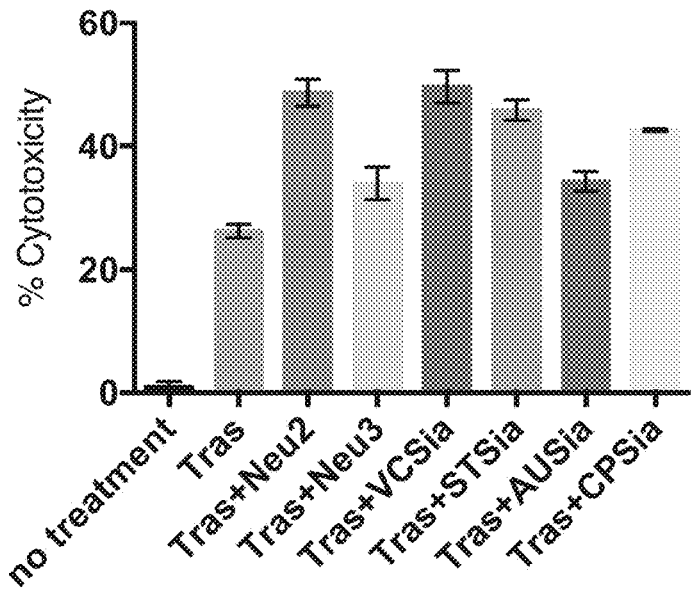
FIG. 5 depicts the cytotoxicity of isolated peripheral blood NK cells in the absence or presence of sialidase.
Figure 5:
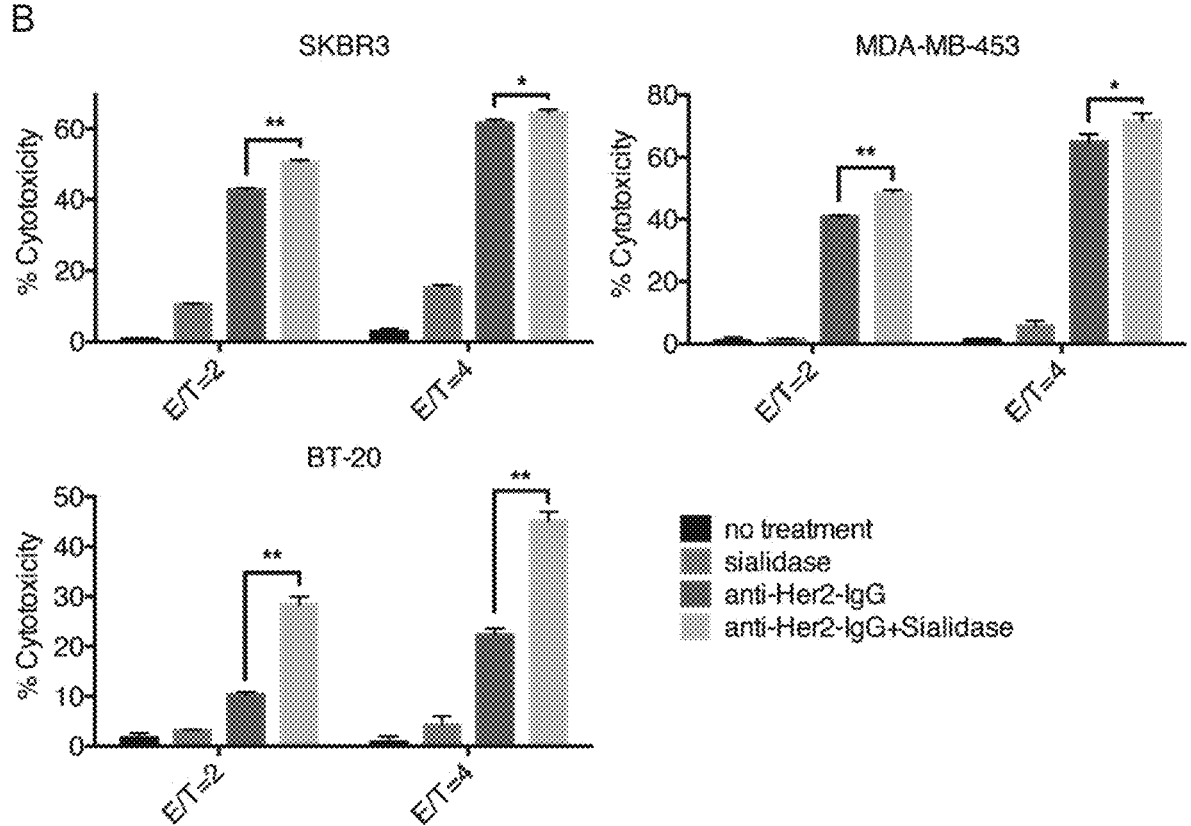
Figure 6:
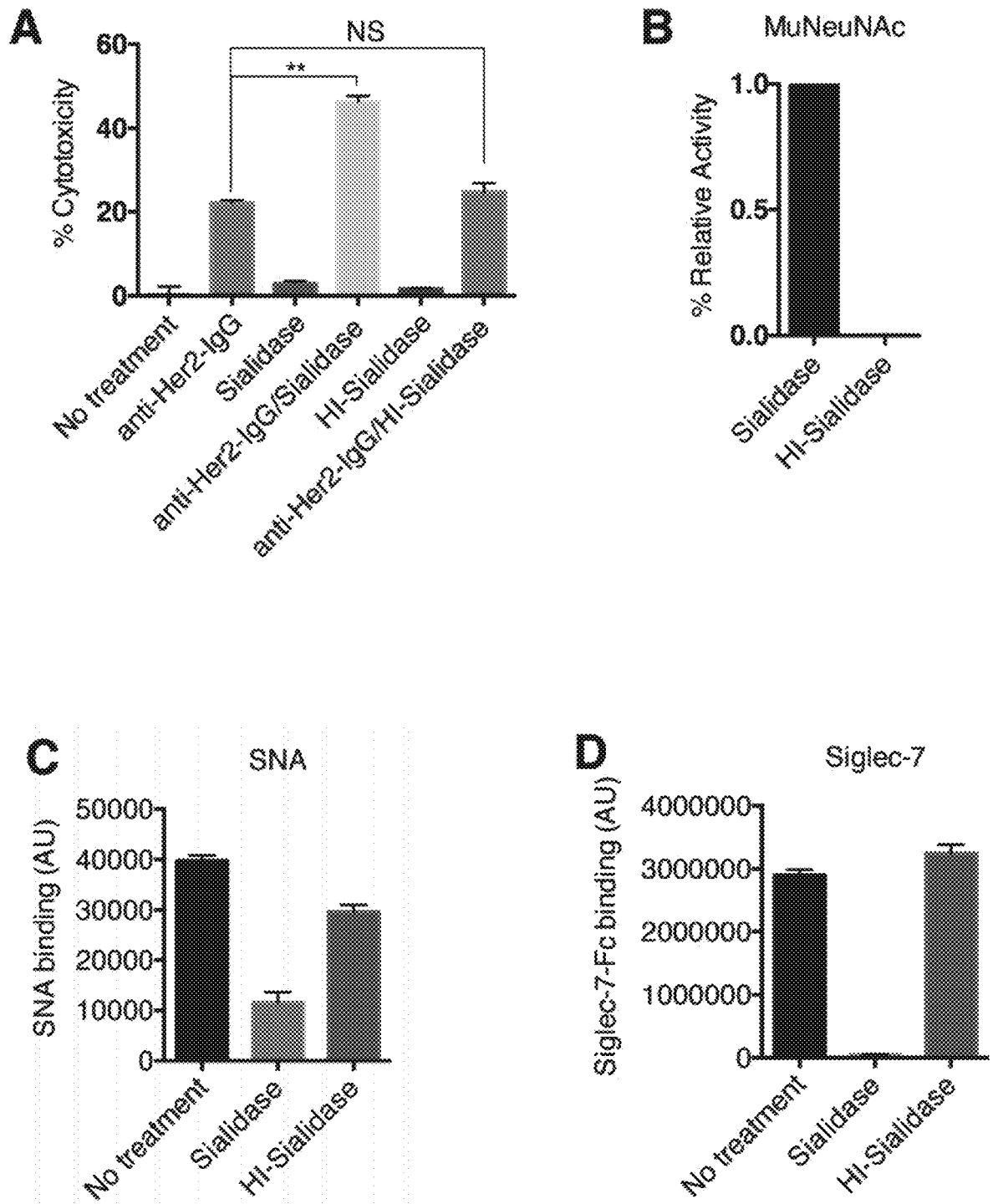
FIG. 6 depicts various assays used for the characterization of wild-type and heat-inactivated *V. cholerae* sialidase.
Figure 6:
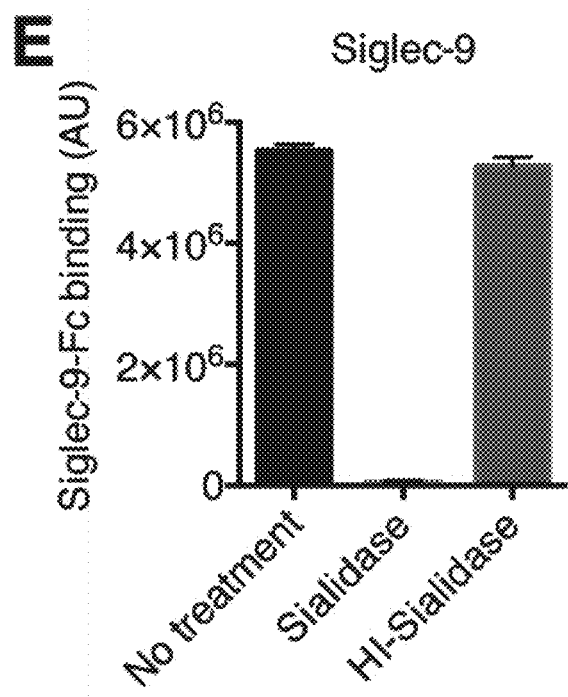
Figure 6:
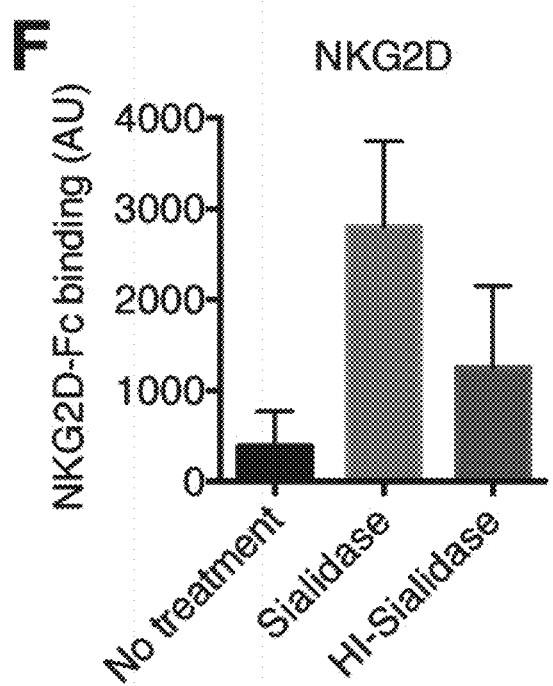

To demonstrate that removal of cell-surface sialic acids can enhance their susceptibility to NK cell-mediated ADCC, ADCC assays were performed with SKBR3 (HER2 3+), MDA-MB-453 (HER2 2+) and BT-20 (HER2 1+) cell lines with and without the sialidase treatment in the presence of 30 nM trastuzumab using purified human peripheral blood NK cells. An approximate 5%-100% increase in maximal cell killing was observed in trastuzumab-directed ADCC with various sialidase-treated cell lines (FIG. 5). To validate that the enhanced ADCC was due to sialidase enzymatic activity, the hydrolytic activity assay and ADCC assay using a heat-inactivated *V. cholerae* sialidase was also performed. Inactivation of *V. cholerae* sialidase by heating to 80° C. for 20 minutes led to the loss of hydrolytic activity against sialic acid containing glycans as well as the loss of the enhancement in ADCC (FIG. 6). It was expected that by conjugating sialidase to trastuzumab, increased local concentration of sialidase on the cell-surface would provide proximity-enhanced activity and further potentiate the effect as well as limit the promiscuity of the enzymatic activity in a tissue-specific manner.

Shown in FIG. 5A is cytotoxicity of isolated peripheral blood NK cells from healthy donors against BT-20 breast cancer cells alone (no treatment), in the presence of anti-Her2-IgG (Tras) or in the presence of anti-HER2-IgG and human neuriminidase 2 (Neu2), human neuriminidase 3 (Neu3), *Vibrio cholerae* sialidase (VCSia), *Salmonella typhimurium* sialidase (STSia), *Arthrobacter ureafaciens* sialidase (AUSia), or *Clostridium perfringens* sialidase, (CPSia). FIG. 5B depicts cytotoxicity of isolated peripheral blood NK cells from healthy donors against different breast cancer cells in the absence or presence of sialidase (30 nM), anti-Her2-IgG (30 nM) or a mixture of sialidase (30 nM) and anti-Her2-IgG (30 nM) at E/T ratios of 2:1 and 4:1. *P<0.05, **P<0.005.

FIG. 6 shows the characterization of wild-type and heat-inactivated *Vibrio cholerae* sialidase. Cytotoxicity of isolated peripheral blood NK cells against BT-20 cells in the absence or presence of anti-Her2-IgG (30 nM), sialidase (30 nM), a mixture of anti-Her2-IgG (30 nM) and sialidase (30 nM), heat-inactivated sialidase (HI-Sialidase 30 nM), or a mixture of anti-Her2-IgG (30 nM) and heat-inactivated sialidase (30 nM) at an E/T ratio of 4:1 is shown in FIG. 6A. Hydrolytic activities of wild-type and heat-inactivated *V. cholerae* sialidase using 2'-(4-methylumbelliferyl)-α-D-N-acetylneuraminic acid (MuNeuNAc) is shown in FIG. 6B. Levels of *Sambucus nigra* lectin (SNA) ligands on BT-20 cells with or without 30 nM wild-type sialidase or heat-inactivated sialidase treatment is shown in FIG. 6C. Levels of Siglec-7 ligands on BT-20 cells with or without 30 nM wild-type sialidase or heat-inactivated sialidase treatment is shown in FIG. 6D. Levels of Siglec-9 ligands on BT-20 cells with or without 30 nM wild-type sialidase or heat-inactivated sialidase treatment is shown in FIG. 6E. Levels of NKG2D ligands on BT-20 cells with or without 30 nM wild-type sialidase or heat-inactivated sialidase treatment is shown in FIG. 6F. **P<0.005, NS: not significant.

Example 3—Preparation and Characterization of Antibody-Sialidase Conjugates

A key concern in designing the sialidase-trastuzumab AEC was to identify a site for enzyme conjugation that would not undermine binding to FcγRIII (CD16), the interaction that initiates ADCC. Inspiration from the field of antibody-drug conjugates (ADCs) was taken where sites of attachment have been tailored to avoid interference with immune effector functions. Accordingly, sialidase was chosen to link near the C-terminus of trastuzumab's heavy chain, far from the $C_H2$ domain at which FcγRIII binds. The aldehyde tag method for site-specific conjugation was used based on precedents of its use in the assembly of protein-protein chemical fusions as well as site-specific antibody-drug conjugates. Trastuzumab (anti-Her2-IgG) bearing a C-terminal aldehyde tag was obtained as previously described. The functionalized antibody was first coupled to aminooxy-tetraethyleneglycol-azide (aminooxy-TEG-$N_3$) (FIG. 2A). In parallel, sialidases were prepared. *V. cholerae* sialidase was randomly functionalized on lysine residues with bicyclononyne-N-hydroxysuccinimide ester (BCN-NHS). After an overnight reaction, excess linker was removed and the extent of BCN-NHS modification of sialidase was determined by ESI-MS (FIG. 7B). Finally, trastuzumab adorned with the azide-functionalized linker was conjugated to BCN-functionalized *V. cholerae* sialidase via copper-free click chemistry (FIG. 2A). The desired conjugate was purified using a size-exclusion column and its apparent molecular weight (anti-Her2-IgG-Sia, ca. 312 kDa) was confirmed by SDS-PAGE (FIG. 2B). ESI-MS analysis confirmed that the sialidase was covalently linked to the heavy chain of trastuzumab (FIG. 2C and FIG. 7E). Sialidase activity of the final AEC was evaluated using the fluorogenic substrate MuNeuNAc. More than 85% enzymatic activity remained after the chemical conjugation process (FIG. 8). Alternatively, *S. typhimurium* sialidase was site-specifically conjugated to the cysteine on the C-terminal aldehyde tag by reacting with DBCO-PEG4-Maleimide overnight; following this excess linker was removed and the conjugation of DBCO to *S. typhimurium* sialidase was determined to be complete by ESI-MS (FIG. 7G). Finally trastuzumab with azide linker was conjugated to DBCO-functionalized *S. typhimurium* sialidase via copper-free click chemistry (FIG. 2D). The desired conjugate was purified using a size-exclusion column and its apparent molecular weight (anti HER2-IgG-StSia, ca 240 kDa) was confirmed by SDS-PAGE (FIG. 2E). ESI-MS analysis confirmed that the sialidase was covalently linked to the heavy chain of trastuzumab (FIG. 2F and FIG. 7H). Sialidase activity of the final AEC was evaluated using the fluorogenic substrate MuNeuNAc. A slight increase in enzymatic activity compared to free aldehyde-tagged sialidase resulted after the chemical conjugation process to the free cysteine on the C-terminal tag (FIG. 8).

Figure 7:
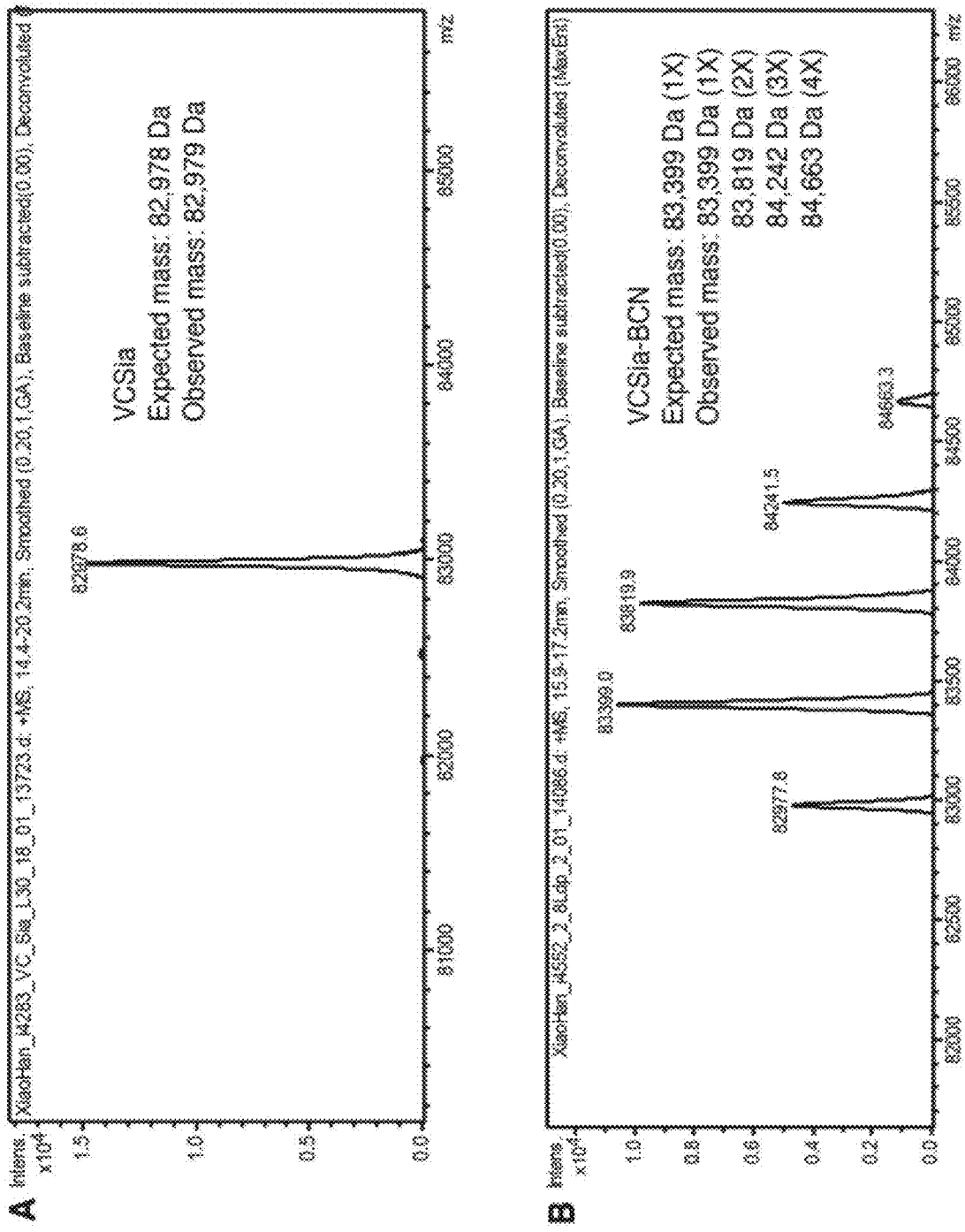
FIG. 7 depicts the ESI-MS spectra for *Vibrio cholerae* sialidase, *Salmonella typhimurium* sialidase, anti-Her2-IgG and its conjugates.
Figure 7:
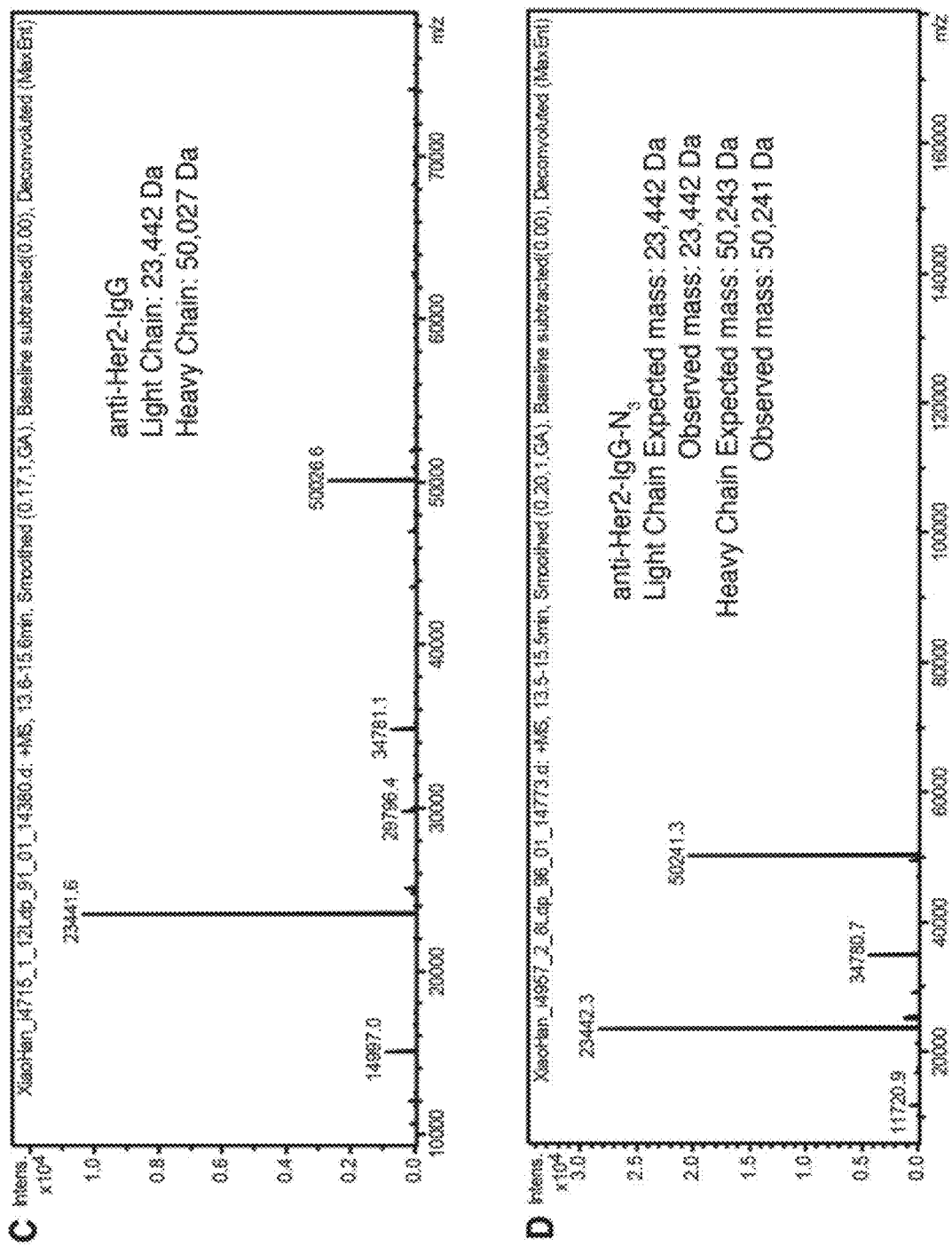
Figure 7:
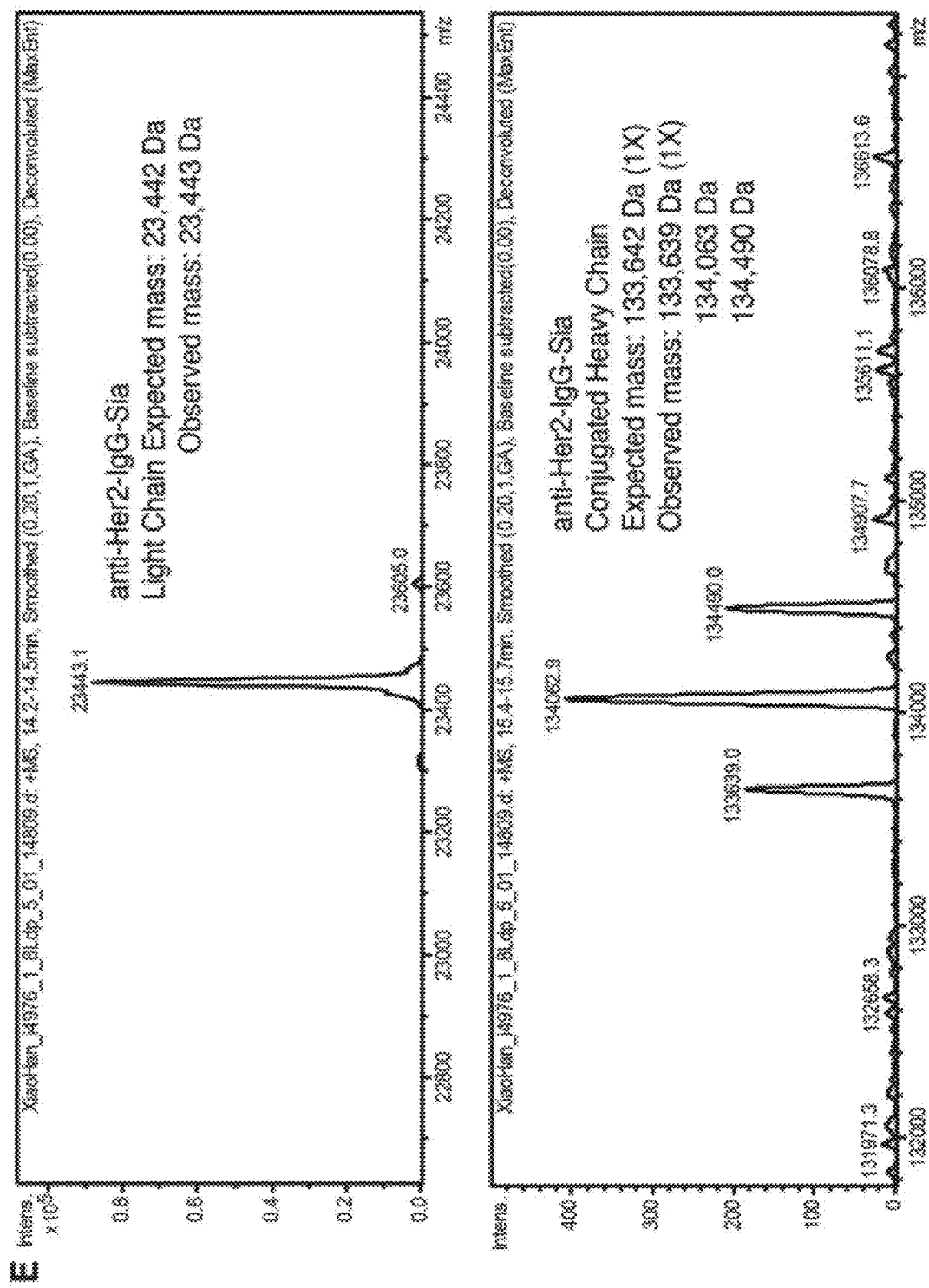
Figure 7:
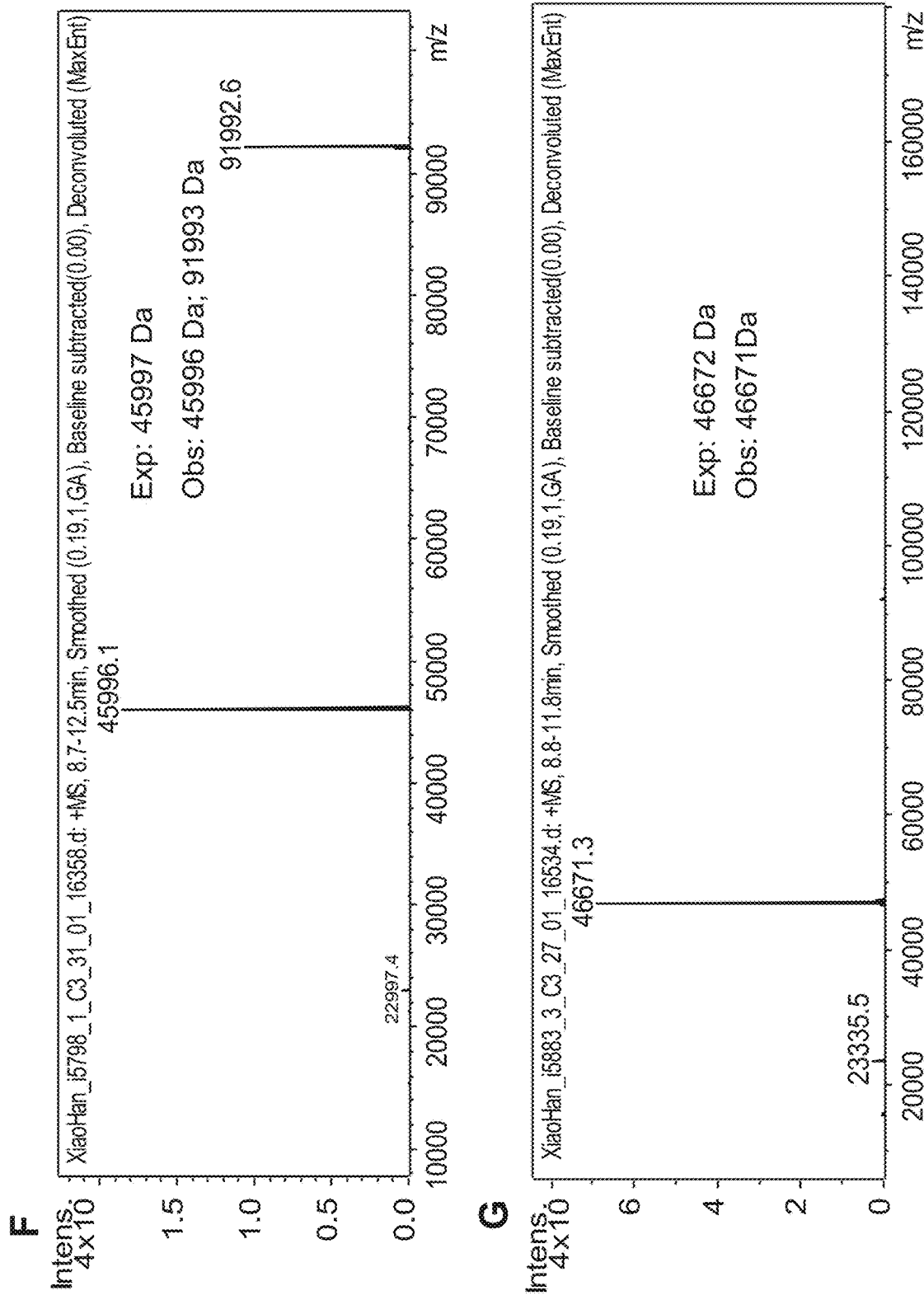
Figure 7:
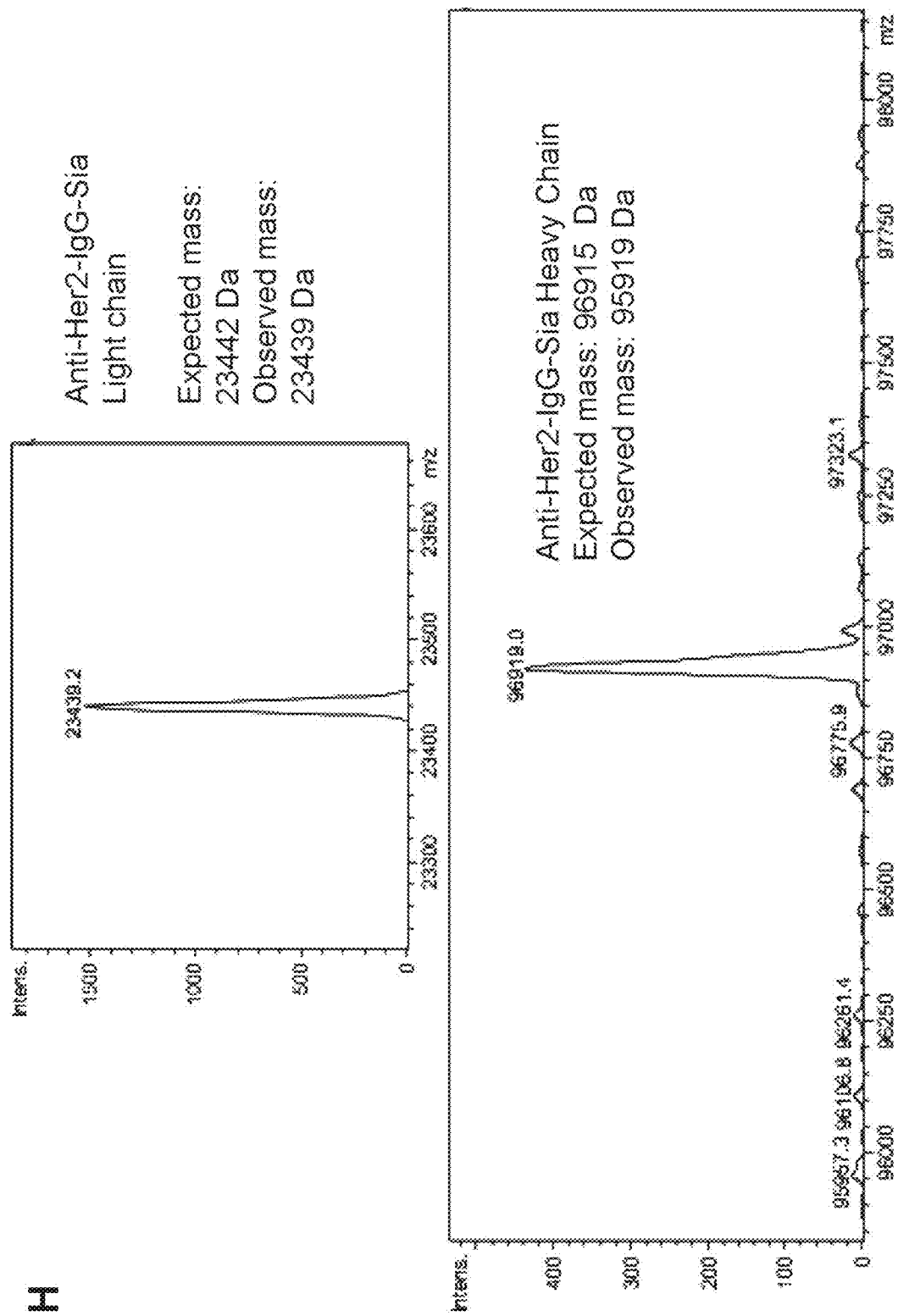
Figure 8:
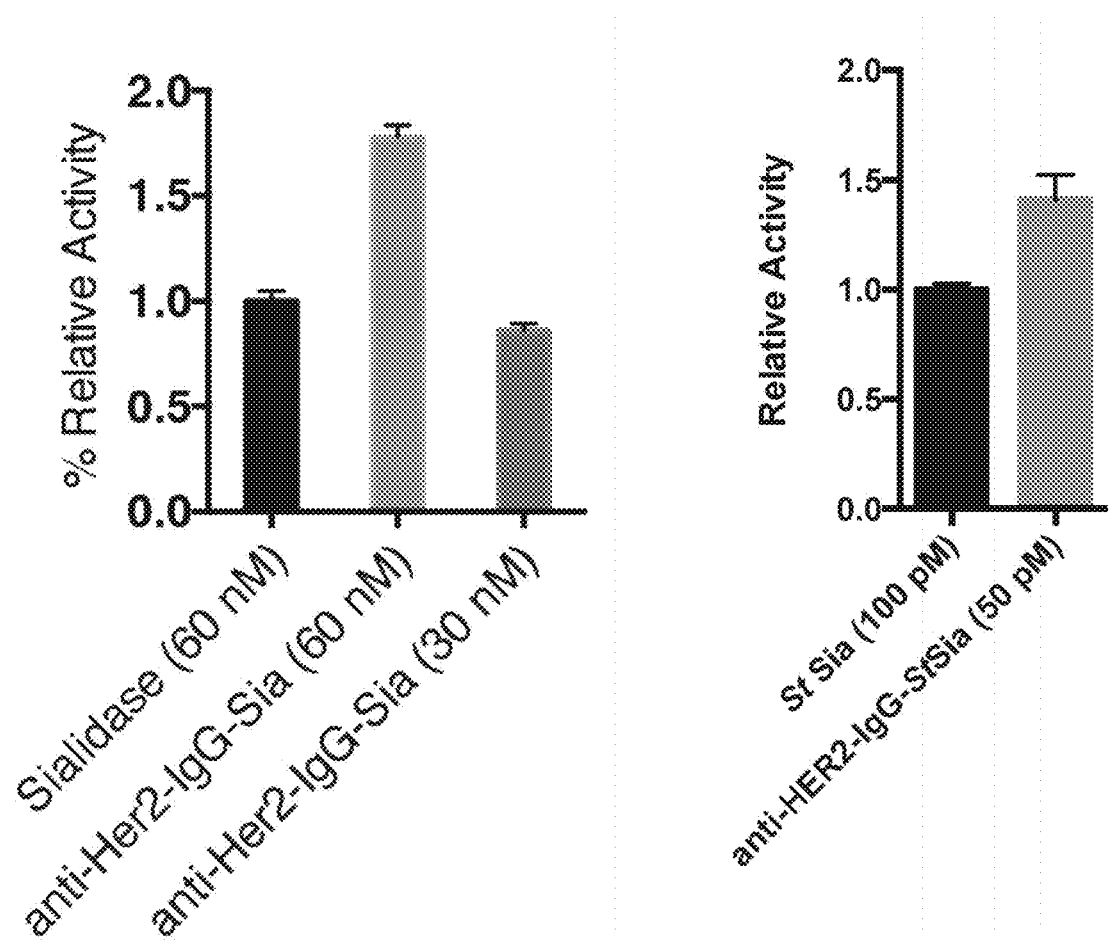
FIG. 8 depicts the hydrolytic activities of *V. cholerae* sialidase and anti-Her2-IgG-Sia. Also depicted is hydrolytic activities of *S. typhimurium* sialidase and anti-Her2-IgG-StSia.

FIG. 7 shows ESI-MS spectra of sialidase, anti-Her2-IgG and its conjugates. ESI-MS spectrum of purified *Vibrio cholerae* sialidase is shown in FIG. 7A. ESI-MS spectrum of *V. cholerae* sialidase labeled with BCN-NHS at 1:12 molar ratio is shown in FIG. 7B. ESI-MS spectrum of anti-Her2-IgG with C-terminal aldehyde tag is shown in FIG. 7C. ESI-MS spectrum of anti-Her2-IgG with C-terminal aldehyde tag conjugated with aminooxy-TEG-azide is shown in FIG. 7D. ESI-MS spectrum of anti-Her2-IgG-Sia is shown in FIG. 7E. ESI-MS of purified *Salmonella typhimurium* sialidase is shown in FIG. 7F. ESI-MS of *S. typhimurium* labeled with DBCO_PEG4-Maleimide at a 1:20 molar ratio is shown in FIG. 7G. ESI-MS spectrum of anti-HER2-IgG-St-Sia FIG. 8 shows the hydrolytic activities of *V. cholerae* sialidase and anti-Her2-IgG-Sia, as well as *S. typhimurium* sialidase and anti-Her2-IgG-StSia against substrate 2'-(4-methylumbelliferyl)-α-D-N-acetylneuraminic acid (Mu-NeuNAc)

Figure 9:
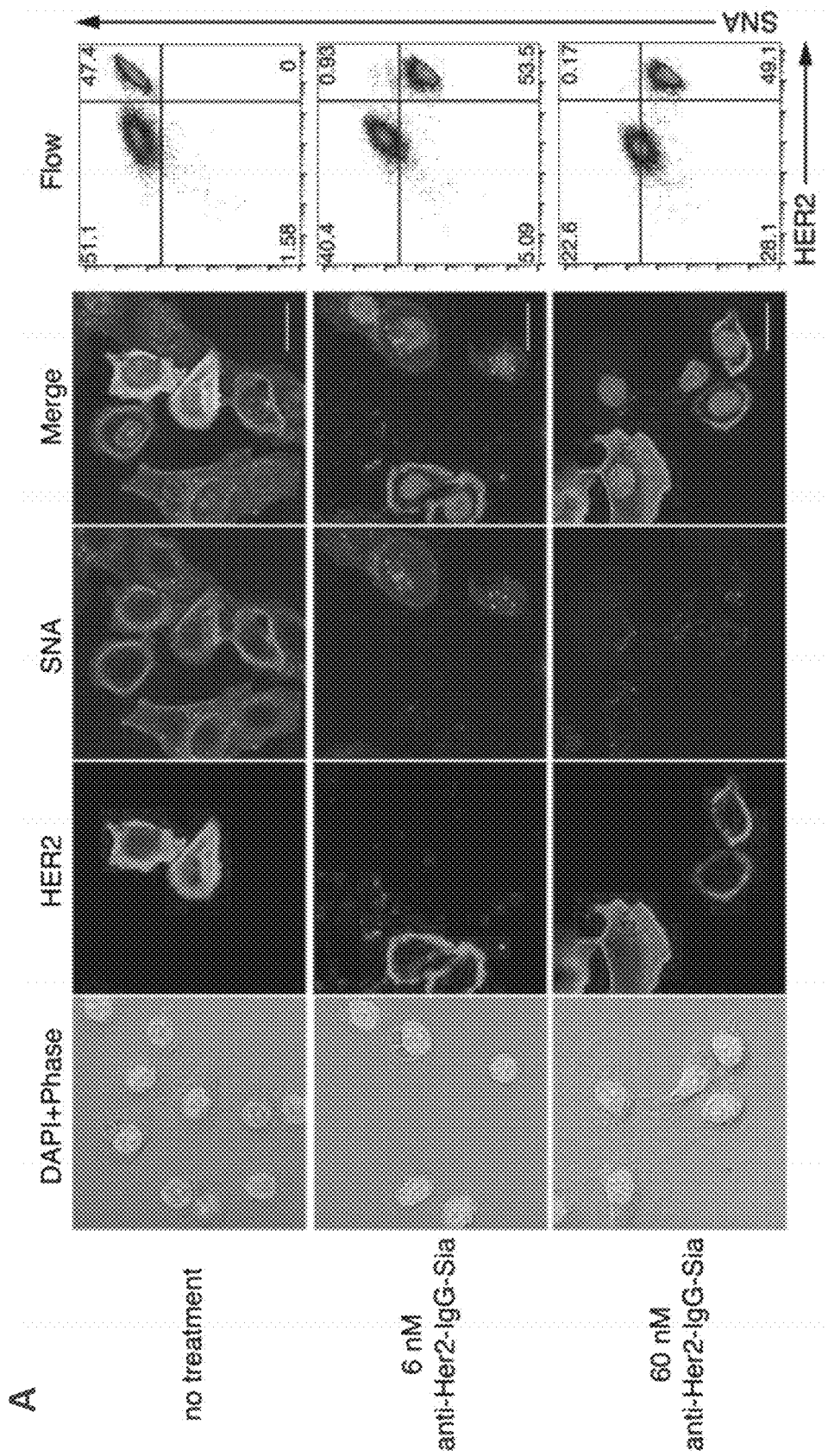
FIG. 9 depicts images showing the level of cell-surface sialic acid in various cell lines, with or without trastuzumab-sialidase conjugate treatment. Also shown is flow cytometry data comparing removal of cell-surface sialic acid by two trastuzumab-sialidase conjugates in various cell lines.
Figure 9:
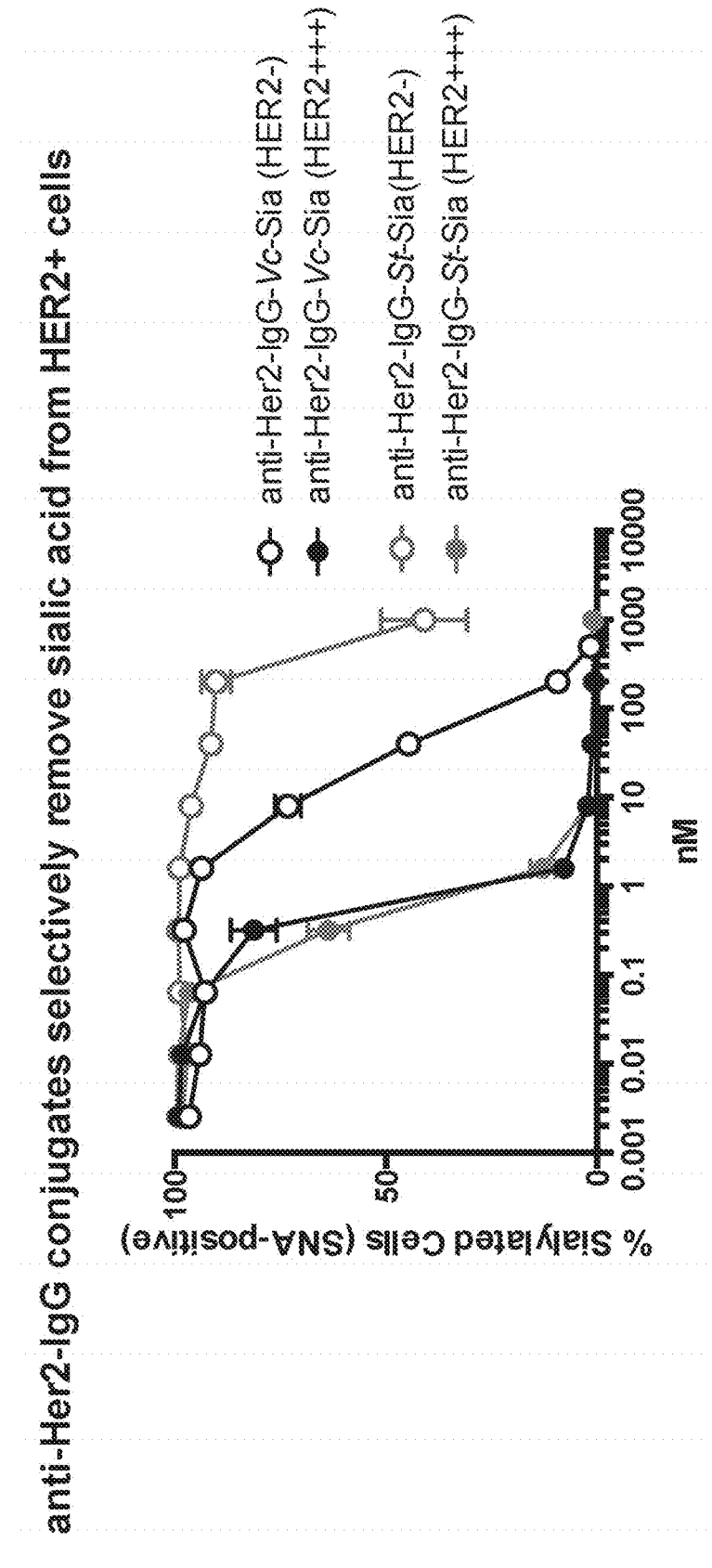
Figure 10:
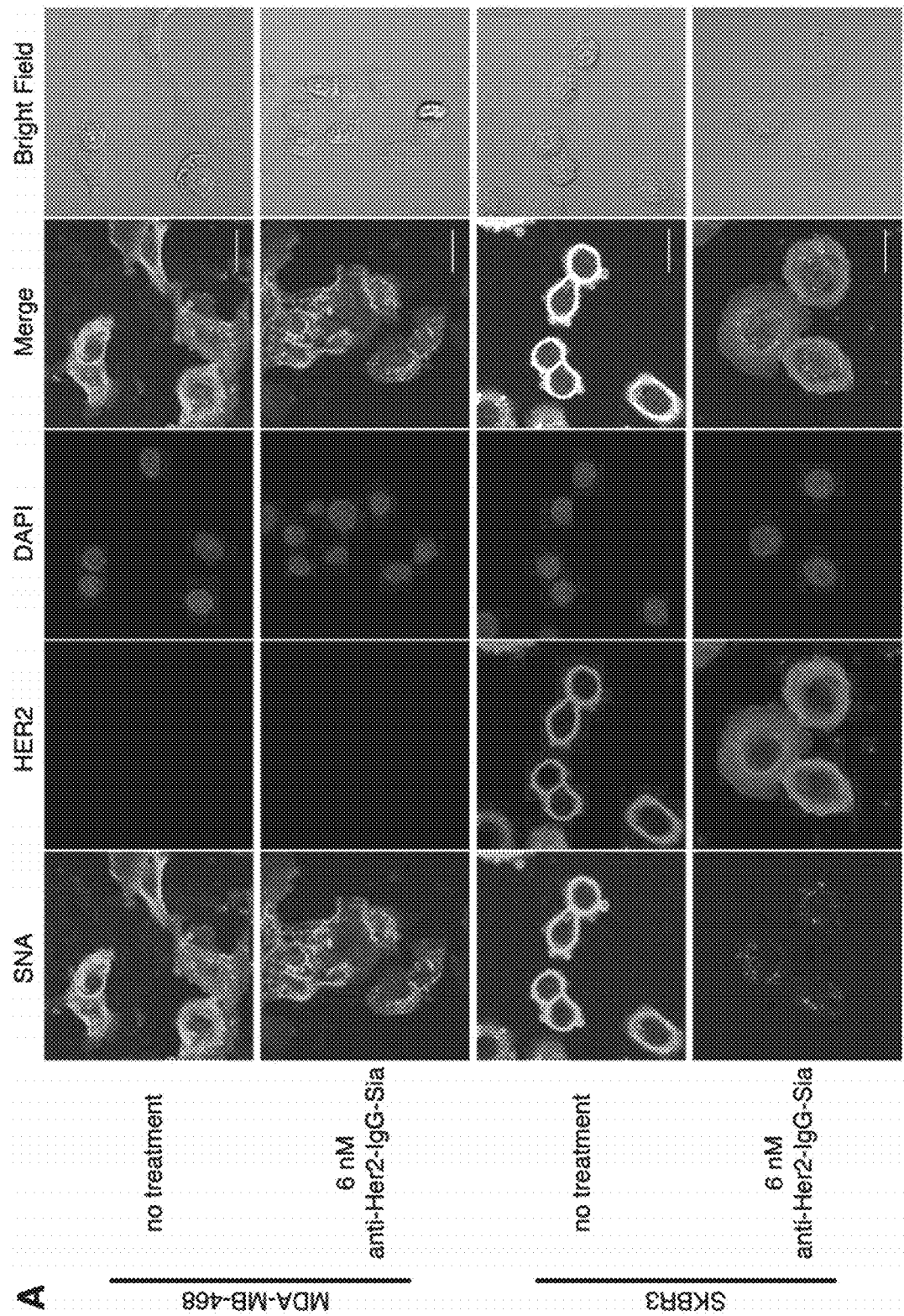
FIG. 10 depicts images showing *Sambucus nigra* ligands on various cell lines in the absence or presence of anti-Her2-IgG-Sia conjugate.
Figure 10:
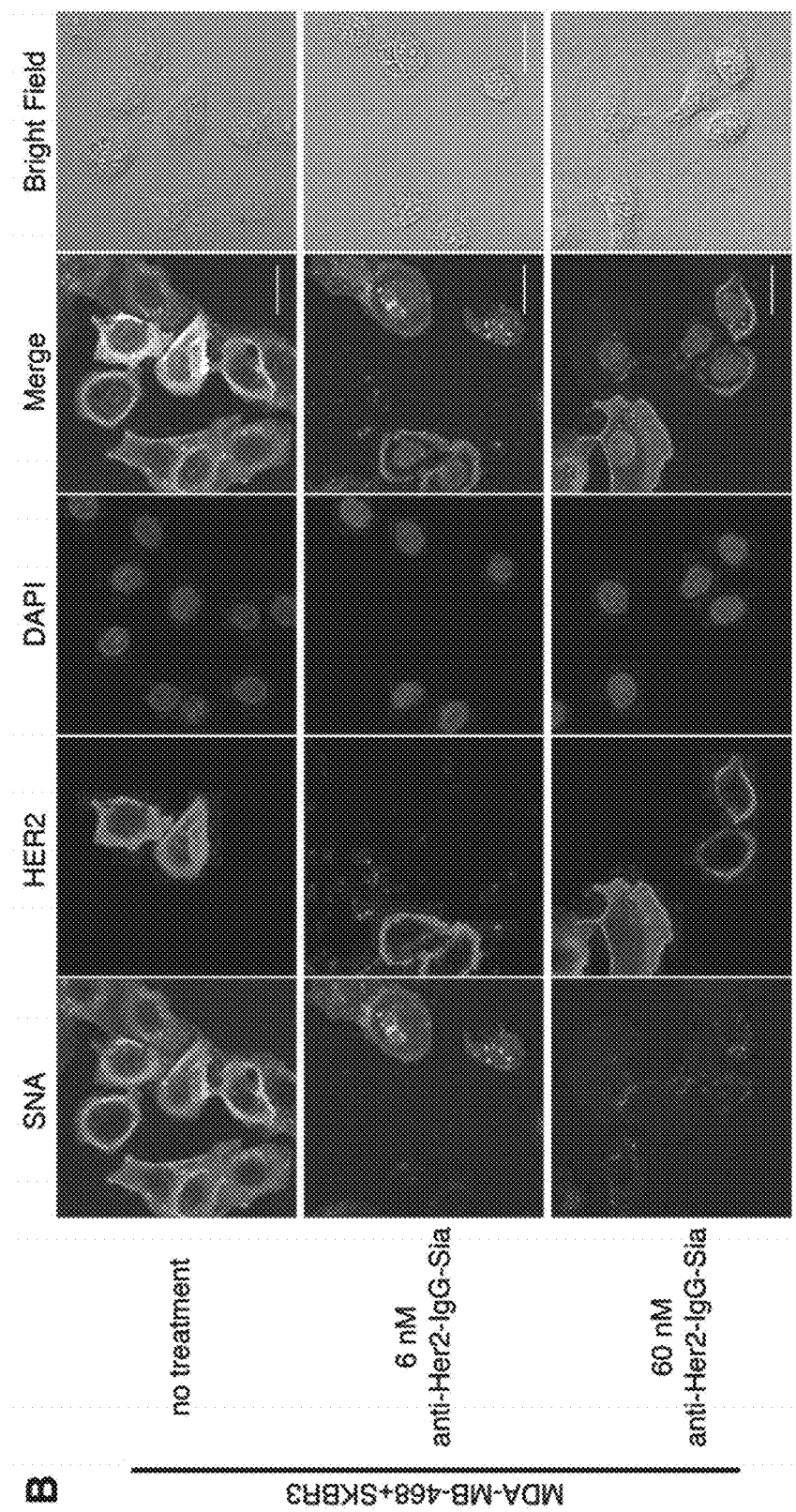

To further demonstrate that anti-Her2-IgG-Sia is able to specifically remove sialic acid on HER2-expressing cells, SKBR3 (HER2 3+) and MDA-MB-468 (HER2 0) were incubated in the absence or presence of 6 nM or 60 nM anti-Her2-IgG-Sia. As shown in FIG. 9 and FIG. 10, treatment with 6 nM anti-Her2-IgG-Sia for 1 h resulted in a selective desialylation of SKBR3 cells even in the presence of MDA-MB-468 cells (FIG. 9). However, this effect is dose-dependent. Surface sialic acid levels of SKBR3 and MDA-MB-468 cells were both reduced with a treatment at 60 nM of anti-Her2-IgG-Sia for 1 h. This effect was quantified using flow cytometry on mixtures of cells treated with various concentrations of anti-Her2-IgG-Sia (FIG. 9A). However, in another conjugate with a smaller sialidase lacking lectin domains (anti-HER2-IgG-St-Sia) surface sialic acid levels of off-target HER2 0 MDA-MB-468 cells remained untouched until much higher concentrations of about 1 µM anti-Her2-IgG-St-Sia conjugate (FIG. 9B).

FIG. 9 shows in vitro characterization of trastuzumab and trastuzumab-sialidase conjugate with different HER2-expressing cancer cells. Cell-surface sialic acid on the HER2-high expressing cell line, SKBR3, can be selectively removed using 6 nM trastuzumab-sialidase conjugate. Scale bar, 25 µm.

FIG. 10 shows SNA ligands on SKBR3 and MDA-MB-468 cells in the absence or presence of anti-Her2-IgG-Sia conjugate. SNA ligands on individual cultures of SKBR3 and MDA-MB-468 cells in the absence or presence of anti-Her2-IgG-Sia conjugate is shown in FIG. 10A. Cells were incubated with 6 nM anti-Her2-IgG-Sia conjugate or PBS in RPMI-1640 media for 1 hour at 37° C. and stained with FITC-labeled SNA lectin, AF647-labeled anti-Her2 and DAPI nuclear stain. SNA ligands on a mixture of SKBR3 and MDA-MB-468 cells in the absence or presence of anti-Her2-IgG-Sia conjugate is shown in FIG. 10B. SKBR3 and MDA-MB-468 cells were mixed at a 1:1 ratio and cultured overnight. The cell mixtures were incubated in the absence or presence of 6 nM or 60 nM anti-Her2-IgG-Sia conjugate for 1 hour at 37° C. Scale bar=25 µm.

Figure 11:
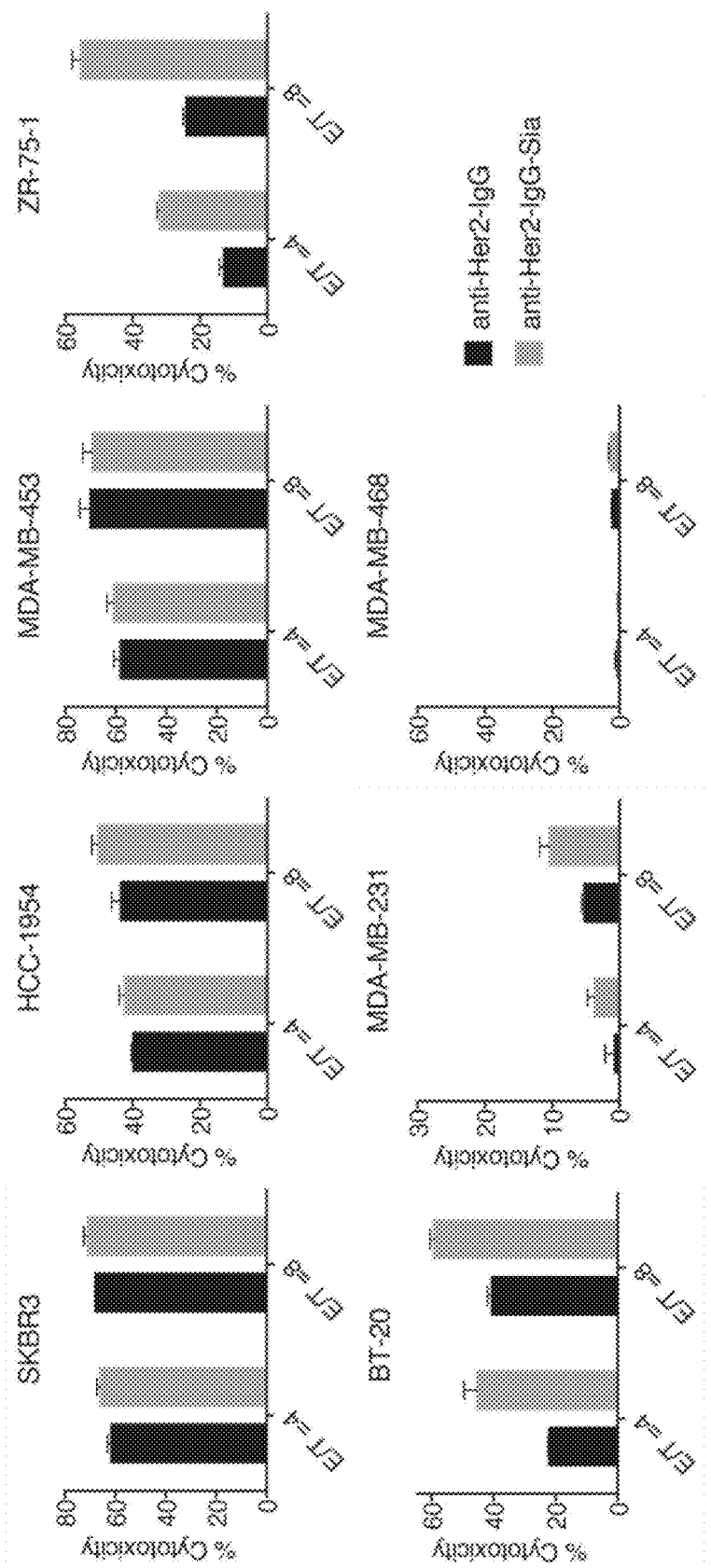
FIG. 11 depicts the cytotoxicity of isolated peripheral blood NK cells in the presence of anti-Her2-IgG or anti-Her2-IgG-Sia.

To assess the effect of the antibody-sialidase conjugate on NK cell-mediated ADCC, cytotoxicity assays were performed using various breast cancer cell lines (SKBR3, HER2 3+; HCC-1954, HER2 3+; MDA-MB-453, HER2 2+; ZR-75-1, HER2 1+; BT-20, HER2 1+; MDA-MB-231, HER2 1+; MDA-MB-468, HER2 0) in the presence of anti-Her2-IgG or anti-Her2-IgG-Sia at effector/target (E/T) ratios of 4:1 and 8:1. In comparison to anti-Her2-IgG, anti-Her2-IgG-Sia demonstrated increases of 33% to 140% of maximal cell killing with HER2 1+ cell lines ZR-75-1, BT-20, and MDA-MB-231 (FIG. 11). In addition, BT-20 cells were exposed to purified human peripheral blood NK cells at various E/T ratios in the absence or presence of sialidase (30 nM), anti-Her2-IgG (30 nM), or anti-Her2-IgG-Sia (30 nM) (FIG. 12A). Sialidase treatment alone of BT-20 cells lines showed little NK cell-mediated cytotoxicity at different E/T ratios. Compared to anti-Her2-IgG, anti-Her2-IgG-Sia showed significantly improved cytolysis at various ratios. At an E/T ratio of 4, the largest enhancement was observed: 46%±1 cytolysis for anti-Her2-IgG-Sia versus 21%±1 for anti-Her2-IgG. It was verified that ADCC was likely being mediated by NK cells as NK cell-depleted PBMCs showed little cell lysis (FIG. 12B).

FIG. 11 shows cytotoxicity data of isolated peripheral blood NK cells from healthy donors against different breast cancer cells in the presence of anti-Her2-IgG (30 nM) or anti-Her2-IgG-Sia (30 nM) at E/T ratios of 4:1 and 8:1.

Figure 12:
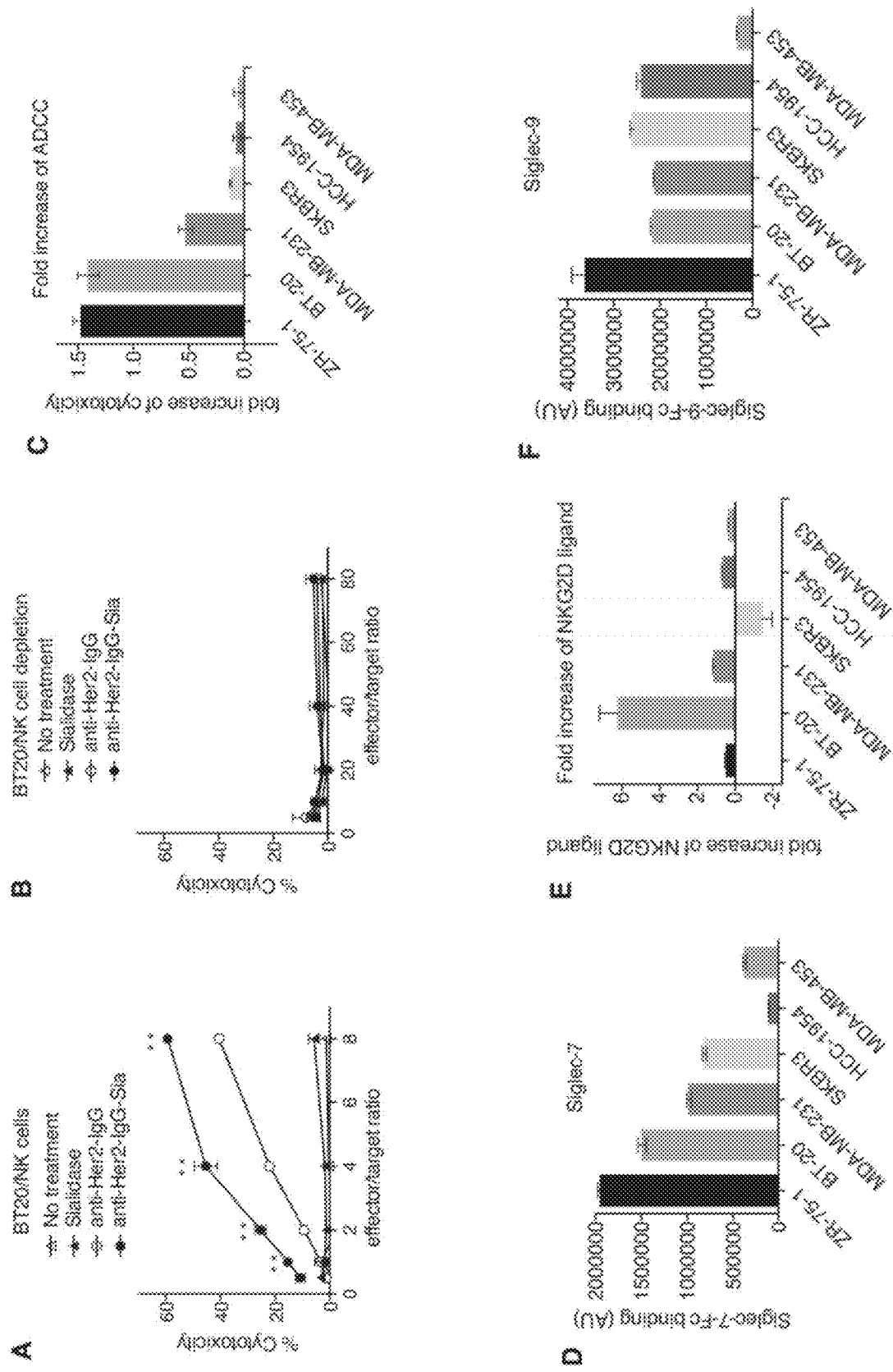
FIG. 12 depicts the activity of trastuzumab and trastuzumab-sialidase conjugate against HER-2 expressing cancer cells.
Figure 12:
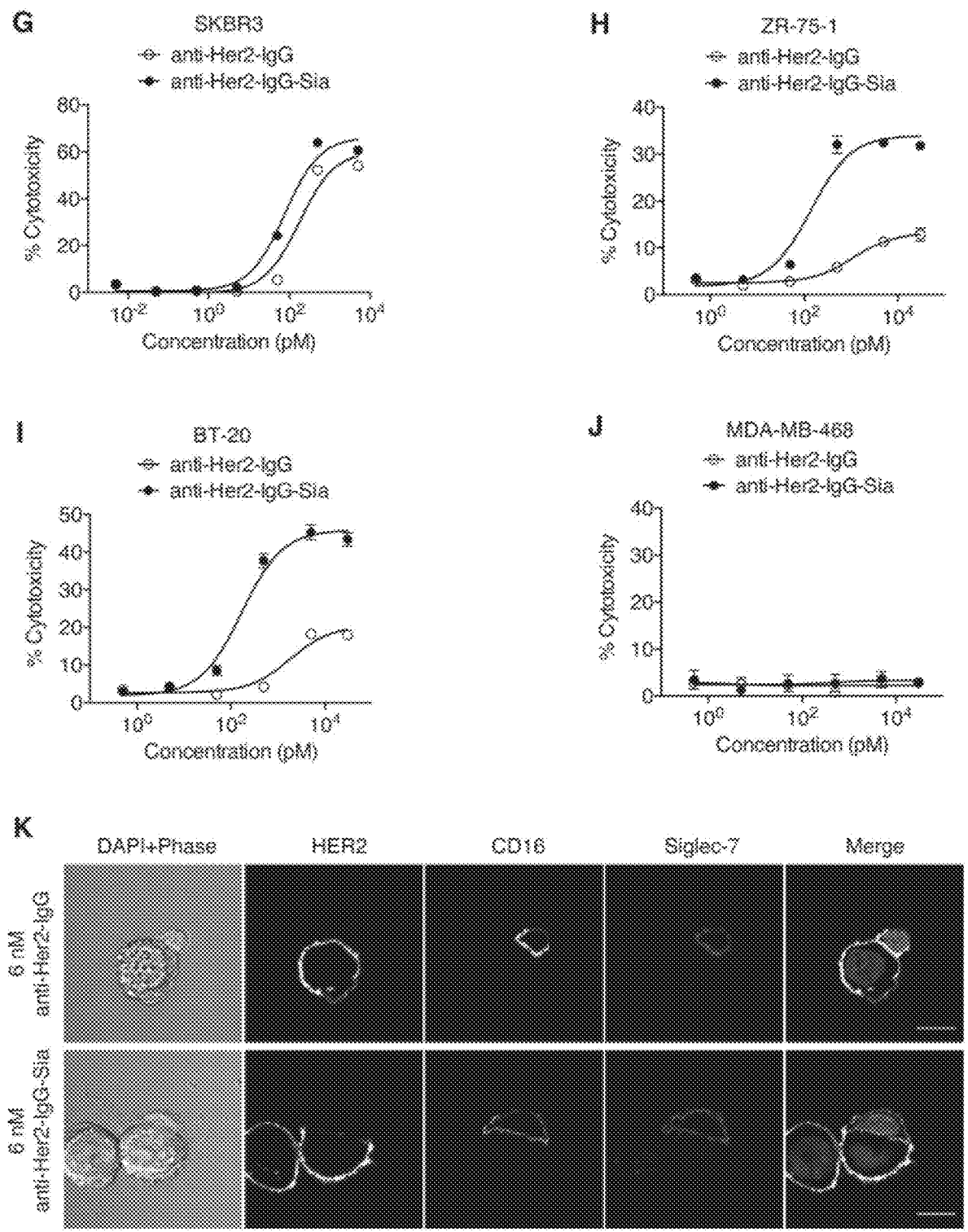

FIG. 12 shows in vitro activity of trastuzumab and trastuzumab-sialidase conjugate against different HER2-expressing cancer cells. Cytotoxicity assays performed with BT-20 cells in the absence or presence of sialidase (30 nM), anti-Her2-IgG (30 nM) and anti-Her2-IgG-Sia (30 nM) using NK cells are shown in FIG. 12A. Results of cytotoxicity assays performed with BT-20 cells in the absence or presence of sialidase (30 nM), anti-Her2-IgG (30 nM) and anti-Her2-IgG-Sia (30 nM) using NK cells-depleted PBMCs are shown in FIG. 12B. The trend seen in the enhancement of ADCC correlated with Siglec-7-Fc, Siglec-9-Fc and NKG2D-Fc binding is shown in FIG. 12C-12F. Cytotoxic activity of NK cells against different HER2-expressing cancer cells in the presence of indicated concentrations of trastuzumab and trastuzumab-sialidase conjugate is shown in FIG. 12G-12J. Fluorescent microscopy analysis of Siglec-7 distribution on NK cells with trastuzumab or trastuzumab-sialidase conjugate treatments is shown in FIG. 12K. Siglec-7 displayed recruitment to the NK synapse with trastuzumab treatment. After removing sialic acids on SKBR3 cells using trastuzumab-sialidase conjugate, Siglec-7 recruitment to the NK-tumor synapse is lost. Scale bar, 10 µm, *P<0.005.

Figure 13:
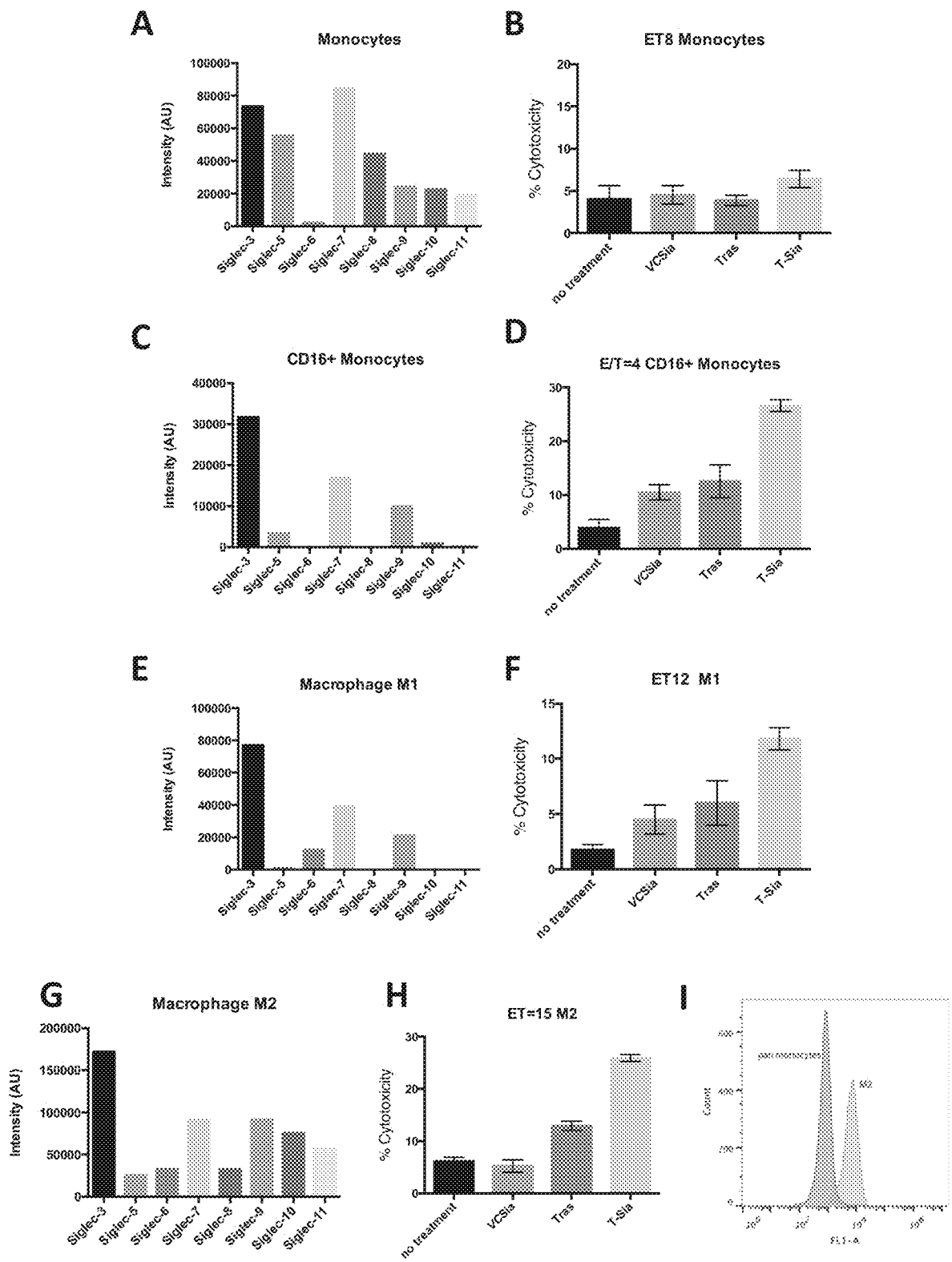
FIG. 13 depicts the siglec expression levels and cytotoxicity of isolated monocyte populations and differentiated macrophages in the presence of sialidase, trastuzumab, and trastuzumab-sialidase conjugates against HER2+ expressing cancer cells.

To assess the effect of the antibody-sialidase conjugate on cytotoxicity mediated by monocytes and macrophages, cytotoxicity assays were performed using breast cancer cell lines (SKBR3, HER2 3+; BT-20, HER2 1+) in the presence of *Vibrio cholerae* sialidase alone (VCSia), anti-Her2-IgG (Tras), or anti-Her2-IgG-Sia (T-Sia) at various effector/target (E/T) ratios. Whereas the total monocyte population exhibited low overall killing of tumor cells, isolated CD16+ monocytes primarily expressing Siglecs 3, 7, and 9 demonstrated increases of about 100% upon treatment with the conjugate anti-Her2-IgG-Sia (T-Sia) compared to treatment with anti-Her2-IgG (Tras) (FIG. 13). Differentiated M1 macrophages expressing Siglecs 3, 6, 7, and 9, and M2 macrophages expressing Siglecs 3, 5, 6, 7, 8, 9, 10, and 11 both appear to exhibit increases in cytotoxic killing of tumor cells with trastuzumab-sialidase conjugate as opposed to trastuzumab alone (FIG. 13). γδ T cell mediated cytotoxicity can also be potentiated by trastuzumab sialidase conjugate (T-Sia) rather than treating with trastuzumab (Tras) or sialidase (VCSia) alone (FIG. 14).

FIG. 13A depicts the siglec expression levels of a human isolated monocyte population as determined by flow cytometry. FIG. 13B shows cytotoxicity data of isolated human monocytes against BT-20 breast cancer cells after 24 hours incubation with *V. cholerae* sialidase, anti-HER2-IgG (Tras), or anti-Her2-IgG-Sia (T-Sia) and an E:T ratio of 1:8. FIG. 13C depicts the siglec receptor expression levels of CD16+ monocytes isolated from the monocyte population. FIG. 13D. Shows cytotoxicity data of CD16+ monocytes from healthy donors after four hours incubation with *V. cholerae* sialidase, anti-HER2-IgG (Tras), or anti-Her2-IgG-Sia (T-Sia) and BT-20 breast cancer cells. FIG. 13E depicts the siglec receptor expression levels of isolated monocytes from healthy donors that have been differentiated into M1 macrophages as described previously. FIG. 13F shows cytotoxicity data from M1 macrophages differentiated from isolated monocytes from healthy donors after 24 hours incubation with *V. cholerae* sialidase, anti-HER2-IgG (Tras), or anti-Her2-IgG-Sia (T-Sia) and SK-BR-3 breast cancer cells. FIG. 13G depicts the siglec receptor expression levels of isolated monocytes from healthy donors that have been differentiated into M2 macrophages as described previously. FIG. 13H shows cytotoxicity data from M2 macrophages differentiated from isolated monocytes from healthy donors after 24 hours incubation with *V. cholerae* sialidase, anti-HER2-IgG (Tras), or anti-Her2-IgG-Sia (T-Sia) and SK-BR-3 breast cancer cells. FIG. 13I shows the CD16 expression level of the M2 macrophages from (13E and 13F).

Figure 14:
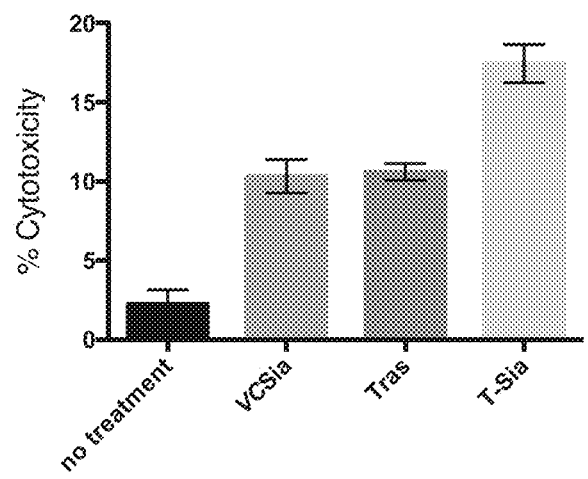
FIG. 14 depicts the cytotoxicity of isolated γδ T cells in the presence of sialidase, trastuzumab, or trastuzumab-sialidase conjugate against HER2+ expressing cancer cells.

FIG. 14 depicts the cytotoxicity of isolated γδ T cells in the presence of *V. cholerae* sialidase, anti-HER2-IgG (Tras), or anti-Her2-IgG-Sia (T-Sia) and SK-BR-3 cells at an E:T of 5:1.

Example 4—Mechanisms of Enhanced ADCC Using Antibody-Sialidase Conjugate

Figure 15:
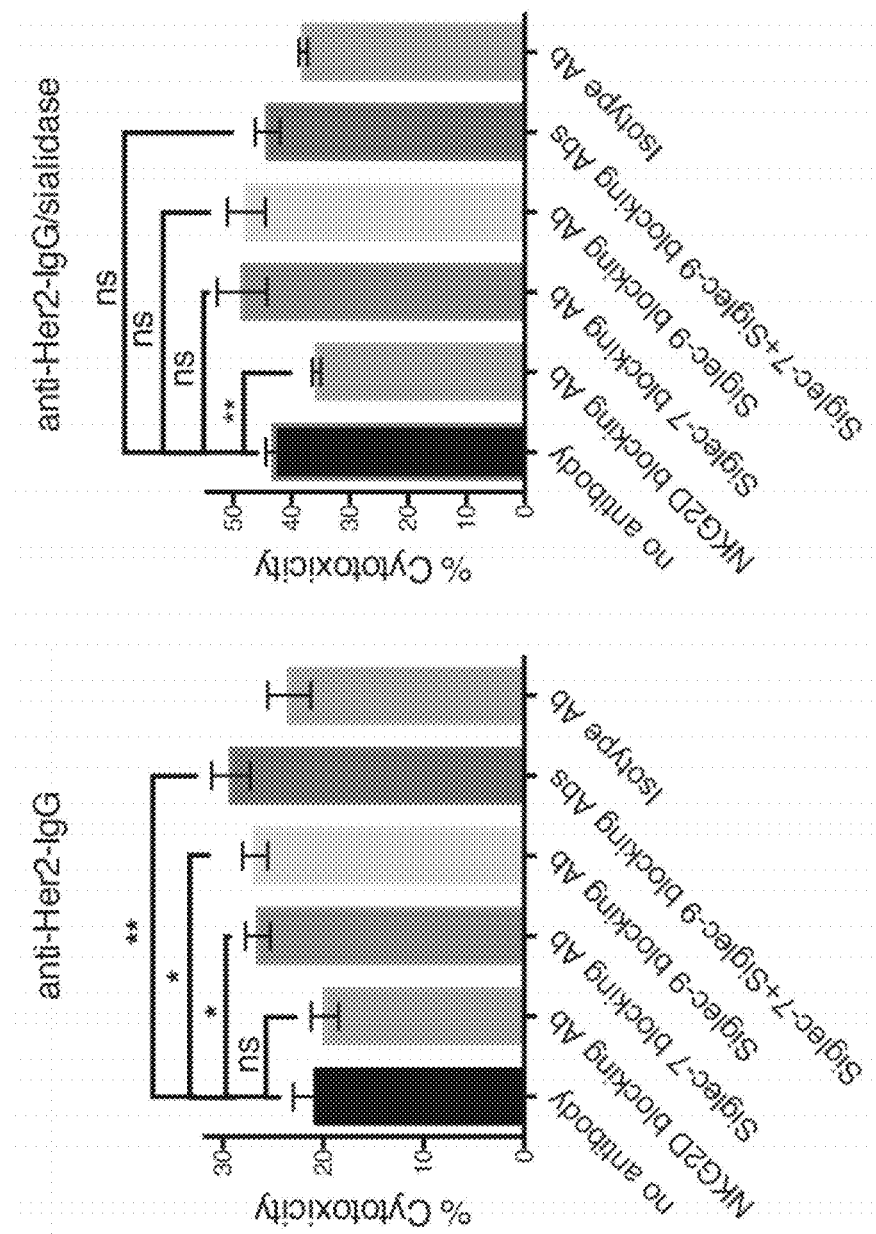
FIG. 15 depicts the cytotoxicity of peripheral blood NK cells with anti-Her2-IgG or a mixture of anti-Her2-IgG and sialidase in the absence or presence of blocking antibodies as specified.

Previous studies have suggested that hypersialylation of cancer cells results in the reduced binding of activating receptor NKG2D as well as enhanced binding of inhibitory receptors, Siglec-7 and Siglec-9, thus reducing NK-mediated cytotoxicity. To explore the mechanism of increased ADCC using trastuzumab-sialidase conjugate, fold increase of ADCC was correlated with receptor binding in various breast cancer cell lines. Cell lines with the highest increases of NK-mediated ADCC correlated with the highest levels of Siglec-7 and Siglec-9 binding (FIGS. 12C-12E). Treatment of BT-20 and ZR-75-1 cells—those with the highest expression of Siglec-7 and Siglec-9 surface ligands—with trastuzumab-sialidase conjugate enhanced ADCC by more than 2 fold compared to trastuzumab alone. In contrast, the conjugate offered little significant improvement on ADCC of MDA-MB-453 cells, which have the lowest expression of Siglec-7 and Siglec-9 surface ligands. To further substantiate that anti-Her2-IgG-Sia was enhancing ADCC through a reduction in binding of inhibitory receptors Siglec-7 and Siglec-9 along with enhancement of the interaction with activating receptor NKG2D, blocking antibodies against Siglec-7, Siglec-9 and NKG2D were used to specifically block ligand-receptor interactions. Anti-Siglec-7 and anti-Siglec-9 antibodies at 5 μg/mL led to significantly enhanced NK cell cytotoxicity against BT-20 cells with anti-Her2-IgG, but not with a mixture of anti-Her2-IgG and sialidase (FIG. 15). In addition, blocking the NKG2D receptor showed a greater effect on ADCC in the mixture of anti-Her2-IgG and sialidase-treated cells compared to anti-Her2-IgG-mediated ADCC (FIG. 15).

FIG. 15 shows results relating to cytotoxicity of isolated peripheral blood NK cells from healthy donors against BT-20 cells with anti-Her2-IgG (30 nM) or a mixture of anti-Her2-IgG (30 nM) and sialidase (30 nM) in the absence or presence of 5 μg/mL blocking anti-NKG2D (clone 149810), anti-Siglec-7 (clone S7.7), anti-Siglec-9 (clone S9), a mixture of anti-Siglec-7 (clone S7.7) and anti-Siglec-9 (clone S9), or mouse IgG1 isotype antibody (clone MOPC-21) at an E/T ratio of 4:1. *P<0.05, *P<0.005, ns: not significant.

Example 5—Comparison Between Antibody-Sialidase Conjugate and Antibody Alone

In order to directly compare the ability of anti-Her2-IgG-Sia to direct ADCC versus anti-Her2-IgG alone, the dose response for cytotoxicity was measured using four different breast cancer cell lines: SKBR3 (HER2 3+), ZR-75-1 (HER2 1+), BT-20 (HER2 1+), MDA-MB-468 (HER2 0). Compared to anti-Her2-IgG, anti-Her2-IgG-Sia is more cytotoxic in all three HER2-expressing cell lines at an E/T ratio of 4. For the HER2 3+ cell line, anti-Her2-IgG-Sia killed SKBR3 cells with an $EC_{50}$ of 76±14 pM, which was slightly better than anti-Her2-IgG ($EC_{50}$ 177±54 pM). While for HER2 1+ cell lines ZR-75-1 and BT-20, the anti-Her2-IgG-Sia is ~10 times more cytotoxic than the anti-Her2-IgG (ZR-75-1 cells: anti-Her2-IgG-Sia $EC_{50}$ 135±47 pM, anti-Her2-IgG $EC_{50}$ 1143±274 pM; BT-20 cells: anti-Her2-IgG-Sia $EC_{50}$ 170±34 pM, anti-Her2-IgG $EC_{50}$ 1823±850 pM) (FIGS. 12G-12J and Table 6). Little lysis of the HER2 negative cell line MDA-MB-468 was observed for either anti-Her2-IgG or anti-Her2-IgG-Sia (FIG. 12J). Next, the difference between anti-Her2-IgG-Sia and a mixture of anti-Her2-IgG and unconjugated sialidase (anti-Her2-IgG/sialidase) was tested. Anti-Her2-IgG-Sia showed lower $EC_{50}$ in SKBR3 cells (anti-Her2-IgG-Sia $EC_{50}$ 76±14 pM; anti-Her2-IgG/sialidase $EC_{50}$ 136±52 pM), ZR-75-1 cells (anti-Her2-IgG-Sia $EC_{50}$ 135±47 pM; anti-Her2-IgG/sialidase $EC_{50}$ 492±67 pM), and BT-20 cells (anti-Her2-IgG-Sia $EC_{50}$ 170±34 pM; anti-Her2-IgG/sialidase $EC_{50}$ 692±156 pM) (Table 6). The enhanced potency of the conjugate versus the mixture of anti-Her2-IgG and unconjugated sialidase is evidence of a proximity effect on the enzymatic activity.

TABLE 6

Cytotoxic activity of isolated NK cells against various human breast cancer cells induced by anti-Her2-IgG, a mixture of anti-Her2-IgG and sialidase, or anti-Her2-IgG-Sia conjugate. (N.D. none detected).

| Cell line | HER2 level | EC$_{50}$ (pM)/Maximal killing (%) | | |
|---|---|---|---|---|
| | | anti-Her2-IgG | anti-Her2-IgG/sialidase | anti-Her2-IgG-Sia |
| SKBR3 | 3+ | 177 ± 54/61 ± 3 | 136 ± 52/64 ± 4 | 76 ± 14/66 ± 2 |
| HCC-1954 | 3+ | 360 ± 67/46 ± 2 | 212 ± 50/46 ± 2 | 238 ± 41/49 ± 2 |
| MDA-MB-453 | 2+ | 110 ± 27/71 ± 3 | 77 ± 17/78 ± 3 | 22 ± 5/75 ± 2 |
| ZR-75-1 | 1+ | 1143 ± 274/14 ± 1 | 492 ± 67/34 ± 1 | 135 ± 47/34 ± 2 |
| BT-20 | 1+ | 1823 ± 850/21 ± 1 | 692 ± 156/51 ± 2 | 170 ± 34/46 ± 1 |
| MDA-MB-231 | 1+ | N.D./6 ± 1 | N.D./10 ± 1 | N.D./10 ± 1 |
| MDA-MB-468 | — | N.D./2 ± 1 | N.D./N.D. | N.D./3 ± 1 |

Example 6—Sialidase Treatment Potentiates Rituximab-Induced CDC

Figure 17:
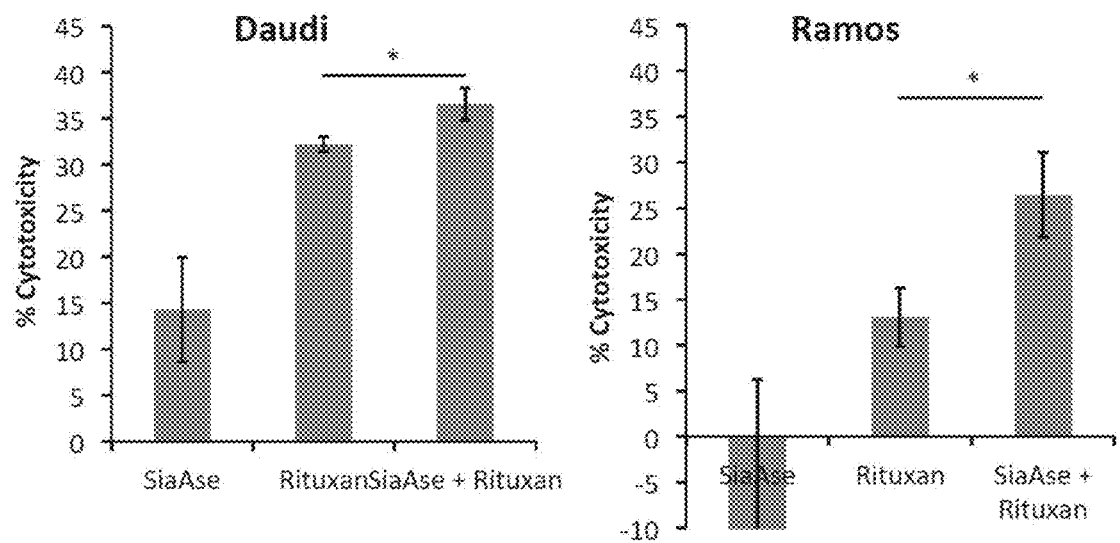
FIG. 17 depicts data demonstrating that sialidase treatment potentiates rituximab-induced complement-dependent cytotoxicity (CDC).

B cell lymphoma cells, either Daudi or Ramos cell lines, were treated with sialidase or PBS control for 1 hour at 37° C. to desialylate their cell surfaces, then normal human serum (1:4, complete with complement proteins) and rituximab (10 μg/ml) was added and the mixture allowed to incubate for 2 hours at 37° C. The supernatant was collected and cell death (cytotoxicity) was determined using a kit that measures LDH release from lysed cells then compared to fully detergent-lysed cells as a '100% killing' standard. For FIG. 17: SiAse: sialidase treated cells, no rituximab. Rituxan: PBS treated and 10 μg/ml rituximab. SiaAse+Rituxan: sialidase treated and 10 μg/mL rituximab. * p<0.05

Daudi cells experience ~10% increase in rituximab-induced complement-dependent cytotoxicity (CDC). Ramos, on the other hand, experience almost twice as much CDC after desialylation.

Example 7—Ramos Cells have Higher Levels of Siglec-9 Ligands than Daudi Cells

The greater effect on CDC by desialylation seen with Ramos cells in the preceding example could be explained by higher initial sialylation.

Siglec-Fc fusion proteins were pre-complexed at 5 μg/ml Sig-Fc and 4 μg/ml anti-Fc secondary and incubated with cells for 30 min at 4° C. Cells were then washed 3 times and flow cytometry was performed. Separately, cells were treated with the anti-Fc secondary antibody (same 4 μg/ml), then washed as above and flow cytometry was performed. Increase in fluorescence of the Siglec-Fc fusion treated cells over the secondary-only treated cells indicates that binding was due to the Siglec-Fc protein, and not the secondary reagent.

Figure 18:
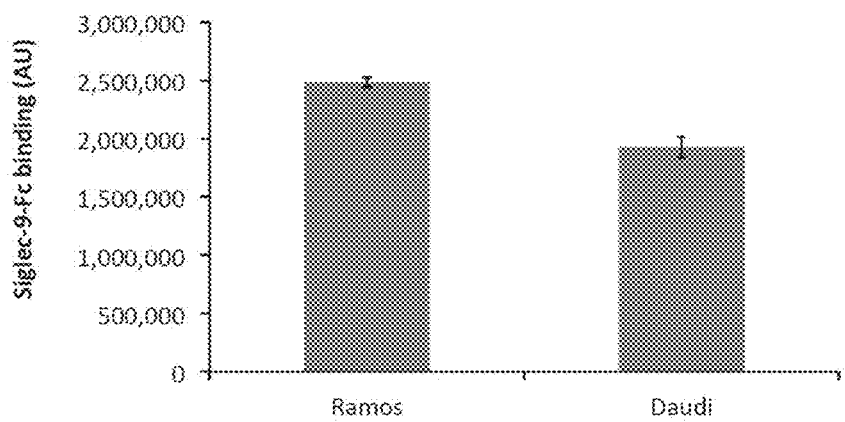
FIG. 18 depicts data showing that Ramos cells have higher levels of Siglec-9 ligands than Daudi cells.

Shown in FIG. 18 is the average +/−standard deviation of Siglec-9-Fc binding of triplicate experimental replicates of Daudi and Ramos cell lines. Ramos cells show ~25% more Siglec-9 binding, thus likely display more sialic acid on their cell surfaces.

Example 8—Sialidase Potentiates Rituximab in a Complement-Dependent Manner

Figure 19:
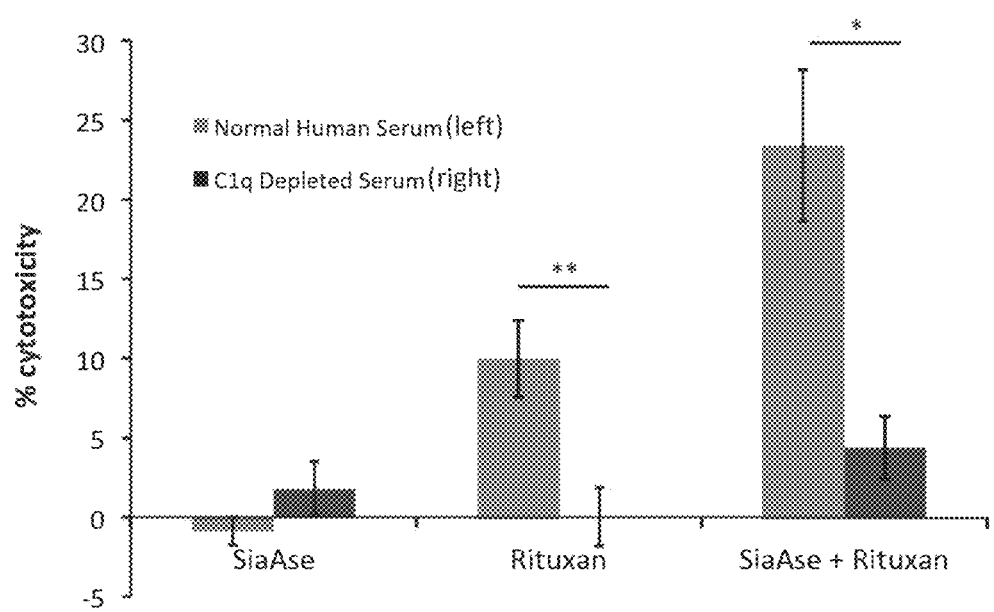
FIG. 19 depicts data demonstrating that sialidase potentiates rituximab in a complement-dependent manner.

Complement protein C1q is a critical initiating component of the 'classical pathway' of complement-dependent cytotoxicity. It helps form the C1 complex, which binds antibodies on target cells and then initiates the complement cascade which leads to cell death. As shown in FIG. 19, without C1q, the sialidase and/or rituximab does not efficiently lyse cells. This data indicates that sialidase treatment is potentiating the rituximab-induced CDC via the classical pathway. These experiments were performed as in FIG. 17, however for the red bars, serum that has been depleted of C1q was added in place of normal human serum. The blue bars represent cells treated with normal human serum. * p<0.05, ** p<0.01

Effect of Antibody-Sialidase Conjugate on the Immune Synapse

In previous work, it was demonstrated that Siglec-7 is recruited to the NK-target cell immunological synapse, thus inducing inhibitory signaling through an immunoreceptor tyrosine-based inhibition motif (ITIM). To assess the effect of conjugated sialidase on the immune synapse, the immune synapse was imaged during ADCC. SKBR3 cells were pre-incubated with anti-Her2-IgG or anti-Her2-IgG-Sia and then they were co-incubated with purified human peripheral blood NK cells to induce synapse formation. Cells were then fixed and stained for Siglec-7, HER2, FcγIII (CD16) and imaged by fluorescence microscopy. With anti-Her2-IgG treatment, Siglec-7 co-localized with FcγIII (CD16) at the immunological synapse formed with NK cells, which is consistent with its role as an inhibitory receptor of NK cell activation (FIG. 12K). In contrast, SKBR3 cells treated with anti-Her2-IgG-Sia show little recruitment of Siglec-7 despite an efficient recruitment of CD16. These results indicate that the trastuzumab-sialidase conjugate effectively remodels the immune-cancer cell synapse while promoting ADCC.

Here, a new class of conjugates that are able to perform tissue-specific cell-surface glycan editing to enhance susceptibility to ADCC is reported. The conjugates provide the first means for a single antibody therapy that simultaneously targets multiple immune-stimulating pathways. Treatment of tumor cells with antibody-sialidase conjugate not only actively recruits NK cells via Fc-FcγIII (CD16) interaction, but also effectively retards the recruitment of inhibitory Siglec receptors to the tumor-immune synapse and exposes activating NKG2D ligands through precise glycocalyx editing. Compared to trastuzumab treatment, the novel trastuzumab-sialidase conjugate can efficiently direct NK cells to kill HER2-expressing cancer cells and is even more efficient at targeting breast cancer cells with antigens of low abundance. This has significant implications for the ability to treat more moderate HER2-expressing tumors as trastuzumab is currently only prescribed to patients with the very high HER2 expression levels.

Notably, macrophages and dendritic cells also express inhibitory Siglecs (Siglec-9 and -5, respectively). Thus, hypersialylation may be broadly protective against innate immune targeting by cells and complement factors.

Unlike current cancer immune therapies, which each target a single pathway, glycocalyx editing can affect multiple pathways across various branches of the immune system's armament.

Notwithstanding the appended claims, the present disclosure is also defined by the following clauses:

1. A conjugate, comprising:
   a targeting moiety that binds to a cell surface molecule of a target cell; and
   a target cell surface-editing enzyme.
2. The conjugate of Clause 1, wherein the targeting moiety is selected from the group consisting of: an antibody, a ligand, an aptamer, a nanoparticle, and a small molecule.
3. The conjugate of Clause 2, wherein the targeting moiety is an antibody.
4. The conjugate of Clause 3, wherein the antibody is an IgG, a single chain Fv (scFv), Fab, (Fab)$_2$, or (scFv')$_2$.
5. The conjugate of Clause 3, wherein the antibody is an IgG1.
6. The conjugate of any one of Clauses 3 to 5, wherein the antibody is a monoclonal antibody.
7. The conjugate of any one of Clauses 3 to 6, wherein the antibody is a humanized or human antibody.
8. The conjugate of any one of Clauses 3 to 7, wherein the target cell surface-editing enzyme is conjugated to a light chain of the antibody.
9. The conjugate of any one of Clauses 3 to 7, wherein the target cell surface-editing enzyme is conjugated to a heavy chain of the antibody.
10. The conjugate of Clause 9, wherein the target cell surface-editing enzyme is conjugated to an Fc region of the antibody.
11. The conjugate of Clause 9, wherein the target cell surface-editing enzyme is conjugated to the C-terminus of the heavy chain.
12. The conjugate of any one of Clauses 1 to 11, wherein the target cell surface-editing enzyme is site-specifically conjugated to the targeting moiety.
13. The conjugate of Clause 12, wherein the targeting moiety comprises a non-natural amino acid to which the target cell surface-editing enzyme is site-specifically conjugated.
14. The conjugate of any one of Clauses 1 to 13, wherein the target cell surface-editing enzyme is conjugated to the targeting moiety via a linker.
15. The conjugate of Clause 14, wherein the linker comprises polyethylene glycol (PEG).
16. The conjugate of Clause 14, wherein the linker is a peptide.
17. The conjugate of Clause 16, wherein the conjugate is a fusion protein.
18. The conjugate of any one of Clauses 1 to 15, wherein the target cell is selected from the group consisting of: a cancer cell, an immune cell, and an endothelial cell.
19. The conjugate of Clause 18, wherein the target cell is a cancer cell.
20. The conjugate of Clause 19, wherein the cell surface molecule is a tumor-associated cell surface molecule.
21. The conjugate of Clause 19, wherein the cell surface molecule is a tumor-specific cell surface molecule.
22. The conjugate of any one of Clauses 19 to 21, wherein the cancer cell is a carcinoma cell.
23. The conjugate of any one of Clauses 19 to 22, wherein the cancer cell is selected from the group consisting of: a breast cancer cell, an ovarian cancer cell, a gastric cancer cell, and a colon cancer cell.
24. The conjugate of Clause 22 or Clause 23, wherein the cell surface molecule is human epidermal growth factor receptor 2 (HER2).
25. The conjugate of Clause 24, wherein the targeting moiety is trastuzumab.
26. The conjugate of any one of Clauses 3 to 18, wherein the targeting moiety is selected from the group consisting of: cetuximab, daratumumab, girentuximab, panitumumab, ofatumumab, and rituximab.
27. The conjugate of any one of Clauses 1 to 26, wherein the target cell surface-editing enzyme cleaves a molecule on the surface of the target cell, oxidizes a molecule on the surface of the target cell, reduces a molecule on the surface of the target cell, adds a moiety to a molecule on the surface of the target cell, or removes a moiety from a molecule on the surface of the target cell.
28. The conjugate of any one of Clauses 1 to 26, wherein the target cell surface-editing enzyme cleaves a molecule on the surface of the target cell.
29. The conjugate of Clause 28, wherein the molecule on the surface of the target cell is a ligand.
30. The conjugate of Clause 29, wherein the ligand is a ligand of an inhibitory immune receptor.
31. The conjugate of Clause 30, wherein the inhibitory immune receptor is present on an immune cell selected from the group consisting of: a natural killer (NK) cell, a macrophage, a monocyte, a neutrophil, a dendritic cell, a T cell, a B cell, a mast cell, a basophil, and an eosinophil.
32. The conjugate of Clause 31, wherein the inhibitory immune receptor is a sialic acid-binding Ig-like lectin (Siglec) receptor.
33. The conjugate of Clause 32, wherein the Siglec receptor is Siglec 7.
34. The conjugate of Clause 32, wherein the Siglec receptor is Siglec 9.
35. The conjugate of any one of Clauses 29 to 34, wherein the ligand is a sialoglycan.
36. The conjugate of any one of Clauses 1 to 35, wherein the target cell surface-editing enzyme is a sialidase.
37. The conjugate of Clause 36, wherein the sialidase is a *Salmonella typhimurium* sialidase.
38. The conjugate of Clause 36, wherein the sialidase is a *Vibrio cholerae* sialidase.
39. The conjugate of Clause 36, wherein the sialidase is a mammalian neuraminidase.
40. The conjugate of Clause 39, wherein the mammalian neuraminidase is a human neuraminidase.
41. The conjugate of Clause 40, wherein the human neuraminidase is selected from the group consisting of: human neuraminidase 1, human neuraminidase 2, human neuraminidase 3, and human neuraminidase 4.
42. The conjugate of any one of Clauses 1 to 41, comprising two or more target cell surface-editing enzymes conjugated to the targeting moiety.
43. A composition, comprising:
    a conjugate of any one of Clauses 1 to 42; and
    a pharmaceutically acceptable carrier.
44. The composition of Clause 43, wherein the composition is formulated for parenteral administration.
45. A method comprising administering to an individual in need thereof a conjugate of any one of Clauses 1 to 42 or a composition of Clause 43 or Clause 44.

46. A method of treating cancer comprising administering to an individual having cancer a conjugate of any one of Clauses 1 to 42 or a composition of Clause 43 or Clause 44.
47. A method of enhancing antibody-dependent cellular cytotoxicity (ADCC) comprising administering to an individual in need of ADCC a conjugate of any one of Clauses 1 to 39 or a composition of Clause 40 or Clause 41.
48. The method according to any one of Clauses 45 to 47, wherein the administering modulates an immune pathway in the individual.
49. The method according to Clause 48, wherein the immune pathway is selected from the group consisting of: an inhibitory immune receptor pathway, a complement pathway, a paired immunoglobulin-like type 2 receptor (PILR) pathway, and a natural-killer group 2 member D protein (NKG2D) pathway.
50. The method according to any one of Clauses 45 to 49, wherein the target cell comprises a ligand on its surface, and the administering results in editing of the ligand by the target cell surface-editing enzyme.
51. The method according to Clause 50, wherein the editing of the ligand comprises cleavage of all or a portion of the ligand.
52. The method according to Clause 50 or Clause 51, wherein the ligand is a ligand of an inhibitory immune receptor.
53. The method according to Clause 52, wherein the inhibitory immune receptor is present on an immune cell selected from the group consisting of: a natural killer (NK) cell, a macrophage, a monocyte, a neutrophil, a dendritic cell, a T cell, a B cell, a mast cell, a basophil, and an eosinophil.
54. The method according to Clause 53, wherein the inhibitory immune receptor is a sialic acid-binding Ig-like lectin (Siglec) receptor.
55. The method according to Clause 54, wherein the Siglec receptor is Siglec 7.
56. The method according to Clause 54, wherein the Siglec receptor is Siglec 9.
57. The method according to any one of Clauses 50 to 56, wherein the ligand is a sialoglycan.
58. The method according to Clause 57, wherein the target cell surface-editing enzyme is a sialidase.
59. The method according to Clause 58, wherein the sialidase is a *Salmonella typhimurium* sialidase.
60. The method according to Clause 58, wherein the sialidase is a *Vibrio cholerae* sialidase.
61. The method according to Clause 58, wherein the sialidase is a mammalian neuraminidase.
62. The method according to Clause 61, wherein the mammalian neuraminidase is a human neuraminidase.
63. The method according to Clause 62, wherein the human neuraminidase is selected from the group consisting of: human neuraminidase 1, human neuraminidase 2, human neuraminidase 3, and human neuraminidase 4.
64. The method according to any one of Clauses 50 to 63, wherein editing of the ligand by the target cell surface-editing enzyme enhances natural killer (NK) cell activation by increasing natural-killer group 2 member D protein (NKG2D) binding to a NKG2D ligand on the target cell surface.
65. The method according to any one of Clauses 45 to 64, wherein the individual has cancer, and wherein the conjugate comprises a targeting moiety that binds to a tumor-associated cell surface molecule or tumor-specific cell surface molecule on the surface of a cancer cell of the individual.
66. The method according to Clause 65, wherein the cancer cell is a carcinoma cell.
67. The method according to Clause 65 or Clause 66, wherein the cancer cell is selected from the group consisting of: a breast cancer cell, an ovarian cancer cell, a gastric cancer cell, and a colon cancer cell.
68. The method according to Clause 66 or Clause 67, wherein the cell surface molecule is human epidermal growth factor receptor 2 (HER2).
69. The method according to Clause 68, wherein the targeting moiety is trastuzumab.
70. The method according to any one of Clauses 45 to 63, wherein the targeting moiety is selected from the group consisting of: cetuximab, daratumumab, girentuximab, panitumumab, ofatumumab, and rituximab.
71. A kit comprising the conjugate of any one of Clauses 1 to 42 or a composition of Clause 43 or Clause 44.
72. The kit of Clause 71, wherein the kit comprises the conjugate or composition in one or more unit dosages.
73. The kit of Clause 72, wherein the kit comprises the conjugate or composition in two or more unit dosages.
74. The kit of any one of Clauses 71 to 73, comprising instructions for using the conjugate or composition to treat an individual in need thereof.
75. The kit of Clause 74, wherein the individual has cancer, and the instructions are for administering to the individual a therapeutically effective amount of the conjugate or composition to treat the cancer.
76. A method, comprising:
conjugating a target cell surface-editing enzyme to a targeting moiety that binds to a cell surface molecule on the surface of a target cell.
77. The method according to Clause 76, wherein the conjugating comprises site-specifically conjugating the target cell surface-editing enzyme to the targeting moiety.
78. The method according to Clause 77, wherein the conjugating comprises site-specifically conjugating the target cell surface-editing enzyme to a non-natural amino acid of the targeting moiety.
79. The method according to any one of Clauses 76 to 78, wherein the target cell surface-editing enzyme is conjugated to the targeting moiety via a linker.
80. The method according to Clause 79, wherein the linker comprises polyethylene glycol (PEG).
81. The method according to Clause 79, wherein the linker is a peptide.
82. The method according to Clause 81, wherein the conjugate is a fusion protein.
83. The method according to any one of Clauses 76 to 80, wherein the target cell surface-editing enzyme is a sialidase and the targeting moiety is an antibody.
84. The method according to Clause 83, wherein the antibody is an anti-HER2 antibody.
85. The method according to Clause 84, wherein the antibody is trastuzamab.
86. The method according to Clause 83, wherein the antibody is selected from the group consisting of: cetuximab, daratumumab, girentuximab, panitumumab, ofatumumab, and rituximab.
87. A nucleic acid encoding the fusion protein of Clause 82.
88. An expression vector comprising a promoter operably linked to the nucleic acid of Clause 87.

89. A host cell comprising the nucleic acid of Clause 87 or the expression vector of Clause 88.

90. The host cell of Clause 89, wherein the host cell is a mammalian host cell.

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. All statements herein reciting principles, aspects, and embodiments of the invention as well as specific examples thereof, are intended to encompass both structural and functional equivalents thereof. It is intended that such equivalents include currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

---

What is claimed is:

1. A method of treating cancer in an individual in need thereof, the method comprising administering to the individual a therapeutically effective amount of a conjugate comprising (a) an antibody that binds to a tumor-associated cell surface molecule of a cancer cell and (b) a sialidase conjugated to the antibody, whereupon, after administration to the individual, the sialidase cleaves a sialic acid from the surface of the cancer cell, wherein the sialic acid is a ligand for a sialic acid-binding Ig-like lectin (Siglec) receptor, wherein the sialidase is a prokaryotic sialidase or a eukaryotic sialidase.

2. The method of claim 1, wherein the conjugate, when administered to the individual, modulates an immune pathway in the individual.

3. The method of claim 1, wherein the conjugate, when administered to the individual, cleaves all or a portion of the sialic acid from the surface of the cancer cell.

4. The method of claim 1, wherein the Siglec receptor is an inhibitory immune receptor present on an immune cell selected from the group consisting of: a natural killer (NK) cell, a macrophage, a monocyte, a neutrophil, a dendritic cell, a T cell, a B cell, a mast cell, a basophil, and an eosinophil.

5. The method of claim 1, wherein the Siglec receptor is Siglec 7.

6. The method of claim 1, wherein the Siglec receptor is Siglec 9.

7. The method of claim 1, wherein the sialidase is a bacterial sialidase.

8. The method of claim 7, wherein the bacterial sialidase is a *Salmonella typhimurium* sialidase or a *Vibrio cholerae* sialidase.

9. The method of claim 8, wherein the sialidase is a *Vibrio cholerae* sialidase.

10. The method of claim 1, wherein the sialidase is a mammalian neuraminidase.

11. The method of claim 10, wherein the mammalian neuraminidase is a human neuraminidase.

12. The method of claim 11, wherein the sialidase is a human neuraminidase selected from the group consisting of: human neuraminidase 1, human neuraminidase 2, human neuraminidase 3, and human neuraminidase 4.

13. The method of claim 1, wherein the antibody is an IgG, a single chain Fv (scFv), Fab, (Fab)$_2$, or (scFv')$_2$.

14. The method of claim 1, wherein the antibody comprises a fragment crystallizable (Fc) region.

15. The method of claim 14, wherein the sialidase is conjugated to the Fc region of the antibody.

16. The method of claim 1, wherein the sialidase is conjugated to a heavy chain of the antibody.

17. The method of claim 16, wherein the sialidase is conjugated to the C-terminus of the heavy chain.

18. The method of claim 1, wherein the sialidase is conjugated to the antibody via a linker.

19. The method of claim 1, wherein the conjugate is a fusion protein.

20. The method of claim 1, wherein cleavage of sialic acid on the surface of the cancer cell enhances natural killer (NK) cell activation by increasing natural-killer group 2 member D protein (NKG2D) binding to a NKG2D ligand on the cancer cell surface.

21. The method of claim 1, wherein the cancer cell is a carcinoma cell.

22. The method of claim 1, wherein the cancer cell is selected from the group consisting of: a breast cancer cell, an ovarian cancer cell, a gastric cancer cell, and a colon cancer cell.

23. The method of claim 1, wherein the cell surface molecule is human epidermal growth factor receptor 2 (HER2).

24. The method of claim 1, wherein the antibody is trastuzumab.

25. The method of claim 1, wherein the antibody is selected from the group consisting of: cetuximab, daratumumab, girentuximab, panitumumab, ofatumumab, and rituximab.

* * * * *

SEQUENCE LISTING

```
Sequence total quantity: 4
SEQ ID NO: 1              moltype = AA  length = 214
FEATURE                   Location/Qualifiers
REGION                    1..214
                          note = Synthetic sequence
source                    1..214
                          mol_type = protein
                          organism = synthetic construct
SEQUENCE: 1
DIQMTQSPSS LSASVGDRVT ITCRASQDVN TAVAWYQQKP GKAPKLLIYS ASFLYSGVPS    60
RFSGSRSGTD FTLTISSLQP EDFATYYCQQ HYTTPPTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 2              moltype = AA  length = 451
FEATURE                   Location/Qualifiers
REGION                    1..451
                          note = Synthetic sequence
source                    1..451
                          mol_type = protein
                          organism = synthetic construct
SEQUENCE: 2
EVQLVESGGG LVQPGGSLRL SCAASGFNIK DTYIHWVRQA PGKGLEWVAR IYPTNGYTRY    60
ADSVKGRFTI SADTSKNTAY LQMNSLRAED TAVYYCSRWG DGDGFYAMDYW GQGTLVTVSS  120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                  451

SEQ ID NO: 3              moltype = AA  length = 381
FEATURE                   Location/Qualifiers
source                    1..381
                          mol_type = protein
                          organism = Salmonella typhimurium sialidase
SEQUENCE: 3
TVEKSVVFKA EGEHFTDQKG NTIVGSGSGG TTKYFRIPAM CTTSKGTIVV FADARHNTAS    60
DQSFIDTAAA RSTDGGKTWN KKIAIYNDRV NSKLSRVMDP TCIVANIQGR ETILVMVGKW   120
NNNDKTWGAY RDKAPDTDWD LVLYKSTDDG VTFSKVETNI HDIVTKNGTI SAMLGGVGSG   180
LQLNDGKLVF PVQMVRTKNI TTVLNTSFIY STDGITWSLP SGYCEGFGSE NNIIEFNASL   240
VNNIRNSGLR RSFETKDFGK TWTEFPPMDK KVDNRNHGVQ GSTITIPSGN KLVAAHSSAQ   300
NKNNDYTRSD ISLYAHNLYS GEVKLIDDFY PKVGNASGAG YSCLSYRKNV DKETLYVVYE   360
ANGSIEFQDL SRHLPVIKSY N                                             381

SEQ ID NO: 4              moltype = AA  length = 757
FEATURE                   Location/Qualifiers
source                    1..757
                          mol_type = protein
                          organism = Vibrio cholerae sialidase
SEQUENCE: 4
ALFDYNATGD TEFDSPAKQG WMQDNTNNGS GVLTNADGMP AWLVQGIGGR AQWTYSLSTN    60
QHAQASSFGW RMTTEMKVLS GGMITNYYAN GTQRVLPIIS LDSSGNLVVE FEGQTGRTVL   120
ATGTAATEYH KFELVFLPGS NPSASFYFDG KLIRDNIQPT ASKQNMIVWG NGSSNTDGVA   180
AYRDIKFEIQ GDVIFRGPDR IPSIVASSVT PGVVTAFAEK RVGGGDPGAL SNTNDIITRT   240
SRDGGITWDT ELNLTEQINV SDEFDFSDPR PIYDPSSNTV LVSYARWPTD AAQNGDRIKP   300
WMPNGIFYSV YDVASGNWQA PIDVTDQVKE RSFQIAGWGG SELYRRNTSL NSQQDWQSNA   360
KIRIVDGAAN QIQVADGSRK YVVTLSIDES GGLVANLNGV SAPIILQSEH AKVHSFHDYE   420
LQYSALNHTT TLFVDGQQIT TWAGEVSQEN NIQFGNADAQ IDGRLHVQKI VLTQQGHNLV   480
EFDAFYLAQQ TPEVEKDLEK LGWTKIKTGN TMSLYGNASV NPGPGHGITL TRQQNISGSQ   540
```

```
NGRLIYPAIV  LDRFFLNVMS  IYSDDGGSNW  QTGSTLPIPF  RWKSSSILET  LEPSEADMVE  600
LQNGDLLLTA  RLDFNQIVNG  VNYSPRQQFL  SKDGGITWSL  LEANNANVFS  NISTGTVDAS  660
ITRFEQSDGS  HFLLFTNPQG  NPAGTNGRQN  LGLWFSFDEG  VTWKGPIQLV  NGASAYSDIY  720
QLDSENAIVI  VETDNSNMRI  LRMPITLLKQ  KLTLSQN                             757
```